United States Patent
Ye et al.

(10) Patent No.: US 9,574,205 B2
(45) Date of Patent: Feb. 21, 2017

(54) MICROSOMAL ω6 OLEATE DESATURASES

(75) Inventors: Jian Ye, Singapore (SG); Jing Qu, Singapore (SG); Hui Zhu Mao, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 524 days.

(21) Appl. No.: 14/118,767

(22) PCT Filed: Sep. 28, 2011

(86) PCT No.: PCT/SG2011/000337
§ 371 (c)(1),
(2), (4) Date: Nov. 19, 2013

(87) PCT Pub. No.: WO2012/166049
PCT Pub. Date: Dec. 6, 2012

(65) Prior Publication Data
US 2014/0096288 A1    Apr. 3, 2014

(30) Foreign Application Priority Data
May 27, 2011   (WO) ............... PCT/SG2011/000197

(51) Int. Cl.
*C12N 15/82*     (2006.01)
*C12N 5/14*      (2006.01)
*C12N 9/02*      (2006.01)
*C12P 7/64*      (2006.01)

(52) U.S. Cl.
CPC ........... *C12N 15/8247* (2013.01); *C12N 9/001* (2013.01); *C12N 9/0083* (2013.01); *C12N 15/8218* (2013.01); *C12P 7/64* (2013.01); *C12Y 103/01035* (2013.01); *C12N 5/14* (2013.01); *Y02P 20/52* (2015.11)

(58) Field of Classification Search
None
See application file for complete search history.

(56) References Cited

U.S. PATENT DOCUMENTS

2007/0130642 A1* 6/2007 Glassman ............... C12N 15/63
                                                              800/278
2008/0076164 A1* 3/2008 Cirpus .................. C12N 9/0006
                                                              435/134

FOREIGN PATENT DOCUMENTS

WO   2006073787 A2   7/2006
WO   2008006171 A1   1/2008
WO   2010080071 A1   7/2010

OTHER PUBLICATIONS

Ye et al 2009 (Plant Biotechnology Journal 7:p. 964-976).*
Senthil-Kumar et al 2014 (Nature Protocols 9: p. 1549-1562).*
Qing et al 2006 (Genbank DQ157776.1).*
GenBank Accession No. DQ157776, Nov. 30, 2005, Jatropha curcas delta12-fatty acid desaturase mRNA, complete cds, 1 page.
GenBank Accession No. GU353167, Feb. 1, 2010, Jatropha curcas delta-12-fatty acid desaturase gene, complete cds, 1 page.
GenBank Accession No. AF525535, Dec. 19, 2002, Vernicia fordil delta 12 fatty acid conjugase FADX mRNA, complete cds, 2 pages.
Mroczka, A. et al., "An Intron Sense Suppression Construct Targeting Soybean FAD2-1 Requires a Double-Stranded RNA-Producing Inverted Repeat T-DNA Insert," Plant Physiology, Jun. 2010, vol. 153, pp. 882-891, copyright 2010 American Society of Plant Biologists.

* cited by examiner

*Primary Examiner* — Matthew Keogh
(74) *Attorney, Agent, or Firm* — Rothwell, Figg, Ernst & Manbeck, P.C.

(57) ABSTRACT

The present invention relates to the field of plant molecular biology, more particularly *Jatropha* microsomal co6 oleate desaturases. The present invention also relates to *Jatropha* plants or plants of other oil crops having seeds with altered ratios of monosaturated and polyunsaturated fats. In particular, the present invention relates to *Jatropha* plants or plants of other oil crops where the plants exhibit elevated levels of oleic acid.

3 Claims, 7 Drawing Sheets

Fig. 1A

```
  1  MGAGGRMSVP PSPKKLEAEV LKRVPYSKPP FTLGQVKKAI PPHCFQRSVL
 51  RSFSYVVYDL TLAFIFYYVA TNYFHLLPQP LSYVAWPIYW SLQGCVLTGI
101  WVIAHECGHH AFSDYQWLDD IVGLLLHSCL LVPYFSWKHS HRRHHSNTGS
151  LERDEVFVPK KKSNIRWFSK YLNNLPGRLF TLTITLALGW PLYLAFNVSG
201  RHYDRFACHF DPYGPIYNDR ERTEIFISDA GVLAVTYGLY RLALAKGFAW
251  VICVYGVPLL VVNAFLVMIT YLQHTHPSLP HYDSSEWDWL RGALATVDRD
301  YGILNKVFHN ITDTHVAHHL FSTMPHYHAM EATNAIKPIL GEYYQFDRTP
351  FFKAMWREAK ECIYVEPDDA DQSRGVF WYK NKF
```

Fig. 1B

```
  1  MGAGGQKTAV LVSSKFKEWE TNRRLKRVPH TKPPFTLGQI KQAIPSHCFK
 51  RSLLRSFSYL VYDLSLSSLF YYIAASYFHL LPSPISYIAW PIYWTLQGCT
101  LTGVWVIAHE CGHHAFSDYQ WVDDTVGLIL HSSLLVPYFS WKISHRRHHS
151  NTGSIERDEV FVPKFKSRIP WYSQYLNNPL GRALALAATL TVGWPLYLAF
201  NVSGRPYNRF ACHFDPSGPI YSDRERLQIY ISDIGIFAAT YVLYQIAMAK
251  GLAWLISIYG IPLLIVNAFL VTITYLQHTH THHLFSTMPH YHAMEATKAI KPILGEYYQF
301  VDRDYGVLNK VFHNITDTHV THHLFSTMPH YHAMEATKAI KPILGEYYQF
351  DGTPILMALW REAKECLFVE PEEGGPNRGV LWYGNKY
```

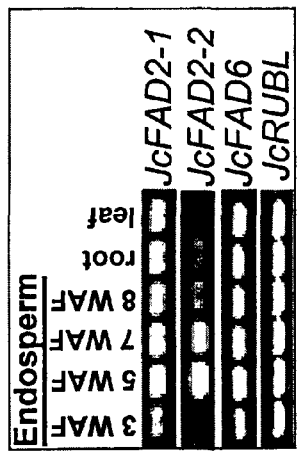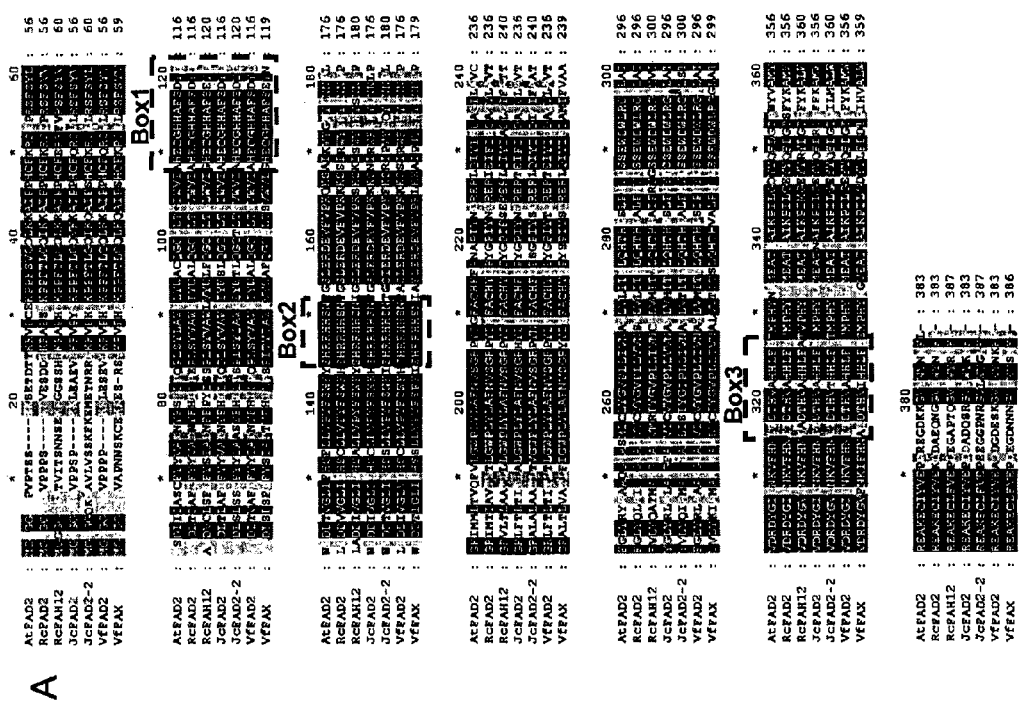
Fig. 2

MICROSOMAL ω6 OLEATE DESATURASES

CROSS-REFERENCE TO RELATED APPLICATION

The present application is a national phase entry under 35 U.S.C. §371 of PCT/SG2011/000337, filed 28 Sep. 2011, which claims priority to International Patent Application No.PCT/SG2011/000197 filed 27 May 2011. Each application is incorporated herein by reference in its entirety.

SEQUENCE SUBMISSION

The present application is being filed along with a Sequence Listing in electronic format. The Sequence Listing is entitled 2577208PCT2SequenceListing.txt, was created on 16 Aug. 2011 and is 127 kb in size. The information in the electronic format of the Sequence Listing is part of the present application and is incorporated herein by reference in its entirety.

BACKGROUND OF THE INVENTION

The present invention relates to the field of plant molecular biology, more particularly Jatropha microsomal ω6 oleate desaturases. The present invention also relates to Jatropha plants or plants of other oil crops having seeds with altered ratios of monosaturated and polyunsaturated fats. In particular, the present invention relates to Jatropha plants or plants of other oil crops where the plants exhibit elevated levels of oleic acid.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Plant oils have many kinds of diverse applications. Novel vegetable oil compositions and improved approaches to obtain oil compositions, from biosynthetic or natural plant sources, are needed. Depending upon the intended oil use, various different fatty acid compositions are desired. Plants, especially species which synthesize large amounts of oils in seeds, are an important source of oils both for edible and industrial uses (Lu et al.; Durrett et al., 2008).

One major usage for plant oil is for food. Plant oils are mostly composed of five common fatty acids, namely palmitic acid (16:0), stearic acid (18:0), oleic acid (18:1), linoleic acid (18:2) and linolenic acid (18:3) (Durrett et al., 2008). Oleic acid is a monounsaturated omega-9 and 18 carbon fatty acid found in various vegetable oils. It is considered one of the healthier sources of oil and fat in food resources for human and animal. Diets in which oil consumption are high in oleic acid have been proven to downregulate overall levels of chronic human diseases such as cholesterol, arteriosclerosis and cardiovascular disease. Specifically, oleic acid has been shown to raise levels of high-density lipoproteins (HDLs) known as "good cholesterol", while lowering low-density lipoproteins (LDLs) also known as the "bad" cholesterol. Thus, the development of new and inexpensive sources of foods comprising healthier forms of fatty acid is desirable.

One emerging purpose for oil is to serve as feedstock of renewable bioenergy in the form of biodiesel. The demand for use biodiesel, mainly comes from vegetable oil, has soared along with government subsidies and mandates for the alternative fuel. Because there are various fatty acid composition of each types, the fuel properties of biodiesel derived from a mixture of fatty acids are dependent on that composition. Compared with conventional diesel, there are some negative factors of fatty acid profile should be optimized by traditional breeding or genetic engineering to optimize biodiesel fuel characteristics. Various studies suggest that biodiesel with high levels of methyl oleate will have excellent, characteristics with regard to ignition quality, $NO_x$ emissions and fuel stability. For example, while unsaturation tends to reduce the cetane number of biodiesel, that of methyl oleate is higher than the minimal biodiesel standard. Additionally, it has been estimated that biodiesel fuels with an average of 1.5 double bonds per molecule will emit an equivalent amount of $NO_x$ compared with conventional diesel, thus a fuel high in oleates should not result in higher $NO_x$ emissions. Finally, given that polyunsaturated fatty acids have a major effect on the auto-oxidation of biodiesel, high oleic acid with reduced polyunsaturated fatty acid content will improve the stability of the fuel (Durrett et al., 2008).

Soybean lines with high levels of oleic acid and low levels of saturated and polyunsaturated fatty acids have been developed using a transgenic strategy that results in down-regulation of one single gene fatty acid desaturase 2 (FAD2). Consistent with predictions, biodiesel synthesized from these high-oleic soybeans demonstrated improved fuel characteristics with regard to cold-temperature flow properties and $NO_x$ emissions (Tat et al., 2007; Graef et al., 2009).

During the last several years, many countries have begun to target biofuel research as a national priority and implement compulsory blending of fossil fuel with biofuel. The increasing demand for biofuel, however, is exerting more pressure on food production because of the competition between fuel crops and food crops for arable land. One way to ease this competition is to use marginal land for bioenergy production (Carroll and Somerville, 2008).

Jatropha curcas, a small woody plant belonging to Euphorbiaceae, is a non-food crop mainly grown in the tropical and subtropical regions. This plant possesses several properties rendering it suitable for biodiesel production, such as its rapid growth, ease of propagation, short gestation period, low seed cost, high oil content, wide adaptability, and drought tolerance (Jones N, 1991; Fairless, 2007). Furthermore, Jatropha may yield more than four times as much fuel per hectare as soybean, and more than ten times that of maize (corn) (http://en.wikipedia.org/wiki/Jatropha_oil). Especially important is that Jatropha can thrive on degraded soil (Fairless, 2007) making it an attractive crop for biodiesel feedstock since it can be planted on a large-scale on marginal land unsuitable for food crops.

Plants synthesize fatty acids via a common metabolic pathway known as the fatty acid synthase (FAS) pathway. Beta-ketoacyl-ACP (acyl carrier protein moiety) synthases are important rate-limiting enzymes in the FAS of plant cells and exist in several versions. Beta-ketoacyl-ACP synthase I catalyzes chain elongation to palmitoyl-ACP (C16:0), whereas Beta-ketoacyl-ACP synthase II catalyzes chain elongation to stearoyl-ACP (C18:0). Beta-ketoacyl-ACP synthase IV is a variant of Beta-ketoacyl-ACP synthase II, and can also catalyze chain elongation to 18:0-ACP. In soybeans, the major products of FAS are 16:0-ACP and 18:0-ACP. The desaturation of 18:0-ACP to form 18:1-ACP is catalyzed by a plastid-localized soluble delta-9 desaturase (also referred to as "stearoyl-ACP desaturase").

The products of the plastidial FAS and delta-9 desaturase, 16:0-ACP, 18:0-ACP, and 18:1-ACP, are hydrolyzed by specific thioesterases. Plant thioesterases can be classified into two gene families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). Such thioesterases have an important role in determining chain length during de novo fatty acid biosynthesis in plants, and thus these enzymes are useful in the provision of various modifications of fatty acyl compositions, particularly with respect to the relative proportions of various fatty acyl groups that are present in seed storage oils.

The products of the FATA and FATB reactions, the free fatty acids, leave the plastids and are converted to their respective acyl-CoA esters. Acyl-CoAs are substrates for the lipid-biosynthesis pathway (Kennedy Pathway), which is located in the endoplasmic reticulum (ER). This pathway is responsible for membrane lipid formation as well as the biosynthesis of triacylglycerols, which constitute the seed oil. In the ER there are additional membrane-bound desaturases, which can further desaturate 18:1 to polyunsaturated fatty acids.

Various technologies for generating mid to high oleic acid levels in soybean plants are known. For example, U.S. Patent Publication No. 2007/0214516 discloses a method for obtaining soybean plants that have moderately increased levels of oleic acid.

SUMMARY OF THE INVENTION

The present invention relates to genes, coding sequences, other sequences, constructs and vectors that can be used to provide a method to create and select high oleic acid lines containing around 80% oleic acid from the original level of around 40% in *Jatropha* seed oil. The genes, coding sequences, other sequences, constructs and vectors described herein, demonstrate the ability to efficiently incorporate an enhanced oil quality trait into elite varieties of *Jatropha* plants without the expensive crossing and evaluation used in traditional *Jatropha* breeding.

The *Jatropha* genome possesses two microsomal ω6 oleate desaturase, designated JcFAD2-1 and JcFAD2-2. Two cDNAs were identified and they encoded proteins of 383 (SEQ ID NO:2) and 387 amino acids (SEQ ID NO:5) that were 74% identical to each other and 77.3% and 72.1% identical to *Arabidopsis* FAD2, respectively. The cDNA with higher sequence identity to the FAD2 enzyme family was designated JcFAD2-1 and another one is named as JcFAD2-2. FAD2-1 and FAD2-2 are found in the ER where they can further desaturate oleic acid to polyunsaturated fatty acids. The delta-12 desaturase catalyzes the insertion of a double bond into oleic acid (18:1), forming linoleic acid (18:2) which results in a consequent reduction of oleic acid levels. A delta-15 desaturase (FADS) catalyzes the insertion of a double bond into linoleic acid (18:2), forming linolenic acid (18:3).

To produce selection marker free transgenic *Jatropha*, a chemically inducible Cre-loxP-mediated site-specific recombination system, which was first developed by Zuo J et al. (Zuo et al., 2001) in *Arabidopsis*, was tested. JcFAD2-1 was silenced to make high oleic acid and marker free transgenic *Jatropha*. Similar transformation procedure like above was taken to get hygromycin-resistance regeneration shoots (see WO 2010/071608, incorporated herein in by reference in its entirety). Once there are visible shoots comes out, we transfer small shoots to marker free induction medium without hygromycin. After two weeks induction, these well-growing shoots were subsequently transferred into regeneration medium II but without hygromycin. The remaining procedures are same as above normal transformation procedure.

To increase oleic acid level and reduce the unexpected environmental adaptation risk, a seed specific promoter to produce a seed specific high oleic acid in *Jatropha* was used. A soybean (*Glycine max*) seed storage protein 7S seed-specific promoter was chosen to drive hpRNA expression to downregulate JcFAD2-1 RNA. Two lines were found to contain 77.4% and 74.7% oleic acid in T1 generation endosperm. The linoleic acid were reduced to less than 5% of total fatty acid in these lines.

BRIEF DESCRIPTION OF THE FIGURES

FIGS. 1A and 1B show the amino acid composition of fatty acid desaturase enzymes in *Jatropha* (SEQ ID NO:2 and SEQ ID NO:5, respectively).

FIGS. 2A and 2B show a comparison between amino acid sequences of fatty acid desaturase enzymes from plants (FIG. 2A) and expression pattern of various genes (FIG. 2B). The sequences are as follows: AtFAD2: SEQ ID NO:7; RcFAD2: SEQ ID NO:8; RcFAH12: SEQ ID NO:9; JcFAD2: SEQ ID NO:2; JcFAD2-2: SEQ ID NO:5; VfFAD2: SEQ ID NO:10; and VfFAX: SEQ ID NO:11.

FIG. 3A: Schematic diagram of the silencing cassette and β-estradiol-induced DNA excision for high oleic acid. Size bar=1 kb. FIG. 3B: Genotyping analysis for primary transgenic shoots #1-1 and #1-2. FIG. 3C: GC analysis for primary transgenic shoots #1-1 and #1-2.

FIG. 4A: Upper DNA gel showed one of genotyping result of line 1-26 with hygromycin resistance gene primer pair (hpt) for X7-JcFAD2-1 RNAi. Lower DNA gel showed partial result of lines 1-26 with marker free primer pair (P1+P4). Note: * indicated one example line with chimeras of marker free and marker together in one plant. ** indicated one example line with complete marker free. FIG. 4B: Upper DNA gel showed one of genotyping result of lines 25-49 with hygromycin resistance gene primer pair (hpt) for X8-JcFAD2-1 RNAi. Lower DNA gel showed partial result of lines 25-49 with marker free primer pair (P7S+P4). Note: * indicated one example line (X8#34) with chimeras of marker free and marker together in one plant.

FIG. 5A: RNA analysis in T1 endosperm of #79 and #170 lines. FIG. 5B: RNA analysis in T1 leaves of #79 and #170. FIG. 5C: GC analysis to show moderate fatty acid composition changes in X7-FAD2-1 RNAi lines with T1 seeds of 35S:GFP as control.

FIG. 6A: analysis in T1 endosperm of #34 and #291 lines. FIG. 6B: RNA analysis in T1 cotyledons of #34 and #291 lines. FIG. 6C: RNA analysis in T1 true leaves of #34 and #291 lines. FIG. 6D: Oil content analysis in endosperm of #34 and #291 lines. FIG. 6E: GC analysis to show fatty acid composition changes in X8-FAD2-1 RNAi lines with T1 seeds of 35S:GFP as control. FIG. 6F: GC analysis to show no obvious fatty acid profile change in T1 true leaves.

FIG. 7A: Shows an EcoRV fragment containing JcFAD2-1. FIG. 7B:

Total genomic DNA digested with XhoI, and probed with soybean 7S promoter. * indicates the positive genomic bands containing marker. ** indicates the positive genomic bands that are marker free. FIG. 7C: Total genomic DNA digested with EcoRV and XbaI, and probed with FAD2-1 open reading frame (ORF) in the left panel and the same membrane was stripped and reprobed with hpt ORF in right panel.

DETAILED DESCRIPTION OF THE INVENTION

Figure 3:
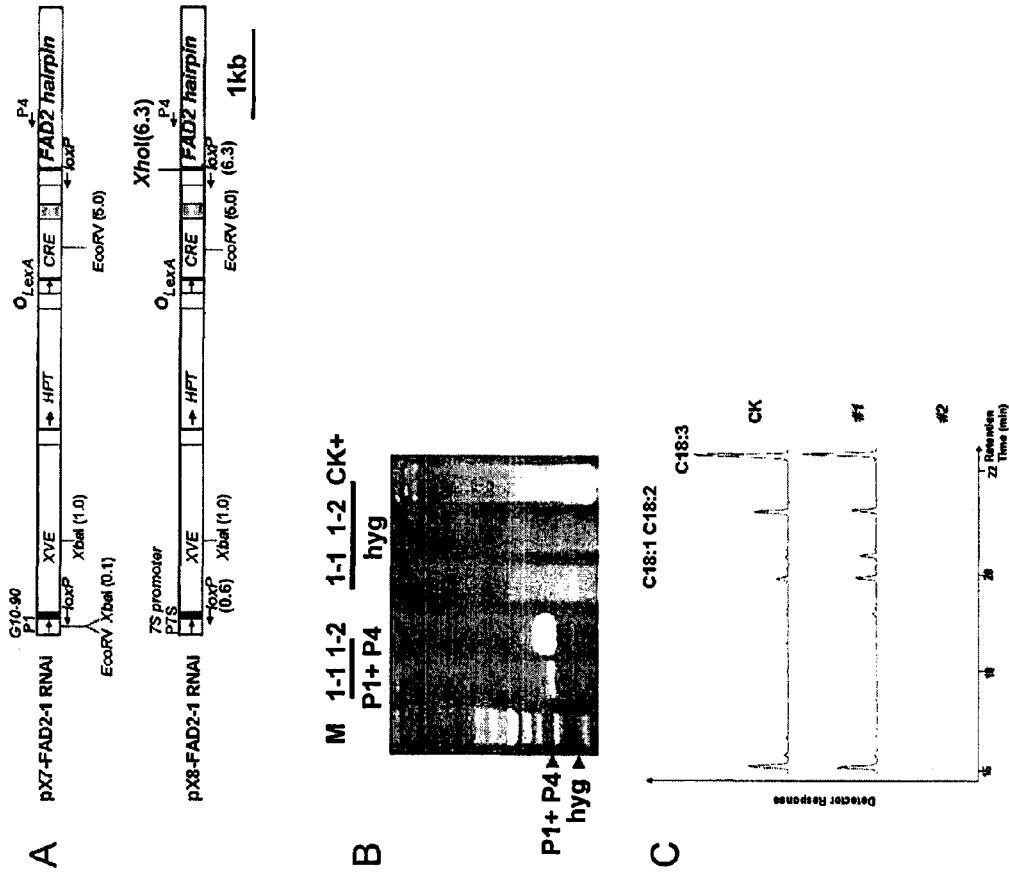
FIGS. 3A-3C show β-estradiol mediated Cre-lox marker free system in transformation medium.

Unless defined otherwise, all technical and scientific terms used herein have the same meaning as is commonly understood by one of skill in the art to which the invention belongs.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

As used herein, "FAD2" refers to a gene or encoded protein capable of catalyzing the insertion of a double bond into a fatty acyl moiety at the twelfth position counted from the carboxyl terminus. FAD2 proteins are also referred to as "delta-12 desaturase" or "omega-6 desaturase". The term "FAD2-1" is used to refer to a FAD2 gene or protein defined as sequence in the FIG. 1A (SEQ ID NO:2), coding sequence shown in ORF sequence in SEQ ID NO:1 or whole genomic sequence SEQ ID NO:3 that is naturally expressed in a multiple tissues, including the seed preferable model. The term "FAD2-2" is used to refer a FAD2 gene or protein defined as FIG. 1B (SEQ ID NO:5), coding sequence shown in ORF sequence in SEQ ID NO:4 or whole genomic sequence SEQ ID NO:6 that is (a) a different gene from a FAD2-1 gene or protein and (b) is seed specific expression.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

As used herein, "phenotype" refers to the detectable characteristics of a cell or organism, which characteristics are the manifestation of gene expression.

A "fatty acid" is a carboxylic acid that generally has a long unbranched aliphatic carbon chain. The designations (18:2), (18:1), (18:3), etc., refer to the number of carbon atoms in the fatty acid chain and the number of double bonds therein, respectively. For example, oleic acid (18:1) contains 18 carbon atoms and 1 double bond.

The present invention relates to the field of plant molecular biology, more particularly *Jatropha* microsomal ω6 oleate desaturases. The present invention also relates to *Jatropha* plants or plants of other oil crops having seeds with altered ratios of monosaturated and polyunsaturated fats. In particular, the present invention relates to *Jatropha* plants or plants of other oil crops where the plants exhibit elevated levels of oleic acid.

Thus, in a first aspect, the present invention provides an isolated nucleic acid encoding a JcFAD2-1 protein comprising the amino acid sequence set forth in SEQ ID NO:2. In one embodiment, the nucleic acid comprises the nucleotide sequence set forth in SEQ ID NO:1. In another embodiment, the nucleic acid comprises the nucleotide sequence set forth in SEQ ID NO:3. In a further embodiment, the nucleic acid further comprises a plant operable promoter operably linked to the coding sequence. In one embodiment, the promoter is a seed specific promoter. In another embodiment, the seed specific promoter is derived from an oil crop.

In a second aspect, the present invention provides an isolated nucleic acid encoding a JcFAD2-2 protein comprising the amino acid sequence set forth in SEQ ID NO:5. In one embodiment, the nucleic acid comprises the nucleotide sequence set forth in SEQ ID NO:4. In another embodiment, the nucleic acid comprises the nucleotide sequence set forth in SEQ ID NO:6. In a further embodiment, the nucleic acid further comprises a plant operable promoter operably linked to the coding sequence. In one embodiment, the promoter is a seed specific promoter. In another embodiment, the seed specific promoter is derived from an oil crop.

In a third aspect, the present invention provides a construct or vector comprising an isolated nucleic acid as described herein. In one embodiment, the construct or vector is an expression construct or vector. In another embodiment, the construct or vector further comprises a selectable marker. In a further embodiment, the construct or vector comprises a Cre-lox recombination marker free system.

In a fourth aspect, the present invention provides a transgenic plant comprising a nucleic acid or vector described herein. In one embodiment, the transgenic plant may be any plant species. In another embodiment, the transgenic plant may be a plant of an oil crop. In a further embodiment, the transgenic plant may be a *Jatropha* plant.

In a fifth aspect, the present invention provides for the down regulation of a JcFAD2-1 and/or JcFAD2-2 gene using RNA interference (RNAi), including microRNA and hairpin RNA. In one embodiment, a nucleic acid is provided which down regulates the JcFAD2-1 gene. In another embodiment, a nucleic acid is provided which down regulates the JcFAD2-2 gene. In a further embodiment, a nucleic acid is provided which down regulates the JcFAD2-1 gene, and a nucleic acid is provided which down regulates the JcFAD2-2 gene. In one embodiment, the nucleic acid further comprises a plant operable promoter operably linked to the coding sequence. In one embodiment, the promoter is a seed specific promoter. In another embodiment, the seed specific promoter is derived from an oil crop. According to this aspect, the present invention also provides a vector comprising an isolated nucleic acid as described herein. In one embodiment, the vector is an expression vector. In another embodiment, the vector further comprises a selectable marker. In a further embodiment, the vector comprises a Cre-lox recombination marker free system. According to this aspect, the present invention further provides a transgenic plant comprising a nucleic acid or vector described herein. In one embodiment, the transgenic plant may be any plant species. In another embodiment, the transgenic plant may be a plant of an oil crop. In an additional embodiment, the transgenic plant may be a castor bean plant. In a further embodiment, the transgenic plant may be a *Jatropha* plant. In one embodiment, seed of the transgenic *Jatropha* plant has an oleic acid content greater than 50%, preferably greater than 60%, more preferably greater than 70%, most preferably greater than 75%. In another embodiment, seed of the transgenic *Jatropha* plant has a linoleic acid content less than 5%.

According to this fifth aspect, the nucleic acid is selected to inhibit expression of the native DNA sequence within a plant's tissues to achieve a desired phenotype. In this case, such inhibition might be accomplished, for example, with transformation of a plant cell to comprise a promoter linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native DNA sequence in plant cells. For further description of RNAi techniques or microRNA techniques, see, e.g., U.S. Pat. Nos. 5,034,323; 6,326,527; 6,452,067; 6,573,099; 6,753,139; and 6,777,588. See also International Patent Publications WO 97/01952, WO 98/36083, WO 98/53083, WO 99/32619 and WO 01/75164; and U.S. Patent Publications 2003/0175965, 2003/0175783, 2003/0180945, 2004/0214330, 2005/0244858, 2005/0277610, 2006/0130176, 2007/0265220, 2008/0313773, 2009/0094711, 2009/0215860, 2009/0308041, 2010/0058498 and 2011/0091975. One example of an RNAi molecule is described herein. However, the present invention is not limited to this single example. Additional RNAi molecules or microRNA molecules can be prepared by the skilled artisan using techniques well known in the art, including techniques for the selection and testing of RNAi molecules and microRNA molecules that are useful for down regulating a JcFAD2-1 and/or JcFAD2-2 gene.

The construct typically includes regulatory regions operatively linked to the 5' side of the nucleic acid described herein (such a nucleic acid encoding a JcFAD2 protein or a nucleic acid encoding an RNAi molecule to down regulate a JcFAD2 gene) and/or to the 3' side of the nucleic acid. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. The promoters and tissue-specific promoters are particularly useful for preparing constructions for the transformation of Jatropha, as well as for the transformation of other oil crops. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV 35S promoter (Odell et al., 1985); rice actin (McElroy et al., 1990); ubiquitin (Christensen and Quail, 1989; Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880.

Generally, the expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 2009/0100536, and the references cited therein. See also, Jefferson et al. (1991); De Wet et al. (1987); Goff et al. (1990); Kain et al. (1995) and Chiu et al. (1996). This list of selectable marker genes is not meant to be limiting. Any selectable marker gene can be used. The selectable marker gene is also under control of a promoter operable in the plant species to be transformed. Such promoters include those described in International Publication No. WO 2008/094127 and the references cited therein.

Alternatively, the expression cassette may additionally comprise a Cre-lox recombination marker free system, such as described herein. Such a system is useful for producing selection marker free transgenic Jatropha plants or plants of other oil crops.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

DNA constructs containing the promoters of the present invention can be used to transform any plant and particularly oil palm plants. The constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein. Techniques which have been used to transform oil palm include biolistic-mediated transformation and *Agrobacterium*-mediated transformation. See, for example, Masli et al. (2009); Omidvar et al. (2008); Parveez et al. (2008); Abdullah et al. (2005); Parveez et al. (2000); Chowdhury, et al. (1997); and U.S. Patent Application Publication No. 2009/0038032. In addition, transformation of *Jatropha* has been described in International Publication No. 2010/071608.

Transformed plant cells which are derived by any of the above transformation techniques can be cultured to regenerate a whole plant which possesses the transformed genotype and thus the desired phenotype, e.g., a transgenic plant. A "transgenic plant" is a plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. See for example, International Published Application No. WO 2008/094127 and references cited therein.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants. The cultivated transgenic plants will express the DNA of interest in a tissue-preferred or tissue-specific manner as described herein.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning,* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods*

*in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Explant material for transformation: Seeds were collected from *Jatropha curcas* (Jc-MD) plants, which were selected by Drs. Yan Hong and Chenxin Yi (Yi et al., 2010) and served as starting materials. Cotyledons from 5-7 day old seedlings, germinating from ½ Murashige and Skoog salt medium, were cut into small pieces (5×5 mm).

*Jatropha* transformation procedure: For detailed procedure, please refer to Mao et al. (2009). Simply, there are 4 steps as followed procedures. 1) Co-cultivation. Small cotyledons pieces incubated with *Agrobacterium* cells harboring the target expression cassette in 20 ml of medium II for 10-20 min at 25° C. Explants were then transferred to the co-cultivation medium for 2-3 days at 22° C. in the dark. Following co-cultivation, explants were rinsed several times with sterile water, following one wash with 300 mg l$^{-1}$ cefotaxine. Cotyledon tissues were blotted dry by putting them on a pad of sterilized paper to remove excess surface water. Explants on the callus formation medium plate were transferred to darkness at 25±1° C. for three weeks. Under this condition, un-transformed explants normally will turn brown.

2) Shoot regeneration. Explants with newly emerged hygromycin-resistant callus were transferred onto the shoot regeneration medium I for 3 weeks at 25° C. with 16 h light (100 μmol m$^{-2}$S$^{-1}$)/8 h dark cycles. During this period, any shoots regenerated from callus (about 40-50%) were transferred to the shoot regeneration medium II. Callus with no regenerated shoots were transferred to the shoot regeneration medium III for further regeneration.

3) Shoot elongation. After 4 weeks, regeneration shoots were transferred onto shoot elongation medium for elongation and bud multiplication.

4A) Rooting. The elongated shoots about 2.5 cm were rooted in rooting medium. Normally it will take more than one month to get roots. Or 4B) grafting can be used to increase survival rate. Elongated shoots also can be used as scions for grafting onto non-transgenic root stocks. Healthy and vigorously growing *Jatropha* plants were chosen to be rootstocks. Both scions and rootstocks were cut into the cambium region so that phloem tissues from both will connect after joining. The graft joint was wrapped with parafilm and secured by a tape. Grafted *Jatropha* plants were maintained under low light intensity and 85% humility for 7 days.

Transgenic plasmids construction and materials: To generate the β-estradiol chemical-regulated inducible RNAi lines under-expressing JcFAD2-1, a gene-specific 862-bp fragment corresponding to the coding region of nt 85 to 946 of the JcFAD2-1 cDNA was PCR-amplified with forward primer 5'-ATCACTCGAGCCACCATTCACACTTG-GTCAG-3' (SEQ ID NO:12) and reverse primer 5'-GTATAAGCTTCATGAGTGTCTGTAATGTTATG-3' (SEQ ID NO:13). This fragment was inserted in sense orientation into the XhoI/HindIIII sites of pSK-int vector as described previously (Guo et al., 2003). The same fragment, amplified with forward primer 5'-CAATATCTAGAC-CATGGGTGCCGGTGGCAGAATG-3' (SEQ ID NO:14) and reverse primer 5'-TATTGGATCCGGAAACTT-GTTTTTGTACCAGAACAC-3' (SEQ ID NO:15), was subsequently placed in antisense orientation into the BamHI/XbaI sites of pSK-int already carrying the sense fragment to form pSK-int-FAD2-1 RNAi. Finally, the entire RNAi cassette comprising the sense and antisense fragments interspersed by the actin II intron was excised from pSK-int using the flanking XhoI/XbaI sites and inserted into the XhoI/XbaI site of pX7-GFP vector yielding the construct pX7-FAD2-1 RNAi, whose sequence is set forth in SEQ ID NO:33.

To generate the β-estradiol chemical-regulated inducible and seed-specific RNAi lines under-expressing JcFAD2-1, soybean 7S seed promoter was amplified by overlapping PCR and used to substitute for the G10-90 constitutive promoter in pX7-GFP to yield a seed-specific promoter marker free vector designated pX8-GFP. The entire FAD2-1 RNAi cassette above in pSK-int vector was inserted into pX8-GFP to substitute for the GFP coding region to form the pX8-FAD2-1 RNAi vector, whose sequence is set forth in SEQ ID NO:32.

Transformants were selected and events (X7#79, X7#170 from pX7-FAD2-1 RNAi; X8#34, X8#291 from pX8-FAD2-1 RNAi) were established using gene markers, fatty acid compositional analysis of endosperm of individual seeds. Plants were grown in a greenhouse under natural photoperiods and temperature condition (ranged from 25°-35° C.).

Fatty acid analysis: For leaf lipid profile analysis, total lipid, extracted from 100 mg fresh *Jatropha* leaves with the similar method described in (Ye et al., 2009b). Dried *Jatropha* seeds were collected and after removing the outer seed coat, seeds were surface sterilized for 60 seconds with 75% (v/v) ethanol, followed by immersion in 10% (v/v) $H_2O_2$ for 1 h, then rinsed with sterile water for two times, finally immersed in sterile water overnight at 28° C. in darkness for 24 hrs. Seed endosperm was separated carefully from the embryo. The dry endosperm part was then ground to a fine powder, and the lipids were triple extracted with hexane. The supernatant was transferred in a glass vial, and the hexane was evaporated with a flow of dry nitrogen gas at 50° C. The raw oil was weighted and the oil content was recorded as the ratio of raw oil to endosperm amount.

About 10-mg of the oil was transmethylated with 3N methanolic-HCl (SIGMA, USA) plus 400 μL 2,2, Dimethoxypropane (SIGMA, USA). The resultant FAMEs were separated by GC and detected by using GC Agilent 6890 (Palo Alto, Calif., USA) employing helium as the carrier gas and DB-23 columns for components separation. The GC analytical method was performed at 140° C. for 50 sec and a 30° C. min$^{-1}$ ramp to 240° C., and the final temperature was maintained for 50 sec. Peaks were identified based on their retention times compared with a FAME reference mixture (SIGMA, USA). Fatty acid composition value included in the analyses was calculated based on peak area percentage of total fatty acids in three biological replicates and presented as mean±standard deviation.

RNA extraction and analysis: 100 mg leaf or endosperm tissues were ground in liquid $N_2$ and extracted with plant RNA purification reagent (Invitrogen, USA). RNA concentration was measured by Nanodrop (Thermo, USA).

M-MLV reverse transcriptase (Promega, USA) was used for reverse transcription reactions. Real-time PCR was performed with Power SYBR® Green PCR Master (Applied Biosystems, USA) and run in ABI7900HT. All samples were run in triplicates and data was analyzed with RQ manager at a pre-set Ct value (Applied Biosystems, USA). The *Jatropha* rbcL mRNA served as an internal control for leaf and *Jatropha* α-tubulin mRNA served as an internal control for seed samples. Ct values included in the analyses were based on 3 biological replicates, with three technical replicates for each biological sample. Standard deviation was calculated based on 3 biological replicates. Real-time PCR primer sequences are shown in Table 1.

TABLE 1

Real-time PCR Primer Sequences

| Primer | Sequence | SEQ ID NO: |
|---|---|---|
| FAD2-1-R | GGTTGAGGAAGGAGGTGGAAG | 17 |
| FAD2-1-F | CCACCATTCACACTTGGTCAG | 18 |
| FAD2-2-F | AGCAATCAAGCCTATATTGGGC | 19 |
| FAD2-2-R | CCAGAGAACTCCTCGGTTGG | 20 |
| FAD6-F | TGGTGCATCATACGGCTC | 21 |
| FAD6-R | ATGTGAACATTGATATCATG | 22 |
| rbcl-R | CTTCTCCAGCAACGGGCTC | 23 |
| rbcl-F | GGAGTTCCGCCTGAGGAAG | 24 |
| a-tub-F | GAGGCTGGATCTGGCAAACACGTT | 25 |
| a-tub-R | TGTGTAATGACCTCTAGCAAAATTA | 26 |
| P7S | TCAATCCATGATGAGCCCACA | 27 |
| P4 | GTATAAGCTTCATGAGTGTCTGTAATGTTATG | 28 |
| P1 | GCCGCCACGTGCCGCCACGTGCCGCC | 29 |
| hpt-R | TACTTCTACACAGCCATCGGTCCA | 30 |
| hpt-F | AAAAAGCCTGAACTCACCGCGACGTCT | 31 |

Southern blot analysis: Total genomic DNA was isolated from glasshouse-grown material representing the indicated transgenic lines, together with control Jc-MD DNA, by Cetyltrimethyl ammonium bromide (CTAB) method. Genomic DNA was digested with restriction enzymes EcoRV and XbaI and separated on 0.8% agarose gels. The gels were processed and transferred to a nylon Hybond-N+ membrane (GE Biosciences, USA) following standard procedures (Sambrook et al., 1989). Membranes were hybridized with HPT and FAD2-1 ORF probes. The probes were labelled with [$\alpha$-$^{32}$P]-deoxycytidine triphosphate ([$\alpha$-$^{32}$P]-dCTP) by random prime synthesis using Amersham Rediprimer II Random Prime Labelling System (GE Biosciences, USA), following the manufacturer's protocol. Hybridization was performed overnight at 42° C. using the ULTRAHyb-Oligo hybridization buffer (Ambion, USA) and signals were detected by autoradiography.

Example 2

Isolation and Characterization of ω6 Oleate Desaturases Genes from *J. crucas*

The first step to generate high oleic acid *Jatropha* is to isolate gene(s) encoding putative microsomal ω6 oleate desaturase. To this end, two cDNAs possessing extensive similarity to extant FAD2 enzymes were isolated from a *J. curcas* seed cDNA library (Yin Z C et al. unpublished data). The two cDNAs encoded proteins of 383 and 387 amino acids that were 74% identical to each other and 77.3% and 72.1% identical to *Arabidopsis* FAD2, respectively. The cDNA with higher sequence identity to the FAD2 enzyme family was designated JcFAD2-1 and the other one was designated JcFAD2-2. JcFAD2-1 has identical amino acid sequences with AtFAD2 at its enzyme active centre in three conserved His-rich boxes (FIG. 2A), while JcFAD2-2 has a variation on a key residue Ala in active site His-rich box 3 (Thr in JcFAD2-2, FIG. 2A). The change of small hydrophobic Ala substituted with polar Thr could potentially alter FAD2-2 substrate specificity and enzyme activity due to the hydrophobic core environment crucial for its activity.

To investigate gene expression patterns of FAD2-1 and FAD2-2, RNA was extracted from all sets of seed development stages (3 weeks, 5 weeks, 7 weeks and 8 weeks after fertilization, corresponding to the early, middle, later and mature stages of *Jatropha* seed development stages) and used in reverse transcriptase (RT)-PCR reactions containing primers specific for each cDNA. As shown in FIG. 2B, the FAD2-1 gene is expressed in both seeds and vegetative tissues, while the FAD2-2 gene is expressed highly in seeds and not detectable in leaf. The expression pattern of these two FAD2 genes in *Jatropha* is very similar with those in the same Euphorbiaceae: FAD2 and FAH12 in castor bean (*Ricinus communis*), FAD2 and FAX in tung tree (*Aleurites fordii*). All the data above suggests that the JcFAD2-2 may function more like an unusual enzyme other than desaturase such as those of FADX and FAH12. Therefore, we chose FAD2-1 as our target for downregulation to produce a high oleic acid composition.

Example 3

β-Estradiol Induced Cre-Lox Recombination Marker Free System in *Jatropha*

Increasing biosafety concerns for genetically modified crops will definitely hinder its commercialization and have led to greater demands for applying technologies allowing the production of transgenic plants without selectable (e.g., antibiotic resistance) markers.

To produce selectable marker free transgenic *Jatropha*, we tested a chemically inducible Cre/loxP-mediated site-specific recombination system, which was first developed by Zuo et al. (2001) in *Arabidopsis*. Instead of using GFP as a reporter, we selected to silence JcFAD2-1 to make high oleic acid and marker free transgenic *Jatropha*.

A transformation procedure similar to that described above was used to get hygromycin-resistance regeneration shoots. Once visible shoots came out, we transferred small shoots to marker free induction medium without hygromycin. After two weeks induction, these well-growing shoots were subsequently transferred into regeneration medium II but without hygromycin. The remaining procedures are same as the transformation procedure described above.

When chemically inducible Cre-lox mediated recombination and DNA excision happens, RNAi structure then can be directly driven by the foremost G10-90 in pX7 vector (see the diagram of FIG. 3A). As a result of the down regulation of JcFAD2-1, there will be a change of fatty acid profile. Therefore, we randomly selected 10 putative marker-free small shoots from the plates to extract the genomic DNA for genotyping analysis. Using one pair of primers consisting of a forward primer specific for the G10-90 promoter and a reverse primer specific for the FAD2-1, PCR analysis revealed the small fragment of expected size in 2 out of 10 regenerated shoots. Meanwhile, there is an amplification band of hygromycin-resistant gene (hpt) in #1-1, suggesting it's a chimera. On contrast, there is not any hpt gene PCR amplification bands in #1-2, suggesting it might be a pure marker-free transgenic Jatropha. In Arabidopsis, FAD2 encoded desaturase is responsible for the desaturation of 18:1-ACP to 18:2-ACP. We hypothesized that a reduction of expression of FAD2-1 after induction should block the conversion of 18:1-ACP to 18:2-ACP fatty acids. We further used fatty acid methyl ester (FAME)-Gas chromatographic (GC) to check their fatty acid profile in leaf. As predicated, there is higher oleic acid content in #1-1 and much higher level of oleic acid in #1-2 compared with regenerated shoots from WT Jatropha cotyledon (FIG. 3C) meanwhile the linoleic acid level was significantly reduced in the marker-free lines. Thus, we have shown that β-estradiol induced Cre-lox recombination system can be used to generate marker-free transgenic Jatropha. We confirmed the function of JcFAD2-1 on controlling the conversion of oleic acid to linoleic acid in Jatropha leaf by stable transformation.

Example 4

Molecular Analysis and Oil Composition of X7-FAD2-1 RNAi Lines

Figure 4:
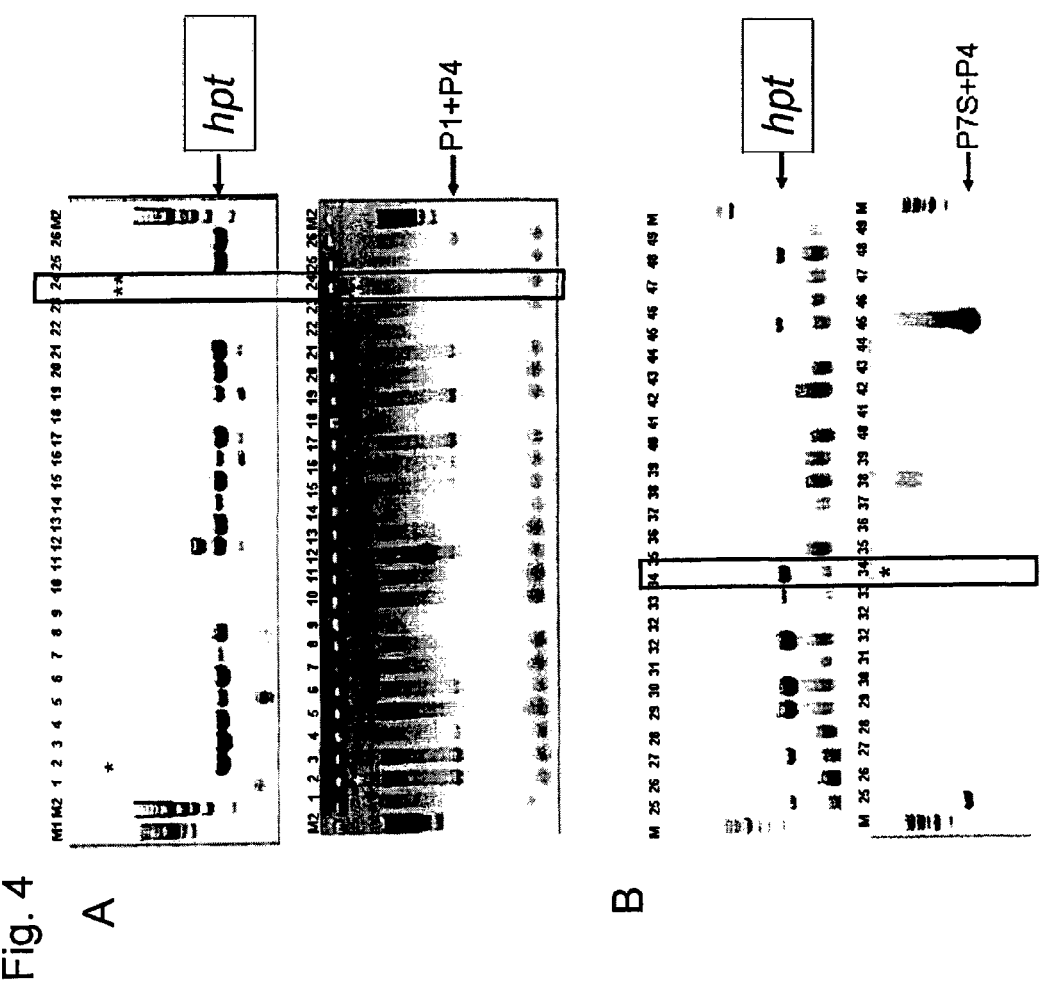
FIGS. 4A and 4B show genotyping of X7-JcFAD2-1 RNAi (A) and X8-JcFAD2-1 RNAi (B).
Figure 5:
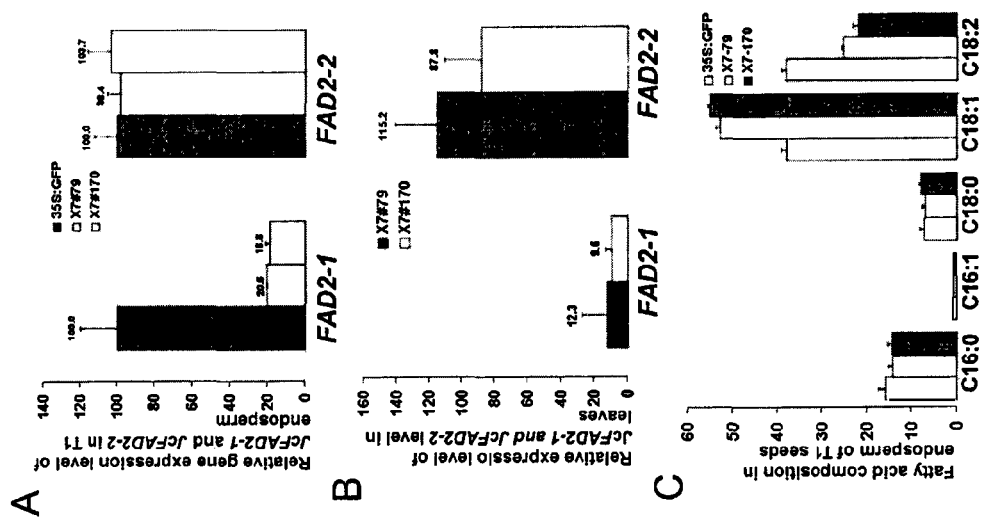
FIGS. 5A-5C show molecular and oil composition analysis of X7-FAD2-1 RNAi lines.

Using PCR-based genotyping, we identified 20 putative pure marker free X7-FAD2-1 RNAi lines (FIG. 4A) and transferred them to big pots in a greenhouse for further genetic and chemical analysis on seeds. We collected T1 seeds of these putative marker free events. Endosperm was separated carefully from embryo that we further germinated at hormone-free medium for T1 plants. Oleic acid of the two best lines, #79 and #170 was found to increase to 50%-60% on contrast of 36.7% in 35S:GFP endosperm (FIG. 4A). Meanwhile the linoleic acid was reduced to less than 25% from an original 41% in the control (FIG. 5C). But the change of oleic acid composition is moderate and not as dramatic as that found in medium and TRV-induced FAD2-1 RNAi Jatropha leaves (FIG. 3C and Ye et al., 2009a). We reasoned that the silencing effect is not as good in seeds due to the low intensity of G10-90 promoter activity. Our RNA data based on quantitative PCR further showed that there is still 20% JcFAD2-1 RNA in these two events (FIG. 5A). Further quantitative RT-PCR data proved this JcFAD2-1 knock down effect was gene-specific for there is no affect on the FAD2 homologue FAD2-2 expression in endosperm of these two lines.

We further germinated T1 embryo on ½ MS medium to generate T1 plants to check the JcFAD2-1 RNAi effect on its vegetative organs. We found a similar considerable reduction on JcFAD2-1 expression level (FIG. 5B).

Example 5

Higher Oleic Acid Transgenic Lines with Seed Specific Promoter

Figure 6:
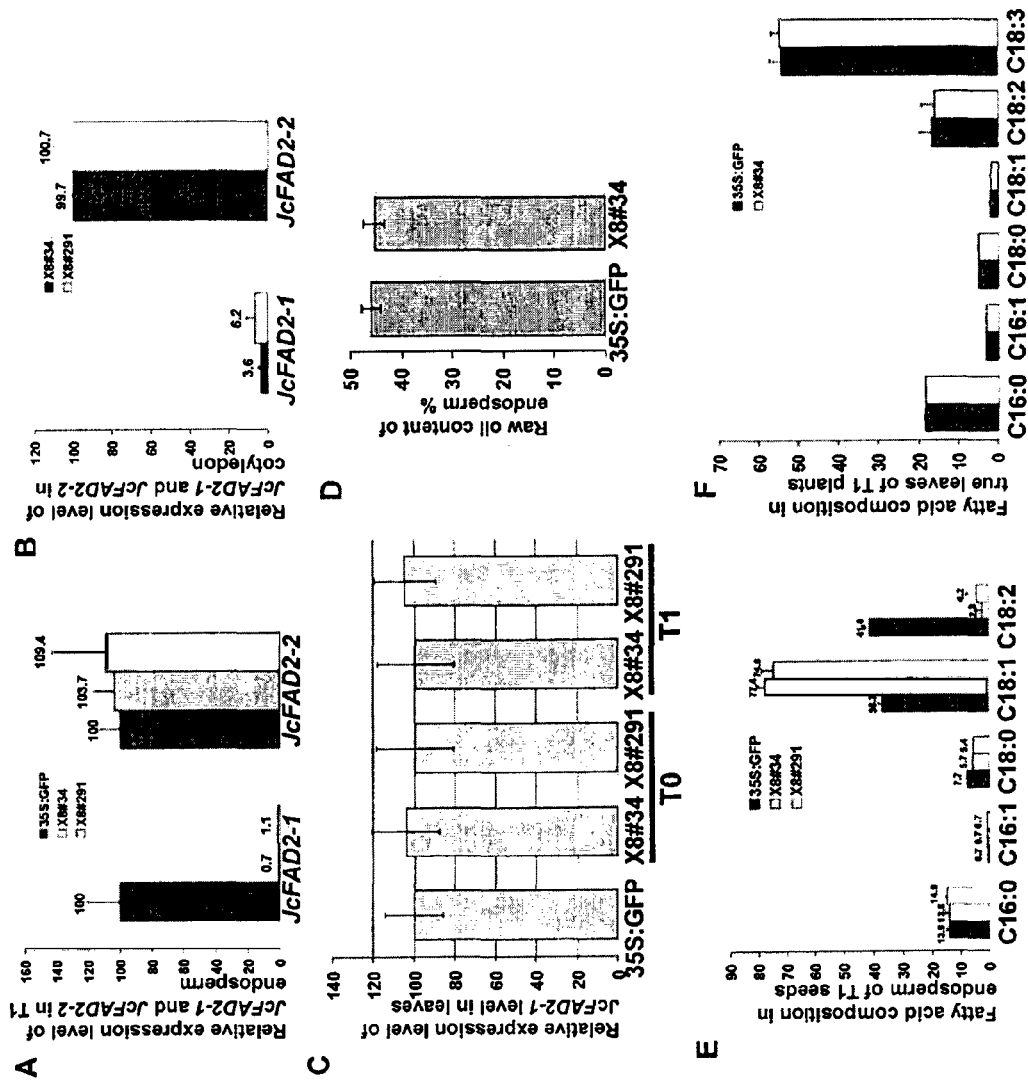
FIGS. 6A-6F show higher oleic acid transgenic lines with soybean 7S seed specific promoter.
Figure 7:
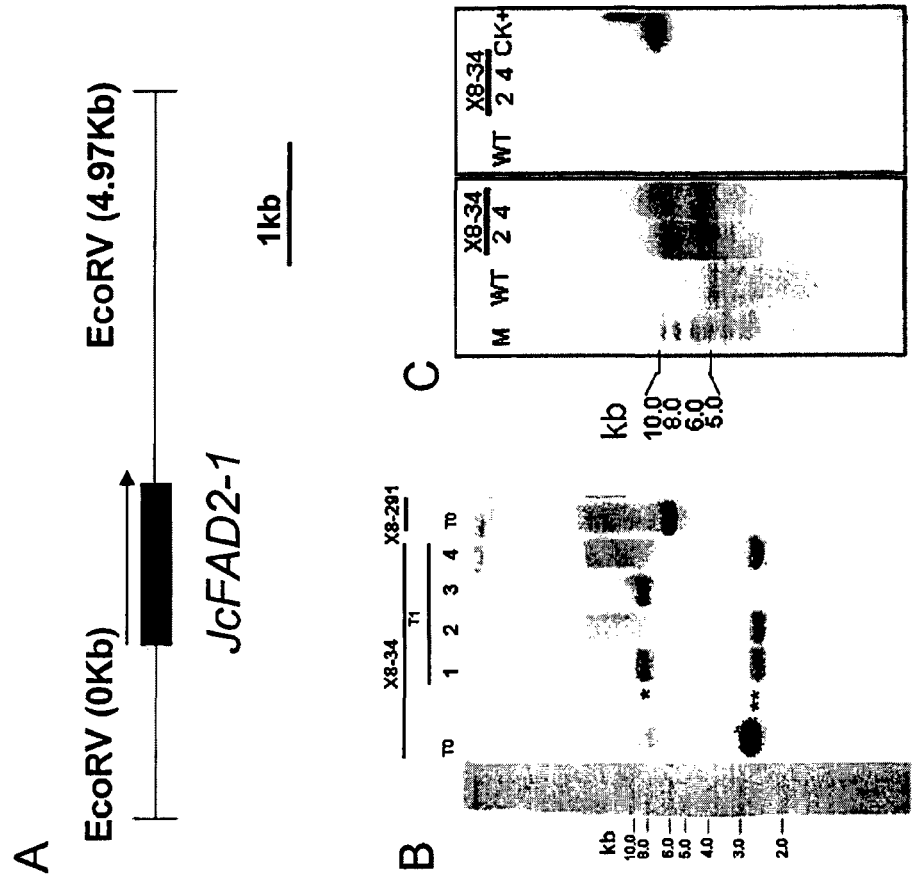
FIGS. 7A-7C show Southern blot analyses on primary and T1 plants from X8-FAD2-1 RNAi lines.

Because leaf oleic acid content plays a role in environmental adaptation of plants it is more desirable to specifically change seed oleic acid content with minimal effect on the same in vegetative organs. To this end, we replaced the G10-90 promoter in the pX7-FAD2-1 RNAi vector with the soybean (Glycine max) 7S seed storage protein promoter which displays seed-specific expression. The new vector with the soybean 7S promoter was named pX8-FAD2-1 RNAi (FIG. 3A). We generated 20 X8-FAD2-1 RNAi lines which were confirmed to be marker-free. RNA analysis showed that line #34 and #291 contained only 0.7% and 1.1% FAD2-1 transcript compared to 35S:GFP control in the endosperm (FIG. 6A). We found that the soybean 7S promoter was also active in Jatropha cotyledons as indicated by a much lower FAD2-1 RNA accumulation in T1 cotyledons (FIG. 6B). However, there was no significant change of FAD2-1 transcript levels in vegetative organs such as leaves (FIG. 6C). 100751 There was no obvious oil content difference between line #39 with control endosperm (FIG. 6D). GC analysis data further proved much higher oleic acid phenotypes in T1 endosperm of #34 and #291 with 77.4% and 74.7% oleic acid accumulated (FIG. 6E). The linoleic acid levels were reduced to less than 5% of total fatty acid in these lines. The total unsaturated fatty acids (oleic and linoleic) in control Jatropha endospems was estimated to be about 78-79%. In lines #34 and #291 almost all of the unsaturated fatty acids were stored as oleic acid. Moreover, the stearic acid level is also slightly reduced from 7.7% to 5.4-5.7%. There was no marked difference in C16 fatty acids composition between pX8-FAD2-1RNAi lines and control plants. Consistent with no changes on gene expression level, there is no statistic difference on fatty acid profile of true leaf (FIG. 6F). This data further confirmed seed specific high oleic acid in these lines.

Example 6

Southern Blot Analysis on Marker Free Lines X8#34

We performed a Southern blot analysis on line X8#34 to determine the complexity of the transgenic locus. There is only one XhoI site in pX8-FAD2-1RNAi vector (FIG. 3A). As we knew X8#34 T0 plant is a chimera partial marker-free (FIG. 4B). If there is only one copy of T-DNA insertion in Jatropha genome of #34, there will be two bands with around 5.7 kb size difference due to Cre-lox recombination event. Therefore total genomic DNA of T0 and T1 plants were digested with XhoI and probed with soybean 7S promoter. Southern blot data in FIG. 4A showed two bands with size difference around 5-6 kb in #34 T0 plants and segregated in T1 plants (1-4). It also suggested #34-2 and #34-4 are single copy and pure marker free, while #34-1 is a chimera and #34-3 without marker free. To analysis whether #34-2 and #34-4 are marker free and single copy, we further treated total genomic DNA of these two T1 plants with EcoRV and XbaI, which was expected to release a 5K-band from the JcFAD2-1 genomic locus as suggested by its genomic DNA sequence. An extra band was found in all of 4 plants of X8#34 and X8#291 (FIG. 4B) but was absent in Jc-MD WT control plant. We stripped the membrane and hybridized it with an hpt ORF probe and no signal was detected in any of the transgenic plants. These results confirmed that all these T1 plants were marker free.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Abdullah, R. et al. (2005). Immature embryo: A useful tool for oil palm (*Elaeis guineensis* Jacq.) genetic transformation studies. *Electronic Journal of Biotechnology* [online] vol. 8, no. 1 [Apr. 15, 2005). Available from: http colon// www dot ejbiotechnology dot info/content/vol8/issue1/full/1/index.html.

Carroll, A. and Somerville, C. (2008) Cellulosic Biofuels. *Annu. Rev. Plant Biol* 60:165-182.

Chiu, W. et al. (1996). Engineered GFP as a vital reporter in plants. *Current Biology* 6:325-330.

Chowdhury, M. K. U. et al. (1997). Evaluation of five promoters for use in transformation of oil palm (*Elaeis guineensis* Jacq.) *Plant Cell Reports* 16:277-281.

Christensen, A. H. and Quail, P. H, (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

De Wet, J. R. et al. (1987). Firefly luciferase gene: structure and expression in mammalian cells. *Mol Cell Biol* 7:725-737.

Durrett, T. P. et al. (2008). Plant triacylglycerols as feedstocks for the production of biofuels. *Plant J* 54:593-607.

Fairless, D. (2007). Biofuel: the little shrub that could—maybe. *Nature* 449:652-655.

Goff, S. A. et al. (1990). Transactivation of anthocyanin biosynthetic genes following transfer of B regulatory genes into maize tissues. *EMBO J* 9:2517-2522.

Graef, G. et al. (2009). A high-oleic-acid and low-palmitic-acid soybean: agronomic performance and evaluation as a feedstock for biodiesel. *Plant Biotechnol J* 7:411-421.

Guo, H. S. et al. (2003). A chemical-regulated inducible RNAi system in plants. *Plant J* 34:383-392.

Jefferson, R. A. et al. (1991). *Plant Molecular Biology Manual*, ed. Gelvin et al., Kluwer Academic Publishers, pp. 1-33.

Jones N, M. J. (1991) *Jatropha curcas—a multipurpose species for problematic sites*: World Bank, Asia Technical Dept., Agriculture Division, Washington, USA.

Last, D. I. et al. (1991). pEmu: an improved promoter for gene expression in cereal cells. *Theor Appl Genet* 81:581-588.

Lu, C. et al. (2011). New frontiers in oilseed biotechnology: meeting the global demand for vegetable oils for food, feed, biofuel, and industrial applications. *Curr Opin Biotechnol* 22:252-259.

Mao, H.-Z. et al. (2010). Genetic transformation of *Jatropha curcas*. International Published Application No. WO 2010/071608.

Masli, D. I. A. et al. (2009). Transformation of oil palm using *Agrobacterium tumefaciens*. *J Oil Palm Res* 21:643-652.

McElroy, D. et al. (1990). Isolation of an efficient actin promoter for use in rice transformation. *Plant Cell* 2:163-171.

Odell, J. T. et al. (1985). Identification of DNA sequences required for activity of the cauliflower mosaic virus 35S promoter. *Nature* 313:810-812.

Omidvar, V. et al. (2008). A transient assay to evaluate the expression of polyhydroxybutyrate genes regulated by oil palm mesocarp-specific promoter. *Plant Cell Rep* 27:1451-1459.

Parveez, G. K. A. et al. (2000). Transgenic oil palm: production and projection. *Biochemical Society Transactions* 28:969-972.

Parveez, G. K. A. (2008). Biolistic mediated production of transgenic oil palm. *Methods Mol Biol* 477:301-320.

Tat, M. E. et al. (2007) Exhaust emissions from an engine fueled with biodiesel from high-oleic soybeans. *J Am Oil Chem Soc* 84, 865-869.

Velten, J. et al. (1984). Isolation of a dual plant promoter fragment from the Ti plasmid of *Agrobacterium tumefaciens*. *EMBO J* 3:2723-2730.

Ye, J. et al. (2009a). Rapid analysis of *Jatropha curcas* gene functions by virus-induced gene silencing. *Plant Biotechnol J*, 7, 964-976.

Ye, J. et al. (2009b). A critical domain of the Cucumber mosaic virus 2b protein for RNA silencing suppressor activity. *FEBS Lett.*, 583, 101-106.

Yi, C. et al. (2010). Does epigenetic polymorphism contribute to phenotypic variances in *Jatropha curcas* L.? *BMC Plant Biol* 10:259.

Zuo, J. et al. (2001). Chemical-regulated, site-specific DNA excision in transgenic plants. *Nat Biotechnol* 19:157-161.

What is claimed is:

1. A nucleic acid construct comprising a plant operable promoter operatively linked to a nucleic acid encoding an RNAi nucleic acid that targets a native JcFAD2 gene and down regulates the native JcFAD2 gene, wherein the nucleic acid construct comprises the nucleotide sequence set forth in SEQ ID NO:32.

2. A transgenic plant cell, plant or plant seed comprising the nucleic acid construct of claim 1 stably integrated into its genome.

3. The transgenic plant cell, plant or plant seed of claim 2, wherein the plant is *Jatropha*.

* * * * *

SEQUENCE LISTING

<160> NUMBER OF SEQ ID NOS: 33

<210> SEQ ID NO 1
<211> LENGTH: 2298
<212> TYPE: DNA
<213> ORGANISM: Jatrohpa curcas
<220> FEATURE:
<221> NAME/KEY: CDS
<222> LOCATION: (1)..(1149)

<400> SEQUENCE: 1

| atg | ggt | gcc | ggt | ggc | aga | atg | tct | gtt | cct | cct | tcc | ccc | aag | aag | ttg | 48 |
| Met | Gly | Ala | Gly | Gly | Arg | Met | Ser | Val | Pro | Pro | Ser | Pro | Lys | Lys | Leu | |
| 1 | | | | 5 | | | | | 10 | | | | | 15 | | |

| gaa | gct | gag | gtc | ttg | aaa | cga | gtt | cca | tac | tcg | aag | cca | cca | ttc | aca | 96 |
| Glu | Ala | Glu | Val | Leu | Lys | Arg | Val | Pro | Tyr | Ser | Lys | Pro | Pro | Phe | Thr | |
| | | | 20 | | | | | 25 | | | | | 30 | | | |

| ctt | ggt | cag | gtc | aag | aaa | gct | atc | cca | cct | cat | tgt | ttc | cag | cgt | tct | 144 |
| Leu | Gly | Gln | Val | Lys | Lys | Ala | Ile | Pro | Pro | His | Cys | Phe | Gln | Arg | Ser | |
| | | | 35 | | | | | 40 | | | | | 45 | | | |

| gtt | ctc | cgc | tca | ttc | tcg | tat | gtt | gtt | tat | gac | ctg | acc | ctt | gcc | ttt | 192 |
| Val | Leu | Arg | Ser | Phe | Ser | Tyr | Val | Val | Tyr | Asp | Leu | Thr | Leu | Ala | Phe | |
| | 50 | | | | | 55 | | | | | 60 | | | | | |

| atc | ttt | tat | tat | gtt | gcc | acc | aat | tac | ttc | cac | ctc | ctt | cct | caa | ccc | 240 |
| Ile | Phe | Tyr | Tyr | Val | Ala | Thr | Asn | Tyr | Phe | His | Leu | Leu | Pro | Gln | Pro | |
| 65 | | | | | 70 | | | | | 75 | | | | | 80 | |

| ctc | tct | tat | gtg | gcc | tgg | cca | att | tac | tgg | tcc | ctc | caa | ggc | tgt | gtc | 288 |
| Leu | Ser | Tyr | Val | Ala | Trp | Pro | Ile | Tyr | Trp | Ser | Leu | Gln | Gly | Cys | Val | |
| | | | | 85 | | | | | 90 | | | | | 95 | | |

| ctc | act | ggc | att | tgg | gtt | ata | gca | cat | gag | tgt | ggg | cat | cat | gcc | ttt | 336 |
| Leu | Thr | Gly | Ile | Trp | Val | Ile | Ala | His | Glu | Cys | Gly | His | His | Ala | Phe | |
| | | | 100 | | | | | 105 | | | | | 110 | | | |

| agt | gac | tat | caa | tgg | ctt | gat | gac | ata | gtt | ggc | ctt | ctc | ctc | cat | tcc | 384 |
| Ser | Asp | Tyr | Gln | Trp | Leu | Asp | Asp | Ile | Val | Gly | Leu | Leu | Leu | His | Ser | |
| | | 115 | | | | | 120 | | | | | 125 | | | | |

| tgt | ctc | ctt | gtc | cct | tac | ttt | tca | tgg | aaa | cat | agc | cac | cgc | cgt | cat | 432 |
| Cys | Leu | Leu | Val | Pro | Tyr | Phe | Ser | Trp | Lys | His | Ser | His | Arg | Arg | His | |
| | 130 | | | | | 135 | | | | | 140 | | | | | |

| cac | tct | aac | acc | ggt | tcc | ctt | gag | cga | gat | gaa | gta | ttt | gtc | cct | aaa | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |

| aag | aaa | tcc | aac | atc | cgc | tgg | ttc | tcc | aaa | tac | ctt | aac | aac | cta | cca | 528 |
| Lys | Lys | Ser | Asn | Ile | Arg | Trp | Phe | Ser | Lys | Tyr | Leu | Asn | Asn | Leu | Pro | |
| | | | | 165 | | | | | 170 | | | | | 175 | | |

| ggc | cgc | cta | ttc | act | ctt | acc | ata | aca | ctt | gcc | ctt | ggc | tgg | ccg | cta | 576 |
| Gly | Arg | Leu | Phe | Thr | Leu | Thr | Ile | Thr | Leu | Ala | Leu | Gly | Trp | Pro | Leu | |
| | | | 180 | | | | | 185 | | | | | 190 | | | |

| tac | cta | gca | ttt | aat | gtt | tca | ggc | agg | cat | tat | gac | cga | ttt | gcc | tgt | 624 |
| Tyr | Leu | Ala | Phe | Asn | Val | Ser | Gly | Arg | His | Tyr | Asp | Arg | Phe | Ala | Cys | |
| | | 195 | | | | | 200 | | | | | 205 | | | | |

| cac | ttt | gac | cca | tat | ggc | cct | atc | tac | aat | gat | cgc | gag | cga | act | gag | 672 |
| His | Phe | Asp | Pro | Tyr | Gly | Pro | Ile | Tyr | Asn | Asp | Arg | Glu | Arg | Thr | Glu | |
| | 210 | | | | | 215 | | | | | 220 | | | | | |

| ata | ttc | att | tct | gat | gct | ggt | gtt | ctt | gct | gtc | act | tat | ggt | ctc | tac | 720 |
| Ile | Phe | Ile | Ser | Asp | Ala | Gly | Val | Leu | Ala | Val | Thr | Tyr | Gly | Leu | Tyr | |
| 225 | | | | | 230 | | | | | 235 | | | | | 240 | |

| cgt | ctt | gct | cta | gca | aag | ggc | ttt | gct | tgg | gtt | att | tgc | gtt | tat | gga | 768 |
| Arg | Leu | Ala | Leu | Ala | Lys | Gly | Phe | Ala | Trp | Val | Ile | Cys | Val | Tyr | Gly | |
| | | | | 245 | | | | | 250 | | | | | 255 | | |

| gta | cct | ttg | tta | gtg | gtg | aat | gca | ttt | ctt | gtt | atg | atc | aca | tat | ctg | 816 |
| Val | Pro | Leu | Leu | Val | Val | Asn | Ala | Phe | Leu | Val | Met | Ile | Thr | Tyr | Leu | |

```
                260             265             270
caa cat act cat cct tca ttg ccg cat tat gat tct tct gag tgg gat    864
Gln His Thr His Pro Ser Leu Pro His Tyr Asp Ser Ser Glu Trp Asp
        275                 280                 285 tgg ctg aga ggc gcg ctc gca act gtt gat aga gat tac gga atc ttg    912
Trp Leu Arg Gly Ala Leu Ala Thr Val Asp Arg Asp Tyr Gly Ile Leu
    290                 295                 300 aac aag gta ttc cat aac att aca gac act cat gta gct cac cat ttg    960
Asn Lys Val Phe His Asn Ile Thr Asp Thr His Val Ala His His Leu
305                 310                 315                 320 ttt tct aca atg cca cat tat cat gca atg gag gct aca aat gcc ata   1008
Phe Ser Thr Met Pro His Tyr His Ala Met Glu Ala Thr Asn Ala Ile
                325                 330                 335 aaa cca att ctg gga gaa tat tac caa ttc gac agg act cct ttc ttc   1056
Lys Pro Ile Leu Gly Glu Tyr Tyr Gln Phe Asp Arg Thr Pro Phe Phe
            340                 345                 350 aag gca atg tgg aga gag gca aaa gag tgc att tac gtt gaa cca gat   1104
Lys Ala Met Trp Arg Glu Ala Lys Glu Cys Ile Tyr Val Glu Pro Asp
        355                 360                 365 gat gct gat caa agc aga ggt gtg ttc tgg tac aaa aac aag ttt       1149
Asp Ala Asp Gln Ser Arg Gly Val Phe Trp Tyr Lys Asn Lys Phe
    370                 375                 380 atgggtgccg gtggcagaat gtctgttcct ccttccccca agaagttgga agctgaggtc    1209
ttgaaacgag ttccatactc gaagccacca ttcacacttg gtcaggtcaa gaaagctatc    1269
ccacctcatt gtttccagcg ttctgttctc cgctcattct cgtatgttgt ttatgacctg    1329
acccttgcct ttatcttta ttatgttgcc accaattact ccacctcct tcctcaaccc     1389
ctctcttatg tggcctggcc aatttactgg tccctccaag gctgtgtcct cactggcatt    1449
tgggttatag cacatgagtg tgggcatcat gcctttagtg actatcaatg gcttgatgac    1509
atagttggcc ttctcctcca ttcctgtctc cttgtccctt acttttcatg gaaacatagc    1569
caccgccgtc atcactctaa caccggttcc cttgagcgag atgaagtatt tgtccctaaa    1629
aagaaatcca acatccgctg gttctccaaa taccttaaca acctaccagg ccgcctattc    1689
actcttacca taacacttgc ccttggctgg ccgctatacc tagcatttaa tgtttcaggc    1749
aggcattatg accgatttgc ctgtcacttt gacccatatg ccctatctag caatgatcgc    1809
gagcgaactg agatattcat ttctgatgct ggtgttcttg ctgtcactta tggtctctac    1869
cgtcttgctc tagcaaaggg cttttgcttgg gttatttgcg tttatggagt acctttgtta    1929
gtggtgaatg catttcttgt tatgatcaca tatctgcaac atactcatcc ttcattgccg    1989
cattatgatt cttctgagtg ggattggctg agaggcgcgc tcgcaactgt tgatagagat    2049
tacggaatct tgaacaaggt attccataac attacagaca ctcatgtagc tcaccatttg    2109
ttttctacaa tgccacatta tcatgcaatg gaggctacaa atgccataaa accaattctg    2169
ggagaatatt accaattcga caggactcct ttcttcaagg caatgtggag agaggcaaaa    2229
gagtgcattt acgttgaacc agatgatgct gatcaaagca gaggtgtgtt ctggtacaaa    2289
aacaagttt                                                             2298
```

<210> SEQ ID NO 2
<211> LENGTH: 383
<212> TYPE: PRT
<213> ORGANISM: Jatrohpa curcas

<400> SEQUENCE: 2

Met Gly Ala Gly Gly Arg Met Ser Val Pro Pro Ser Pro Lys Lys Leu

```
              1               5                  10                 15
     Glu Ala Glu Val Leu Lys Arg Val Pro Tyr Ser Lys Pro Pro Phe Thr
                     20                  25                 30

Leu Gly Gln Val Lys Lys Ala Ile Pro Pro His Cys Phe Gln Arg Ser
                     35                  40                 45

Val Leu Arg Ser Phe Ser Tyr Val Val Tyr Asp Leu Thr Leu Ala Phe
                 50                  55                 60

Ile Phe Tyr Tyr Val Ala Thr Asn Tyr Phe His Leu Leu Pro Gln Pro
      65                  70                  75                 80

Leu Ser Tyr Val Ala Trp Pro Ile Tyr Trp Ser Leu Gln Gly Cys Val
                         85                  90                 95

Leu Thr Gly Ile Trp Val Ile Ala His Glu Cys Gly His His Ala Phe
                     100                 105                110

Ser Asp Tyr Gln Trp Leu Asp Asp Ile Val Gly Leu Leu Leu His Ser
                 115                 120                 125

Cys Leu Leu Val Pro Tyr Phe Ser Trp Lys His Ser His Arg Arg His
                 130                 135                 140

His Ser Asn Thr Gly Ser Leu Glu Arg Asp Glu Val Phe Val Pro Lys
     145                 150                 155                160

Lys Lys Ser Asn Ile Arg Trp Phe Ser Lys Tyr Leu Asn Asn Leu Pro
                     165                 170                 175

Gly Arg Leu Phe Thr Leu Thr Ile Thr Leu Ala Leu Gly Trp Pro Leu
                     180                 185                 190

Tyr Leu Ala Phe Asn Val Ser Gly Arg His Tyr Asp Arg Phe Ala Cys
                 195                 200                 205

His Phe Asp Pro Tyr Gly Pro Ile Tyr Asn Asp Arg Glu Arg Thr Glu
     210                 215                 220

Ile Phe Ile Ser Asp Ala Gly Val Leu Ala Val Thr Tyr Gly Leu Tyr
     225                 230                 235                 240

Arg Leu Ala Leu Ala Lys Gly Phe Ala Trp Val Ile Cys Val Tyr Gly
                     245                 250                 255

Val Pro Leu Leu Val Val Asn Ala Phe Leu Val Met Ile Thr Tyr Leu
                     260                 265                 270

Gln His Thr His Pro Ser Leu Pro His Tyr Asp Ser Ser Glu Trp Asp
                 275                 280                 285

Trp Leu Arg Gly Ala Leu Ala Thr Val Asp Arg Asp Tyr Gly Ile Leu
                 290                 295                 300

Asn Lys Val Phe His Asn Ile Thr Asp Thr His Val Ala His His Leu
     305                 310                 315                 320

Phe Ser Thr Met Pro His Tyr His Ala Met Glu Ala Thr Asn Ala Ile
                     325                 330                 335

Lys Pro Ile Leu Gly Glu Tyr Tyr Gln Phe Asp Arg Thr Pro Phe Phe
                     340                 345                 350

Lys Ala Met Trp Arg Glu Ala Lys Glu Cys Ile Tyr Val Glu Pro Asp
                     355                 360                 365

Asp Ala Asp Gln Ser Arg Gly Val Phe Trp Tyr Lys Asn Lys Phe
                     370                 375                 380

<210> SEQ ID NO 3
<211> LENGTH: 14365
<212> TYPE: DNA
<213> ORGANISM: Jatropha curcas

<400> SEQUENCE: 3
```

```
tggttgagag ttgcaatcca tttaatgcat gttcatgtca acttgaaata atggactaca      60
tattcatcca cttatacctα ctaataaaat aaaattttca cgataaaatt taattttaaa     120
tagcattgtt tgtctgtcac tattttaaca aagaactaag cagattagat agattttta      180 cattaatatt atttcaaaa ttgccaaatt agaaaaaact ttttatataa aaagagcatt      240
taaaatataa aattttctta tataaaaaaa atgagagagt atcatacgat gaatttttta     300
aagttttttt ataatgaaaa cataattcga tactggtaat taattattta acatatatgt     360
atttttttat ttattataaa taaataaatt acatatatgt gataaataaa ttaacatgta     420
ccaaaatttt gatgatgatc aaaataatat actccaaaaa tatgaggatc tcatctacag     480
attgataatt acagctagat aatcttgagc catccattaa ataatagatt gtttttaaaa     540
ttattattaa tagtatgaaa aagtgcacaa gatagatttt aaatttaaa tatttcagaa      600 ttttttttatc aaaattcaga attaaattat atattgtacc taatattaat ataatatagc    660
attatttaga ataacgcat gattgatgga tagatcacat caagtgacaa agaaaaatag      720
aataagaaga tcaatgagta tatgcagccg tatattcata tattatatta ttttttgctca    780 caacttacca actaattata aatcaaatag attcttaaat gcatatattt cacaagagaa     840
ttgtttttat tatttaatt cacgtgtatg tgcaaacacg tgaaatatca tatttcatca     900
aatcaacgtt tatttgatat aagtcatttt gcaataaatg cacacagtag attttggatt     960 catgacgaa tggatgtagc cgtgcagact ttgaattctt cctcataaaa aattattatc      1020
aatttattaa atattattta aaaaagaaag ctaccctata tgtattttt aaatattaaa     1080 tttaaattaa taaattaa ttttttcatta aaaatttat aagctatcaa taagacaaaa      1140
caaatgacac attctatata ttggtatgat tgcaacaagt attattaagt agcttacgac     1200
tctacacaaa aacattttca atttcatt ttattataat tgcatgatat ttctacattt      1260
tgacaagtat gccaaaagat aactaacaaa ttaattaata tatgttaccct tattttttac    1320 tatccaattg gaaattttta gaattaaat ttcattttta tgtttttaat ttgtaattaa      1380
atcagagaca ttaaaagtac caatatttta attggcaaca ataaaatttc tatatgtcaa     1440 cttaatttttg gttatatttc attatcactc gatcttacaa caagttaagt atattaaaaa    1500
tatcttgttt tgctcaataa ggatctatta cttaaagtga atttttgattt gtttgaatac    1560 ctagaaaaaa gttaattgac ctccaataag cggtgagctt gattaaggaa ttttgaaaat     1620
gccttttaaa gagtggtagt agctttcgag tcaacttcca tttccttatc cgcacaagct     1680
ttgcctgctc aactcaactt acacgaagct tccttcacgg catcaattac tgaccgccgc     1740
tttgtttgga tgaagatagg gatcgtcaaa ttaaggtata atagagcatg ctatgaaaaa     1800
gtatagtaaa tgttttttg gaaaagtat agtaaatgat ggtttaataa tattattttg      1860
tttgattgaa tggtaagaga aagtaatgtt taatataaag attacgaaaa tattcttatc     1920
gtgaaagatt tataaatata attatgaata atttttgaaaa ttttaagttt tttaaatatg    1980
cttacacttc aaataatttt caaaaaacta tcatctccct caaagtatta ccccacacga     2040
ctaaataaca tctattcatc caaacaatca ttaagatgag atatatatgt actcgatgca    2100 tgtatatatgt gtcgaaatag aaagacgtgt aagaattaga ataaaacat attttggccc    2160 cttaaccttta acaattttgt caatttgccc cttttttttt ttttgaaaca ttttctttc    2220 gcaatctcaa acttcatcta tgaggtacac gcgccccttt tgatcgaacc ttgatggagc    2280
gggcaaaaag tatacaaaat gcacgagtga gacggtaagt aatcgtaacc cttttgatcg     2340
aaccttgatg gagcgggcaa aaagtacaca aaatacgcgc gtgaggcagt aagtaatcgt    2400
```

```
aacccattaa aacgacaccg tatgaagtac ttcaatatgc ctaaagcaat attaagacgg   2460
ttccgttaca cttataaacc tcatcttttc ccacaatgta aataaagaga atcagtgaat   2520
ttttgacaaa aaaccgcttg aaatcgaatt tcctctagaa attgagcgga gaagaaatgt   2580
taaagaattg gaaaatttga aattaattag tggctgaagg ggtaaaagat catctccaca   2640
cgaaaagaac agaaacgata ataggggaag atacgggag gtataaagaa gaagtatctt   2700
tggatatgaa atctcaaaac tgaaaatgtt tcaaaaatgg taaagttaag ggaccaaaat   2760
atatattcag cctaagaatt tgagatgaca tatcccaaa ggctaacact ttccttccat    2820
tattagcttt aagaaatatt atcgatatcg atatcgatta ttatcaatta cgaccaattc   2880
aaccaaaaag attctaaata ttgtagattt taatgcttga aatttgaaac atgtaagctc   2940 caatttttaaa ataatagcat ataattgtta aaaaaagtat attaatgctt gacttggtga  3000
tatatatttg tcatattcat gtcatatatc aaatagatgg aataaacgca tgcattgcac   3060
atggaaggag aagcacaaaa cacgttttgc aagtgcagaa gcttccatta ttaatattat   3120
taggattagg attaggatta gctggggatg atgacaggat tgtatggaca ttcatgtcat   3180
ggcattaaat acaacaccaa cattagctac gtacaaccaa ggtcggctat atttttaggt   3240
acaatatctg aatattaata ttattatcag aataccatct ctgaaatttg gtctaaatat   3300
aaaaactaag ggcatatatg tataattaat tgcccttatt ttcagaaaaa aaatatataa   3360
atagaaacat aaataaactc aatcggataa agtaacactg tgattgtaaa caaaattaaa   3420
ccagatataa taacaaaaca tgtaacagtt aaaaaatttt aaaaagataa tgctaatttt   3480
gaaactttaa tgaaagaaaa aaaaaaaaaa aacgcatacc atgttaagaa tgtaagggat   3540
taatactttt tttatttgca acatagctgg gtttcggttc agaaccgaaa atagcttttc   3600
ctttaaattg aattaaactg aagttagttc aaaaattgaa ccaaatcgat cagttcattt   3660
ggtacatatc gatttgattt tactcaaaaa ataaatgttc tacaataatt gatataaaaa   3720
ttgaaattat aaatgattga aaaccgaagt cgaaaatcaa ataatcgaac taaaaataaa   3780
aataaattca atttggttcg gtgttcgatt cttttccaaag gttgctcacc cctgtttgca   3840
cacatgtttc ttcgtttggg atgagaagta gtatttagat atatattttt tacatatata   3900
tatatataca cacatataag atctccaatg gattggaaaa atatataagc tatatagcag   3960 gataacctttt ttcattgaat tatattcagt aattcggtga taacttttgt gatggatgat  4020
acttgaactt gaggtttttg gctcttcata tcttctacaa aatatgaaaa agtcaaccag   4080
atcataccct gcgatattta ggtaatttttc ctaataataa caacttcaaa ttacatattt   4140 cattttttt taatttgata tgtattttttt aaaaataaaa tattttttg aactcgcttt    4200 gtacattttt tttaaaccct tgatcttata tagaaattat aatatatgta aatatttatc   4260 aacatttttta ttttaagcat taaaaagtaa ttatttttatt tacagcattt cattatgctt  4320
tccatgtttc ctaaaaaata agatataaat aacagaagtc agttacaagg aaatgattca   4380
tataaatata caatgacagg tgaattgatt ttcaaaataa aaagttaatg tggcaaacat   4440 aattttttctt caacacaaca cttatttctt gaaaatgact cttttctcag gttaattatt   4500
tattatttat tgagatacat gggaaatata ccctagagat atagggggga cctggtccct   4560
tcccctagct ctaaagtcc ttccaatttt tattttataa aataaaataa agcatattttt   4620 aagtgtacca aaaattattt cacaatagtt tatcatatat aatataccat tctcattgac    4680
cattcatcct atataataaa ataatatata taactagaaa aaatttttaac taataattttt  4740
```

```
aaaatttaaa accaaataat aattcaacat tttataaatt taaattagat ggttgatttc    4800
aaattgaaag ctcaaattta agttcctcca acacacaaat catattaaaa acatataaaa    4860
ataagaacac tttttttttt aatgaacaat atattttttac tataaaaaaa agaacaaata   4920 tatttttta tcaaaaaatc cagttatttt ccgaatttat caaaaacatc tgattttttt    4980
tctaaaacca agctaacatt ataatcgaac caaacagcta tccgattcgt gatttaaccg    5040
atcaaattga ctagtccggc ttgattccaa aaatattgga tataattatg gctttcttaa    5100
cttttgcttc catctctttt tgagtatttt tgtttaagaa aaaacatttt aattatggac    5160
gccataatta tttattgaag atggagggat aaattgcttt aaaaatcaat agttagattg    5220
tttttttttt ttacagaaaa atcacaaaaa tgaaaattta gtgatattat aattattttt    5280
caaaaataag aactaaagtg ttaataagat aaaatttaag taccacatat tttcccaaaa    5340
aatatatata gagcaataat atctggagga gataagaaat cacaaaagta caataattac    5400
aaaaatatac ggaaatgagt ccgttaactt taataaaaat ataagataaa aataataatt    5460
cgtgaaagta aaattaaatg tatggaaatt agccgtgcgt taaacagtgt catagagaaa    5520
aaaaatataa aataacata atttattttt aaaaatatag ggtacaaaat catatatttt     5580
accaaactat aagagtaaaa tagtaatttt cccttaatat aaaccaggtt aaaggaaaga    5640
gaggatacat gagcaaggaa agtcgcgatt tttaactaag ggacagaccg cggaaagtcc    5700
aaacaacatg ttgacatatg gtgggcccca caccactgta tagggtagga gcgcaagctt    5760
aagtaccgcc cacttctttg catgcttttg agcagaggcc ggtatccttc tacggccata    5820
gccacacaga gagacgcagg aggcggatag ctttcgattc tttcaggtac actttttttt    5880 tttttttgt tgcgtttctt tgtcattttc ctttatgttc ttattatggc cggttcgaat      5940
ttttcgcatt cgcatttggg ttttcgtttt ccattccatc aaactctgct ctgtaatgta    6000
aattagatcc aggcgaaaac cagcaacaga tatgttagat cttcctttt cgatttaga     6060 tttgattttt tgatttttt ttgaattttt cttgaatatt gggaagagag ttgtcgcttt    6120
ggttggacat tttaagtttt ccatattgaa atcaattttcc atattgaagc cttcttttta   6180
aaaaaatttt ttttcttgaa tattgtttag agattatcgg tttggttcga cattaagttt    6240
ccatattgaa tctatttcaa atttgttta ttttttcttt agtattgttt gggtttatta     6300
accttttgcc tgtttgttac gaaagaaaaa aaaaacttt gctctgttct cgaggctctc     6360
tctgtttaat cgatccgtgt atctgtcgac tgtcgtcctt ttcttgaagc cggtcacgtg    6420
atctccgctc tatatgcttt cacatttagt tgtattccat attagttttt agcatgatac    6480 ttccttttt tttttattat ttcttagttt tgtttaattt ttcttcattt acactgttgt     6540
ttgtatctgt ttggccttat ttttcaatta gaatactctg aaagcgattt tgttttgttg    6600
ttaacaaact ttgtgcttaa ttgcttataa aaaaaaataa taggaaaaaa gagaacccat    6660
atatagcata ttggcatctt gattctaata cttaccccta ctatttgtta aatgttcttg    6720
tgtacttcgt tgctttgggt tcctgattgg tttcttttgt tttttctttt ttatattgta    6780
ggaattcatc ttttcaatta ggctagctct acgaaacact aattaagcta aaaaaaatat    6840
attaatcggt tttgtaaatg aaagtaaacc tcctcttttt aataaaatat gagaaagtaa    6900 aagactttc ctttgttttt ttttttggttc attaatactt ttcctttcaa tatactatta    6960
ctatctaatc gaacatcatt tgcggtggga ttgtgaacag agggaaaaaa aaagtattac    7020
atgtatgata attaattatt ttgaaaagtt tactgtcaaa atatgtaact atacctaaca    7080
atttgccact cgctagcaat cattcccttc accagaattc gtacggtcaa aatagttggc    7140
```

```
tttggcccct caatagctgt gactgtacaa ctaggtcatt gtatagggg tatgaatcat      7200 ttgttagcgt cgaacagcag ctggtcagtg gagtgggacc catttctgtt ttgttgtgta      7260
gaacccacca catgcaagtc tctcatttat tggaatcgag ggaggcggtc attgtcaaag      7320
atgatttttg gtctgttaat ttaagtggtt cgccgtgtgc tagcgttcta gtttattggt      7380
ggttgatgtc aggtagtagt taatgaattg aaggttggcc actttggtaa gaccagtttt      7440
ctcgccgaaa tctttttttt ttttctttt tcctttcttt ttcttttttta agagaagatg      7500 caccaaaagc cctgggatgc gttatagtgt gcagtataag tcattagtgc gctaaccata      7560
tgaagaaata ggggaaatta tttggtacat ccagtgaatc catttctcat atttaggtga      7620
aatcatttag ctataatttc aggtggtact atttctgcag tcacttaata atttccccag      7680
aatagagatg aagatttgat tgtttcttg tacctgctcc accctaatct gtaacaatgg      7740
attatgtaaa cattttcgtt taatgattgt cactctccag gtcattgcat gggtcatttg      7800
gattgtatat caaataatta aggaaggttc ataagtagga tatttttttt ttgacattat      7860
cataagtagg atatttaatt ttttaggtg tatattttga atcaaacatc taatttatac      7920
aattagatct gacttgacat gctgtcaatc gcatgtcaga caatgtggtc atatagcata      7980
tatcatggct cattagtatc cattgagtga ggttcctttc ttgatgcaca tggcttggtt      8040
accccaccac aactcgtaga atggggttca agtagtttgg acaatccaaa tttggttatt      8100
cttgaataat tgcttatagt gaccacaaaa taccatagta tggaattatg gatgtagtgt      8160
tggcttcttg tctttattga tgagaccaca tcctcatctt ttgtggactc agttggatct      8220
tattttcttg cggtataaat ctttaatgcc ttttgaggtg gattttaagt ttcctgtaca      8280
gatgtgttag attttgtcca ttgaaaaaaa taaattgatg tttaccaaaa gaaagaattt      8340
agttcacggt aaagcaataa ttgcactcct tatttttac agtaagtgct ttaaatagac      8400
cccagaatgt gagtcaacac ctaattataa attattacca ttgcatctac tagcacttta      8460
atgtcaattc aagaaccttt tatttgttgc gatatatatg ttcttgttcc catggatatc      8520
attagtcatt agtatcactg tataaaatat ttagtgctac tataaccata taaggcacaa      8580
atgactaaca gcaagaaaaa taaaacttt tcatgtccaa ctgtttttt ttttttttt      8640 tttggtgata atagtcaatc tttactgcat attctgtgat tggtcttgta ttacatggga      8700
catgaggatg tctactgcta cttaacgag cacatgggct caccctctgct ttccactttt      8760 cccatttttg catttgcttc taaacaaatt ataattagct tctctgagta aaggtttcac      8820
tgttgttttg ctatatgata tactcttgtg acaagggtaa ttgaacattt ggatcgtgtt      8880
ccattaagaa caagtacaat aagaaaagaa atccaatgta ggaggttgag gggagacctg      8940
acaacttctt tccttaaaag ttttggtgt atctgcaaaa acttagcaag gagaaggtcc      9000
agcattaaag tatgtgatta gtctgttaaa atgtttaata taatgtcttg gtcagatgca      9060
cagagctgtt ttatcaatgg attatatata tatatatata tatatatata tatatatata      9120
tatatatata tatatatatt gtgacaagga ttggcaacag atcgattgac cctgattact      9180
ctccacttgt catccaaagc ctagctaagc cttaaccttt acctagggc ttgaggttta      9240 gcctgctaaa tctccgactg gggtttctgt ttccatggga tcccgagcag tctttgagtc      9300
aattagcagg cagtcaattt catttgcaat tgtatggttt tacagatggt ggctcttgtt      9360
tggtcaaact cagcagaagt gggagaatgc ctatgatgct tgtacaaggg atttcttgct      9420
gattaagacg gtctgatact tggtttacca accacgcagt ataccatatc tgacactata      9480
```

```
atttttgtgc caatattaaa ccacgcagta tataccatat ctgacactat aattttttgtg    9540
ccaatatttt aatcggcatc tgtttctgat tttagtgctt gatttgctat tctagcctta    9600
caccatttaa aaagtaccta taattggtgt aatgctctca tcttcactca gtaaaagtga    9660
ttgacagatc catttatgca gcaaatgctg tgtgtttctt tcatatcttg atgcctgtgt    9720
aaggaactct ctatcattgt gatgcctgta ggattaagtg gattttttc tttaagttga     9780
attttggcat gttttggttg aagttgaaat tttacatgtt ttaagctcat tactgtgcga    9840
agtttgattg ttgatgtggt aatttgtcac tgggagacat atctgctcct aaactgccaa    9900
ttattaaggg aattgatttt atacatatac catcatatag gaactcaaca tctacttaat    9960
tttttcaggt tgtgcaacaa tgggtgccgg tggcagaatg tctgttcctc cttcccccaa   10020
gaagttggaa gctgaggtct tgaaacgagt tccatactcg aagccaccat tcacacttgg   10080
tcaggtcaag aaagctatcc cacctcattg tttccagcgt tctgttctcc gctcattctc   10140
gtatgttgtt tatgacctga cccttgcctt tatcttttat tatgttgcca ccaattactt   10200
ccacctcctt cctcaacccc tctcttatgt ggcctggcca atttactggt ccctccaagg   10260
ctgtgtcctc actggcattt gggttatagc acatgagtgt gggcatcatg cctttagtga   10320
ctatcaatgg cttgatgaca tagttggcct tctcctccat tcctgtctcc ttgtcccta    10380
cttttcatgg aaacatagcc accgccgtca tcactctaac accggttccc ttgagcgaga   10440
tgaagtattt gtccctaaaa agaaatccaa catccgctgg ttctccaaat accttaacaa   10500
cctaccaggc cgcctattca ctcttaccat aacacttgcc cttggctggc cgctatacct   10560
agcatttaat gtttcaggca ggcattatga ccgatttgcc tgtcactttg acccatatgg   10620
ccctatctac aatgatcgcg agcgaactga gatattcatt tctgatgctg gtgttcttgc   10680
tgtcacttat ggtctctacc gtcttgctct agcaaagggc tttgcttggg ttatttgcgt   10740
ttatggagta cctttgttag tggtgaatgc atttcttgtt atgatcacat atctgcaaca   10800
tactcatcct tcattgccgc attatgattc ttctgagtgg gattggctga gaggcgcgct   10860
cgcaactgtt gatagagatt acggaatctt gaacaaggta ttccataaca ttacagacac   10920
tcatgtagct caccatttgt tttctacaat gccacattat catgcaatgg aggctacaaa   10980
tgccataaaa ccaattctgg gagaatatta ccaattcgac aggactcctt tcttcaaggc   11040
aatgtgggaga gaggcaaaag agtgcattta cgttgaacca gatgatgctg atcaaagcag   11100
aggtgtgttc tggtacaaaa acaagttttg attgttagaa aaatttgcaa aatgaaggtg   11160
ttgcaagttc tggactactt gttaggaatt tggatttgct ttctcagtaa tttaggcagt   11220
tcaattgtgt tgaattaagt taaaatctta tatgcactta ttttggaata attttatcca   11280
cccaggtaga aacaatatga acaatctaag tttatgttct ataatgaatg taagacttgt   11340
ttcttgagcc aaaatgaaaa tctatgatga ggtttataaa aattcaaatt cagatggacc   11400
acgaaaggtg ctcaatccaa ttgaacctat gagaatatac ttagatttga tttagttagg   11460
tgttgactga tagttcggtt tattaaaatt aacaagccaa agccaaatca aattctcaaa   11520
ttttaaagaa ttataataat tttacttttgg gttttagggc tgttcaatta taaagacccc   11580
tatatccccc gcaaaacaaa agcaagaata ataagagaat ttgcaggcag tctcctcctc   11640
aaccacaaag atggatgttg aagtcagctg atccgaccac ttacatccta tcctcactaa   11700
cggaattgca atagacattt gatatgggcc cagcccaact cgatttcgg cctttctcat    11760
ctcatccaat tttctaccat tgttgtgag aaagctatga attttaacta atgatagaat    11820
ttgtattatg gacatcgaca taaccctatt aaaacttttg tttattcata atttattaag   11880
```

```
gaaagtatct acatttatct ctaccataat tagataatag actgatttgt aaagtatatc   11940
aattactctt ataaatagct taatgatagg ctgtagttta tgagttaatt acgttattta   12000
tccgtataaa ttgaggtgtg cagattaatg aaaacatatc ttcccaccaa catcttcttc   12060
atcctatttt agataattaa tgatttggtg gctaattact aattagtcaa gaatcctatc   12120
tactatgtcc cttcacatac acacaatcaa attatactcc ccattaaaaa ttaaattaaa   12180
ttaattatcc aacaattaat taacctctca ttttcattgt ctaagcacga ggattgaaaa   12240
gtgttaacaa ggtatagtta attaagatac tagctacttg ctttgctttg gataatgacc   12300
cttatgtgat cattacaatg tacttcaccc attactcact aagatataat attgggaatg   12360
gagtaataaa aattcaataa atgacacaaa aaaaaaaaaa aatttgcaat tataccaaaa   12420
tcttttgata atatattgtt ttaccttgga tttcaaatat atatatatac ttatatattc   12480
caaataaaag aatagcaccc ttttctcttc ttgatggctt tggcactatg caatatatca   12540
ttttaatttt gaccaaatag gcacaattaa aattaatttc tgaaattata gataaaataa   12600
tatatttcaa aagaattagg tgtaattata atctttcaaa aagatttgaa ttttttatat   12660
tattagtcat tttactataa ggttaaatgc atgtagactg gcaataacaa agatcaataa   12720
agaaaaaaca aattgggata taggaatatc gtttgtagaa tttgttttaa caaggtaatt   12780
agtgattaat ctatcggtaa ttattttttct cttctaacag caagaattga atgttatgta   12840
tggaggggcg gttaaaaaga acatcgactt gctaagtcaa ggtcccccac cttcttactt   12900
ttcaatcagt ttcaattata catacatata tccaaccatc aaaattaaaa ttaaatttaa   12960
ttacacatca agtttctacc ttcttccaga aaataaataa aatagagtaa gatttttttt   13020
tttcccaata agatgtgttt ttttatatat atataattat aaatacatta taaagtacat   13080
cggctcattt gaagaattca acccaataaa aatagaaaat aagatatatt gaagagtaat   13140
tactcatctc aaaaaaaaaa aaaaaaatcc tattttaaaa tggaatttcg aaatattgaa   13200
gagagtagaa agaaaatgaa aagcactcgt aaagatttgc aacaatattc caagaatcca   13260
aatacggtgt gagtcgtgca ggagaaccaa ccacgtcaaa cagtgggggtc cactggttct   13320 ctttagttgt tggttggctg gctggctgac tcccggtaag ggaatccgtg gctgcacgct   13380
ctttgccacg tggatttcag ttttggcact gagagtgggc cggcacgaga ctcgtatgcg   13440
ctctctgagt ctgttgctga cgcgctaaac catttgccgt cagatatcat ttcatgcctt   13500
cacgtgcaca tctcacggtt actattctcc tgccaagtgc caactgcaat tatgacccttt   13560 tcaatatgcc caaatctcat ctcaactgag tttcattttc tgaggagggt cattggatcc   13620
aaaatataaa aagccaatga gtacggaaac gaagaagaaa tatttgttgc cttcttcttg   13680
acagtatata tatatatata tgaaaaacac tattaattga ttaatattaa tcaaaggaga   13740
aattgatttt gaaatccatt tgcactcttt gaaagctcca acagtgacag taagcagtgg   13800
caattaattg tacaaccggc agattagtcc ttaattatag tagctaatta aaatacgaaa   13860
gcaagagaca aaggaatact ttcaagccaa ttaaggcttc gtttgtttat gtaaaataat   13920
ttgtaacgaa aatatttttt ataatttttt attatttgag gcgctcagaa aaataagtca   13980
acgaagaata ttttcatggt caaaggaaaa ttaagtcatt ttttaagaaa aataacttct   14040
cattttcgag agaaaaatat tttgcggaca ttgacaaacc ttataaatcc atgcttttta   14100
atttattaat catcataatt actaccgcca atcactattt accactaacc accactttta   14160
gttactacca ccggcgactt tcataattta tatatttttt tcattctttt catatttaac   14220
```

```
aataaaattt ttaaattata aaaatcttac tataattaat attttttatg gtcttatgag    14280
ataaaagctt taatatttt aactaatttt gaatgttaca acaaaacaac agaaaataag    14340
tcatttggac aatattttc agcaa                                          14365
```

<210> SEQ ID NO 4
<211> LENGTH: 1203
<212> TYPE: DNA
<213> ORGANISM: Jatropha curcas
<220> FEATURE:
<221> NAME/KEY: CDS
<222> LOCATION: (40)..(1200)

<400> SEQUENCE: 4

```
atgtttaata tgaatctgc agagaagctt aacagaaca atg gga gcc ggt ggc         54
                                           Met Gly Ala Gly Gly
                                             1               5 caa aaa act gct gtc ctc gtc agc agt aag ttc aag gaa atg gaa acc      102
Gln Lys Thr Ala Val Leu Val Ser Ser Lys Phe Lys Glu Met Glu Thr
             10                  15                  20 aac aga cgc ctg aag cga gtt cca cac aca aaa cct cca ttc act ctt     150
Asn Arg Arg Leu Lys Arg Val Pro His Thr Lys Pro Pro Phe Thr Leu
         25                  30                  35 ggc caa atc aaa caa gcc atc cca tcc cat tgc ttt aaa cgc tcc ctt     198
Gly Gln Ile Lys Gln Ala Ile Pro Ser His Cys Phe Lys Arg Ser Leu
     40                  45                  50 ctc cgc tct ttc tcc tac ctt gtt tat gac ctc tct tta agc tct ctc     246
Leu Arg Ser Phe Ser Tyr Leu Val Tyr Asp Leu Ser Leu Ser Ser Leu
 55                  60                  65 ttc tac tac att gcc gct agc tac ttc cat ctt ctc cct tct ccg atc     294
Phe Tyr Tyr Ile Ala Ala Ser Tyr Phe His Leu Leu Pro Ser Pro Ile
 70                  75                  80                  85 tcc tac att gct tgg ccc atc tac tgg act ctc cag ggc tgc act ctc     342
Ser Tyr Ile Ala Trp Pro Ile Tyr Trp Thr Leu Gln Gly Cys Thr Leu
                 90                  95                 100 act ggt gtt tgg gtc att gct cat gaa tgc ggc cac cat gct ttt agt     390
Thr Gly Val Trp Val Ile Ala His Glu Cys Gly His His Ala Phe Ser
            105                 110                 115 gac tat caa tgg gtt gat gac act gtt ggc cta att ctc cac tct tca     438
Asp Tyr Gln Trp Val Asp Asp Thr Val Gly Leu Ile Leu His Ser Ser
        120                 125                 130 ctt ctt gtt cct tat ttt tca tgg aaa att agc cat cgt cgc cat cac     486
Leu Leu Val Pro Tyr Phe Ser Trp Lys Ile Ser His Arg Arg His His
    135                 140                 145 tcc aac acc ggt tcc att gaa cgt gat gag gtc ttt gtc ccc aaa ttc     534
Ser Asn Thr Gly Ser Ile Glu Arg Asp Glu Val Phe Val Pro Lys Phe
150                 155                 160                 165 aag tct aga atc cct tgg tat tcc cag tac ctc aat aat cca cta ggc     582
Lys Ser Arg Ile Pro Trp Tyr Ser Gln Tyr Leu Asn Asn Pro Leu Gly
                170                 175                 180 cga gct tta gcc ctc gca gcc aca ctc acg gtc ggc tgg ccg ttg tac     630
Arg Ala Leu Ala Leu Ala Ala Thr Leu Thr Val Gly Trp Pro Leu Tyr
            185                 190                 195 tta gcc ttc aat gtc tct gga cga cct tat aat cgg ttt gct tgt cac     678
Leu Ala Phe Asn Val Ser Gly Arg Pro Tyr Asn Arg Phe Ala Cys His
        200                 205                 210 ttt gat cct tct gga cct ata tat tct gat aga gaa agg ctt cag att     726
Phe Asp Pro Ser Gly Pro Ile Tyr Ser Asp Arg Glu Arg Leu Gln Ile
    215                 220                 225 tac att tct gac att ggg att ttc gct gca act tat gtg ctc tat cag     774
Tyr Ile Ser Asp Ile Gly Ile Phe Ala Ala Thr Tyr Val Leu Tyr Gln
```

```
                230                 235                 240                 245
att gcc atg gca aaa ggg tta gct tgg ctg ata tct att tat ggg ata          822
Ile Ala Met Ala Lys Gly Leu Ala Trp Leu Ile Ser Ile Tyr Gly Ile
                    250                 255                 260 cca ttg ctt att gtt aat gct ttt ctt gtg aca atc aca tat ttg cag          870
Pro Leu Leu Ile Val Asn Ala Phe Leu Val Thr Ile Thr Tyr Leu Gln
                265                 270                 275 cac act cac cct gca ttg cca cac tat gac tcg tcc gaa tgg gat tgg          918
His Thr His Pro Ala Leu Pro His Tyr Asp Ser Ser Glu Trp Asp Trp
                    280                 285                 290 ctc cgg gga gct ttg tcg aca gtg gat aga gat tat ggg gtg ttg aat          966
Leu Arg Gly Ala Leu Ser Thr Val Asp Arg Asp Tyr Gly Val Leu Asn
                295                 300                 305 aag gtt ttc cat aat att aca gac act cat gta acc cac cat ctc ttc         1014
Lys Val Phe His Asn Ile Thr Asp Thr His Val Thr His His Leu Phe
310                 315                 320                 325 tct aca atg cct cat tat cat gca atg gag gcc act aaa gca atc aag         1062
Ser Thr Met Pro His Tyr His Ala Met Glu Ala Thr Lys Ala Ile Lys
                    330                 335                 340 cct ata ttg ggc gag tat tat cag ttt gat ggc act ccg att ctt atg         1110
Pro Ile Leu Gly Glu Tyr Tyr Gln Phe Asp Gly Thr Pro Ile Leu Met
                345                 350                 355 gcg ctc tgg agg gag gcc aag gag tgc ctg ttt gtc gag cca gaa gag         1158
Ala Leu Trp Arg Glu Ala Lys Glu Cys Leu Phe Val Glu Pro Glu Glu
                    360                 365                 370 gga ggt ccc aac cga gga gtt ctc tgg tat gga aat aag tat taa             1203
Gly Gly Pro Asn Arg Gly Val Leu Trp Tyr Gly Asn Lys Tyr
375                 380                 385

<210> SEQ ID NO 5
<211> LENGTH: 387
<212> TYPE: PRT
<213> ORGANISM: Jatropha curcas

<400> SEQUENCE: 5

Met Gly Ala Gly Gly Gln Lys Thr Ala Val Leu Val Ser Ser Lys Phe
1               5                   10                  15

Lys Glu Met Glu Thr Asn Arg Arg Leu Lys Arg Val Pro His Thr Lys
            20                  25                  30

Pro Pro Phe Thr Leu Gly Gln Ile Lys Gln Ala Ile Pro Ser His Cys
        35                  40                  45

Phe Lys Arg Ser Leu Leu Arg Ser Phe Ser Tyr Leu Val Tyr Asp Leu
    50                  55                  60

Ser Leu Ser Ser Leu Phe Tyr Tyr Ile Ala Ala Ser Tyr Phe His Leu
65                  70                  75                  80

Leu Pro Ser Pro Ile Ser Tyr Ile Ala Trp Pro Ile Tyr Trp Thr Leu
                85                  90                  95

Gln Gly Cys Thr Leu Thr Gly Val Trp Val Ile Ala His Glu Cys Gly
            100                 105                 110

His His Ala Phe Ser Asp Tyr Gln Trp Val Asp Asp Thr Val Gly Leu
        115                 120                 125

Ile Leu His Ser Ser Leu Leu Val Pro Tyr Phe Ser Trp Lys Ile Ser
    130                 135                 140

His Arg Arg His His Ser Asn Thr Gly Ser Ile Glu Arg Asp Glu Val
145                 150                 155                 160

Phe Val Pro Lys Phe Lys Ser Arg Ile Pro Trp Tyr Ser Gln Tyr Leu
                165                 170                 175
```

```
Asn Asn Pro Leu Gly Arg Ala Leu Ala Leu Ala Ala Thr Leu Thr Val
            180                 185                 190
Gly Trp Pro Leu Tyr Leu Ala Phe Asn Val Ser Gly Arg Pro Tyr Asn
            195                 200                 205
Arg Phe Ala Cys His Phe Asp Pro Ser Gly Pro Ile Tyr Ser Asp Arg
    210                 215                 220
Glu Arg Leu Gln Ile Tyr Ile Ser Asp Ile Gly Ile Phe Ala Ala Thr
225                 230                 235                 240
Tyr Val Leu Tyr Gln Ile Ala Met Ala Lys Gly Leu Ala Trp Leu Ile
                245                 250                 255
Ser Ile Tyr Gly Ile Pro Leu Leu Ile Val Asn Ala Phe Leu Val Thr
            260                 265                 270
Ile Thr Tyr Leu Gln His Thr His Pro Ala Leu Pro His Tyr Asp Ser
        275                 280                 285
Ser Glu Trp Asp Trp Leu Arg Gly Ala Leu Ser Thr Val Asp Arg Asp
    290                 295                 300
Tyr Gly Val Leu Asn Lys Val Phe His Asn Ile Thr Asp Thr His Val
305                 310                 315                 320
Thr His His Leu Phe Ser Thr Met Pro His Tyr His Ala Met Glu Ala
                325                 330                 335
Thr Lys Ala Ile Lys Pro Ile Leu Gly Glu Tyr Tyr Gln Phe Asp Gly
            340                 345                 350
Thr Pro Ile Leu Met Ala Leu Trp Arg Glu Ala Lys Glu Cys Leu Phe
        355                 360                 365
Val Glu Pro Glu Glu Gly Gly Pro Asn Arg Gly Val Leu Trp Tyr Gly
    370                 375                 380
Asn Lys Tyr
385

<210> SEQ ID NO 6
<211> LENGTH: 8579
<212> TYPE: DNA
<213> ORGANISM: Jatropha curcas

<400> SEQUENCE: 6
caacaatcca caaaagtgca tccaatggtg acatggtagc aaactggaac actaaacccc      60
aaaatttcgt ggtcttcgca gtctcataat gctacaattt caactttggt tcctacttgt     120
tatacacagg ctattacatg ctcccattgg tgagatgcta tgattcagga attaaaatgc     180
attattacaa actggtacat gggaattggt tcctcgtagt attgcacata atgttgtggg     240
ttgcaagtgg gtctttcgaa tcaaacaaaa agttgatggt agtattaaac attacaaagc     300
ttgactagta gcaaagggt tcatcaacg ccctggtgtt gattattttg agactttttc      360
accagttgtt aaaccaacta ccatccgagt aatcttgtct ctagctgtct ccaaaaattg     420
ggtggtcaaa caattagata tttccaatgc atttttgcat ggtgacttgg aggacgaagt     480
atttatgaaa caaccaccag ggttccaaga caaaatgaag ccagaccatg tatgtcgcct     540
tcgccattct ctttatggtt tgcaccaagc accacgacaa tggtacaaga aactacattc     600
tgcattgatt cttcatggct ttcgtgtttc acctgcagac tcatcattac ttcactatgc     660
taaaaccaat gtcattcttt tagcattagt gtacgttgat gatacaatat taacaggcac     720
tagtcttagc gagatatagc gaataatggg ctctttacag tcgaaattta tgcttaaaga     780
tcttgggcga ttatattatt ttctaggtat ggaagcacac tggttgcctg aagggctact     840
tctcacacaa caaaaatata tactggattt gttgaaaaag gctagaatgg aagcttgcaa     900
```

```
aggtattgct acaccagctg tctcgaaaga taaaatgtca tcgactggaa gttccttgtt      960
ctcagatcct acgttctatc atcgtattgt gggtggtctg cagtatctca gtttaactag     1020
accagaagtc tgttttttctg ctcataaaaa ttctcagttt cttcaggctc ctaccaatga     1080
taattgaagt tcagtcaagc gcatcttacg atacttgaaa gagacagtac attacggacc     1140
tctcattcga aaatccactc atactgattt gaatatgtat actgatgctg attgggcaag     1200
cagtcttgat gatcgaaaat ccaccacagg ttatgcaatt tttgtgggtc aaaatcttat     1260
atcttggaat tccaaaaagc aacagactgt tgctcgctct tccactgaag tggagtatag     1320
agccattgga ttagctgcca ctgaattaac atggatccaa gcacttttac gtgatattgg     1380
ctttcattct gttaatatac ctaatctatg gtgtgacaat attggtgtta cgtatttgtc     1440
agtaaatcaa gttttttcatg cgcgcacaaa gcatttcgag gttgattttc attttgtccg     1500
tgacaaagta caaagaagg agcttcaggt caagttcatt tgttccaatg atcaactcac       1560
tgatatctta acaaaaccgc tttccaaagc acgacatcga gctctaatgt ttcatttgac     1620
aatttgatca ttcttcaaga atgctcgaat tgaggagacg tgataaggat accagctgta     1680
tattttatat tgttgtaatt aaccgtatcc taagataagt ttgtataact acaaactctt     1740
gtaaataaat atagcaccga aacacagaaa taatacaagt tgaattccaa aagttttaaa     1800
cagctttaga aacacttgtg aggagtacgt gacatcttag accaatttca cattggttaa     1860
gcacaaggta aaagcatgag aaaaagcaag ccttacattg gcaagtcata ttttgggcta     1920
cgagatgatt ctagttcggg aataaatctg tgtaggctga gctcaaagta gacaatatat     1980
cttgccaaag caaatatatt taatttaata tagtggtgga tctattaatg aagaaaaaaa     2040
agtaaaaaag aaagaaagaa aaggaagcat aaacaaaaca tgcttacaat ttttttttaat    2100 tagttagaaa agggttaata atttgtttct tagttattat cattagggat aaggtgaaag     2160
taattatgta aatgcaattt attttttaaat tttttttagaa gaaggtttaa caattattaa    2220
aatgaccttg ttaagcacaa cttgttttgg atcaaacgag tttttttttt tttttttttg    2280
aggtttaatt taacttttt tcctacttta tgtacataaa taaaaataag acaacagagg      2340
tgcctccagg gctgagtgaa gaaggcataa aacaaattat ctaaggaaca caaaccgcct     2400
ctttataacc aagtcatata cttaccttca gaagactgaa aagattataa ttttccaaca     2460
cttaaatcaa tttgaactaa tttttattat ataaccaaaa caaattgaat ctaattgaat     2520
taattttcag tttgatttaa ttcagttcgg tattatatat tgacttattt ttaagcttaa     2580
tttagctgga ttttttagttt tatgaaaatt gaattgaact aaaaaaattg atctttttt     2640 ttttttttt ttttttttgt taaatggaat gcaaactata gtattacttg ttagcttaac      2700
tattcaccat actgaagaaa aattccaatt gcaaatcata gcgatggaac tgagcttcta     2760
atattcaagg gtgaaaataa attgaagagt caaaggtttt acaaaattac tatttcatct    2820
ctgttgtttg gagaaactat tgcgaggtcc ctaagttttg gttttgttaa actattcacc     2880
ccttccatca gtgctatttt tgttgttaaa tatcctattt tggtcatacc acagtaatat     2940
ttaacatacc aatcatcagg aacttcacag taatttttca aacacaaaat ttcagttaaa     3000
tctttatgga ctttatagta atttatgcta attttaaaaa ttcttgggga ggaggggtaa     3060
aagtaaataa ttgatttaat ttaaatataa aataagagaa tttcaaaaat attattggag     3120
ggagattacc acctactcta ggcatctccc attgctcatc aggatctcat ctagtcttac     3180
tttcatcaat gcaaatttct tgcccccata ttttttgttat ggaaattttg gtcccattac    3240
```

```
aattattaga taaatttgtt gtatgattgt gaaacttata tgttggagat atcaaataca    3300
aaatagattt ttttttttta attattctct tttggaggtt taattagtgt gggctacaaa    3360
ataagaggca gttcatttt aattcataat gatttctaat ccattaattt atagtccatt     3420
tgagattgat tttgaagtta aaattttaaa atatctggct tttcctaact gacacttagt    3480
tttatgttgg atttctttt aaaggaaaag aaaaggtaaa tagaacaatt ttcatcattt     3540
tcaatgatca ttaggtaaac ggaaaattct tgtctagact agctctatga tctcacctat    3600
aaaccaaact gatcaaagta agaatttta aaaattgttc cttccttttc taaaaaaaaa     3660
aaaaaaaaaa aaaaattggt ccttccatga tcattaggta aagggaaaat acttgttagt    3720
ctagcttctt tttttttttt tttttttttt tttttttttt ttttaataac agcatttcag    3780
ttataactag aaaagctaac ttcaatccaa ttaatgttta ataatgaatc tgcagagaag    3840
cttaacagaa caatgggagc cggtggccaa aaaactgctg tcctcgtcag cagtaagttc    3900
aaggaaatgg aaaccaacag acgcctgaag cgagttccac acacaaaacc tccattcact    3960
cttggccaaa tcaaacaagc catcccatcc cattgcttta aacgctccct tctccgctct    4020
ttctcctacc ttgtttatga cctctcttta agctctctct tctactacat tgccgctagc    4080
tacttccatc ttctcccttc tccgatctcc tacattgctt ggcccatcta ctggactctc    4140
cagggctgca ctctcactgg tgtttgggtc attgctcatg aatgcggcca ccatgctttt    4200
agtgactatc aatgggttga tgacactgtt ggcctaattc tccactcttc acttcttgtt    4260
ccttattttt catggaaaat tagccatcgt cgccatcact ccaacaccgg ttccattgaa    4320
cgtgatgagg tctttgtccc caaattcaag tctagaatcc cttggtattc ccagtacctc    4380
aataatccac taggccgagc tttagccctc gcagccacac tcacggtcgg ctggccgttg    4440
tacttagcct tcaatgtctc tggacgacct tataatcggt ttgcttgtca ctttgatcct    4500
tctggaccta tatattctga tagagaaagg cttcagattt acatttctga cattgggatt    4560
ttcgctgcaa cttatgtgct ctatcagatt gccatggcaa aagggttagc ttggctgata    4620
tctatttatg ggataccatt gcttattgtt aatgcttttc ttgtgacaat cacatatttg    4680
cagcacactc acctgcatt gccacactat gactcgtccg aatgggattg gctccgggga    4740
gctttgtcga cagtggatag agattatggg gtgttgaata aggttttcca taatattaca    4800
gacactcatg taacccacca tctcttctct acaatgcctc attatcatgc aatggaggcc    4860
actaaagcaa tcaagcctat attgggcgag tattatcagt ttgatggcac tccgattctt    4920
atggcgctct ggagggaggc caaggagtgc ctgtttgtcg agccagaaga gggaggtccc    4980
aaccgaggag ttctctggta tggaaataag tattaagagc tataatatgt ggtttggcct    5040
tcagagaagt taattagaat aactatgcag agagtgtgaa tgtagtatag atgttagtaa    5100
tggagaagaa aaactatatg cgtagtagct ttctttacgg gaaagtggtg tttgagttat    5160
gtctgtttat ggaactctac aacttgaatt aagtcgttta gttttaaat catcgtttgc     5220 tctttgtttt ttaatttctt atatatattg aattaagtcg atgttattgg tacaatgaaa    5280
tatataaaaa gttattaata aagcgttaac ctcaattctc gtaagagtaa gaacatgaaa    5340 aactttata cttatggtc cgagagaatt atatatatac acacactata attaattaat      5400
tatataatgt tatatgcaag gaaaatgttt cgatctatat ctctctccat tcgatattat    5460
ttctctcctt tttgttgttt ttctaaaaat tttaatatat ttaaatatct atatatttat    5520
ataatatata aaagcatgat agtttgcttt atatggaaac taaatataaa gagcacaatt    5580
tgtcactagg atggctgtta gaattctaac acaatttgtc acttgatagt attttgaatt    5640
```

```
atagaatgac aaatgttaga attctaacac aatttaacat aattgtaaga attgtaagaa    5700
catcagttgt tttatatttt cagataattc ttatcaagat aataactata aaaaaaagat    5760
tatctctagc atttaatata ttaatctaaa tttattcctt cttacaaaac aattaataag    5820
taatccacac acttaaaaaa gtgtgtataa acaatatata aacaatttaa aaaatataaa    5880
ttgaaacgta caggatacga tactttttaa aaaagtaaga catcctgacg cttaggacac    5940
actaaataag taatacatta atattttcaa taaataaata attatttata ataaatcata    6000
aatataaaca aaaacaatga atttctcatt tcaacaacac aaaaacaaaa ttttaaaaaa    6060
aaaacttcat ttttttgata ataaaaaaag tcttgattga ttaacttggt gtataaaata    6120
gtcttatata ccaggagtta agttgcacga acacaggaca cgagatacag gaacatatgg    6180
atacaataat ttttaaaagt aaaacatcca cacgcttaga atatactaca ctaaataagt    6240
aatatactaa tatttcaaat aaataaataa tcatttataa taattataaa cataaaataa    6300
aaaaaactta atttcttatt tcaatgacac aaaaacaaat taaaaaaaaa acacttcatt    6360
ttttactggt aataaaaaaa aacatggttg attagtttgg tgtattgagt agttccatac    6420
accaggagct aggttgcaca tacacgagac acaaaataca ggaacgtata gatacgataa    6480
tgtttaaaaa cgtaggcatt catatgctta gaacacatta cactaaataa gtaacacatt    6540 aatatttaa ataaataaat aatcatttat actaaatcat aaacataaaa caaaaaaat    6600 acttaatttc ttatttcaac gacacaaaaa taatttaaaa aaaacacttc atgttttatt    6660
ggtaataaaa aaaaattctt ggttagcttg gtatatggag tagtatcata tgtcaggagc    6720
taggttgcat ggacacgtga cacgagatac gaaaaattat gagatacgat aatttttaaa    6780
attgtaagac atcctcacgc atagaacaca ctatattaaa tacataatac attaacattt    6840
caaataaata aacaatcttt ataataaatc atgacaaaaa atacttaatt tcttatttca    6900 atgcacacaaa aataaattaa aaaaacttca tctttattgg taataagaaa aaatctttgt    6960
tgattagttt ggtgtatgga gtagtctcat atactaggag ctgagttaca cggacacggg    7020
aatatacagg atacattaat ttttaaaaaa tataaaacat ccacacgctt aggagacatc    7080
atactaaata agtaatacat taatatttca aataaataaa caatcattta taataaatta    7140
caaatataaa ataaaatgaa aacttaattt cttatttcaa tgacaaaaaa aatttaaaaa    7200
aaacttacat ttttatttat aataaaaaaa taccttgatt gattagcttg gtgtatggag    7260
tagtatcata taccaggagc taagttgtac ggacacaaga tatgagatac aggaatatac    7320
aggatataat aattttttaaa aaaagtagaa acatccacac acttaggaca caccacacta    7380
agtaagtaat atattaatat tttaaataaa taaataatca tttataataa attataaata    7440
taaaataaaa aaattaattt cttatttcaa taacacaaac aaattaaaaa aatacttcat    7500
ttttattagt aataaataaa atcttgtttg attagtttag tatatggagt agtctcatat    7560
accaagagtt aggttgcacg gacacagtac acaataaatg aaaatgtata agatacgata    7620 attttttaaaa aagcaagaca tccacacgct taggacacgt tacactaaat cagtaataca    7680
ttaatatttc aaataaataa acaattattt ataataaatc ataaatataa aataaaaaaa    7740
tacttaattt cttttttcaa tataattaat taaattctta aaattattat cactattgca    7800
aaatacatta atagtgtgta tgcattttttt ttaatgtagg tcataccatg tatgactttt    7860
gctgttgcat accttatgaa acgcttcgca ggataattaa gacataccat gtatgacttt    7920
tgctgttgca taccttatga aacgcttcgc aggataatta agaagacata tcttagcatt    7980
```

-continued

```
gaaactttc   agtatatttc   aatgagagat   aatttattat   tttatttat   agttttacta    8040 tttttgaatg   atgttataaa   agattatttc   atcctttaat   actgtttcgc   gcattgtcgg    8100
ggttctacca   ctagtaatat   ataaaagcag   agaaatctat   cttaaatgta   aatctctcaa    8160
attgcccagt   gtaaggagag   tagttattta   gtataattgt   atgaaaatca   attgtagtga    8220
tagtaattgt   aaaagataa    atagtttat    attttcagat   aatgctatat   gggaagaaaa    8280
aagaaaaaaa   aataaactga   tattaaaaag   caaaaactat   tttatttgga   aataaggaag    8340
caatataagg   gaaatgaatt   tcaataattg   tcttttcaaa   tgagaaggaa   aaaaattata    8400
aaaataaatt   tgtaaaagaa   actcagtctt   tttaatgatt   gatttcattg   cctcggccct    8460
ctttaccttc   tcattgtaat   taattttatt   tttctttgt   atccaaaaaa   taagtaacat    8520 aagtttttc   tgaaaaataa   tttagttcct   tctttttttt   ttttaaaaat   ttagcttcg     8579
```

<210> SEQ ID NO 7
<211> LENGTH: 383
<212> TYPE: PRT
<213> ORGANISM: Arabidopsis thaliana

<400> SEQUENCE: 7

```
Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
                20                  25                  30

Val Gly Asp Leu Lys Lys Ala Ile Pro Pro His Cys Phe Lys Arg Ser
            35                  40                  45

Ile Pro Arg Ser Phe Ser Tyr Leu Ile Ser Asp Ile Ile Ala Ser
    50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270
```

```
Gln His Thr His Pro Ser Leu Pro His Tyr Asp Ser Glu Trp Asp
            275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
            355                 360                 365

Arg Glu Gly Asp Lys Lys Gly Val Tyr Trp Tyr Asn Asn Lys Leu
            370                 375                 380

<210> SEQ ID NO 8
<211> LENGTH: 383
<212> TYPE: PRT
<213> ORGANISM: Ricinus communis

<400> SEQUENCE: 8

Met Gly Ala Gly Gly Arg Met Ser Val Pro Pro Ser Lys Lys Val
1               5                   10                  15

Glu Ser Asp Asp Leu Lys Arg Ala Pro Ser Ser Lys Pro Pro Phe Thr
                20                  25                  30

Leu Gly Gln Ile Lys Lys Ala Ile Pro Pro His Cys Phe Lys Arg Ser
            35                  40                  45

Ile Pro Arg Ser Phe Ser Tyr Val Val Tyr Asp Leu Thr Ile Ala Phe
50                  55                  60

Leu Phe Tyr Tyr Val Ala Thr Asn Tyr Phe His Leu Leu Pro Glu Pro
65                  70                  75                  80

Leu Ser Tyr Val Ala Trp Pro Ile Tyr Trp Ala Leu Gln Gly Cys Val
                85                  90                  95

Leu Thr Gly Val Trp Val Ile Ala His Glu Cys Gly His His Ala Phe
            100                 105                 110

Ser Asp Tyr Gln Leu Leu Asp Asp Val Val Gly Leu Ile Leu His Ser
            115                 120                 125

Cys Leu Leu Val Pro Tyr Phe Ser Trp Lys His Ser His Arg Arg His
        130                 135                 140

His Ser Asn Thr Gly Ser Leu Glu Arg Asp Glu Val Phe Val Pro Lys
145                 150                 155                 160

Lys Lys Ser Ser Ile Arg Trp Tyr Ser Lys Tyr Leu Asn Asn Pro Pro
                165                 170                 175

Gly Arg Ile Met Thr Ile Ala Val Thr Leu Thr Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Tyr Asn Asp Arg Glu Arg Ile Glu
    210                 215                 220

Ile Phe Ile Ser Asp Ala Gly Val Leu Ala Val Thr Phe Gly Leu Tyr
225                 230                 235                 240

Gln Leu Ala Ile Ala Lys Gly Leu Ala Trp Val Val Cys Val Tyr Gly
                245                 250                 255

Val Pro Leu Leu Val Val Asn Ser Phe Leu Val Leu Ile Thr Phe Leu
            260                 265                 270
```

```
Gln His Thr His Pro Ala Leu Pro His Tyr Asp Ser Ser Glu Trp Asp
            275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Gln Phe Asp Gly Thr Ser Phe Tyr
                340                 345                 350

Lys Ala Met Trp Arg Glu Ala Lys Glu Cys Ile Tyr Val Glu Lys Asp
            355                 360                 365

Asp Ala Glu Gln Asn Gly Gly Val Phe Trp Tyr Asn Asn Lys Phe
            370                 375                 380

<210> SEQ ID NO 9
<211> LENGTH: 387
<212> TYPE: PRT
<213> ORGANISM: Ricinus communis

<400> SEQUENCE: 9

Met Gly Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
                20                  25                  30

Pro Pro Phe Thr Leu Gly Asp Leu Lys Arg Ala Ile Pro Pro His Cys
            35                  40                  45

Ser Glu Arg Ser Phe Val Arg Ser Phe Ser Tyr Val Ala Tyr Asp Val
        50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
                100                 105                 110

His His Ala Phe Ser Glu Tyr Gln Leu Ala Asp Asp Ile Val Gly Leu
            115                 120                 125

Ile Val His Ser Ala Leu Leu Val Pro Tyr Phe Ser Trp Lys Tyr Ser
            130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Leu
                165                 170                 175

Asn Asn Pro Pro Gly Arg Val Leu Thr Leu Ala Ala Thr Leu Leu Leu
                180                 185                 190

Gly Trp Pro Leu Tyr Leu Ala Phe Asn Val Ser Gly Arg Pro Tyr Asp
            195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Ala Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
```

```
                    260                 265                 270
Ile Thr Tyr Leu Gln His Thr His Pro Ala Ile Pro Arg Tyr Gly Ser
                275                 280                 285

Ser Glu Trp Asp Trp Leu Arg Gly Ala Met Val Thr Val Asp Arg Asp
            290                 295                 300

Tyr Gly Val Leu Asn Lys Val Phe His Asn Ile Ala Asp Thr Gln Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 10
<211> LENGTH: 383
<212> TYPE: PRT
<213> ORGANISM: Vernicia fordii

<400> SEQUENCE: 10

Met Gly Ala Gly Gly Arg Met Ser Val Pro Pro Pro Lys Lys Leu
1               5                   10                  15

Glu Ser Glu Val Leu Lys Arg Val Pro His Ser Lys Pro Pro Phe Thr
            20                  25                  30

Leu Gly Gln Leu Lys Lys Ala Ile Pro Pro His Cys Phe Gln Arg Ser
        35                  40                  45

Val Leu Arg Ser Phe Ser Tyr Val Val Tyr Asp Leu Thr Val Ala Phe
    50                  55                  60

Ile Phe Tyr Tyr Ile Ala Thr Asn Tyr Phe His Leu Leu Pro Gln Pro
65                  70                  75                  80

Leu Ser Tyr Val Ala Trp Pro Ile Tyr Trp Ala Leu Gln Gly Cys Val
                85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Val Leu His Ser
        115                 120                 125

Cys Leu Leu Val Pro Tyr Phe Ser Trp Lys His Ser His Arg Arg His
    130                 135                 140

His Ser Asn Thr Ala Ser Leu Glu Arg Asp Glu Val Phe Val Pro Lys
145                 150                 155                 160

Lys Lys Ser Ser Ile Arg Trp Phe Ser Lys Tyr Leu Asn Asn Pro Pro
                165                 170                 175

Gly Arg Leu Phe Thr Leu Thr Ile Thr Leu Thr Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Tyr Thr Asp Arg Glu Arg Thr Glu
    210                 215                 220

Ile Tyr Ile Ser Asp Ala Gly Val Leu Ala Val Thr Phe Gly Leu Tyr
225                 230                 235                 240
```

```
Arg Leu Ala Ala Ala Lys Gly Leu Ala Trp Val Ile Cys Val Tyr Gly
                245                 250                 255

Val Pro Leu Leu Ile Val Asn Ala Phe Leu Val Met Ile Thr Tyr Leu
            260                 265                 270

Gln His Thr His Pro Ser Ile Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Gln Phe Asp Gly Thr Pro Phe Tyr
            340                 345                 350

Lys Ala Met Trp Arg Glu Ala Lys Glu Cys Ile Tyr Val Glu Ala Asp
        355                 360                 365

Asp Gly Asp Glu Ser Lys Gly Val Tyr Trp Tyr Asn Lys Lys Phe
    370                 375                 380

<210> SEQ ID NO 11
<211> LENGTH: 386
<212> TYPE: PRT
<213> ORGANISM: Venicia fordii

<400> SEQUENCE: 11

Met Gly Ala Gly Gly Arg Met Ser Val Ala Pro Asn Asn Ser Lys Cys
1               5                   10                  15

Glu Lys Lys Glu Ser Arg Ser Val Lys Arg Val Pro His Thr Lys Pro
            20                  25                  30

Pro Phe Thr Leu Gly Gln Leu Lys Gln Ala Ile Pro Ser His Cys Phe
        35                  40                  45

Lys Arg Ser Leu Leu Arg Ser Phe Ser Tyr Val Val Tyr Asp Leu Ser
    50                  55                  60

Leu Ser Phe Ile Phe Tyr Ser Ile Ala Thr Thr Tyr Phe His Leu Leu
65                  70                  75                  80

Pro Ser Pro Ile Thr Tyr Ile Ala Trp Pro Val Tyr Trp Ala Phe Gln
                85                  90                  95

Gly Cys Ile Leu Thr Ser Val Trp Val Leu Gly His Glu Cys Gly His
            100                 105                 110

His Ala Phe Ser Glu Tyr Asn Trp Leu Asp Asp Thr Ile Gly Leu Ile
        115                 120                 125

Leu His Ser Ser Leu Leu Val Pro Tyr Phe Ser Phe Lys Ile Ser His
    130                 135                 140

Arg Arg His His Ser Asn Ile Ala Ser Leu Glu Arg Asp Glu Val Phe
145                 150                 155                 160

Val Pro Arg Leu Lys Ser Ala Ile Pro Trp Tyr Ser Lys Tyr Leu Asn
                165                 170                 175

Asn Pro Pro Gly Arg Ala Leu Thr Leu Val Ala Thr Leu Phe Ile Gly
            180                 185                 190

Trp Pro Leu Tyr Leu Ala Phe Asn Val Ser Gly Arg Tyr Tyr Asp Arg
        195                 200                 205

Phe Ala Cys His Tyr Asp Pro Tyr Ser Pro Ile Tyr Ser Asp Arg Glu
    210                 215                 220

Arg Leu Gln Ile Tyr Ile Ser Asp Ala Met Ile Phe Val Ala Ala Tyr
225                 230                 235                 240
```

```
Val Leu Tyr Lys Ile Ala Met Ala Lys Gly Leu Ala Trp Leu Val Cys
                245                 250                 255

Ile Tyr Gly Val Pro Leu Leu Ile Val Asn Ala Leu Val Val Thr Ile
            260                 265                 270

Thr Ser Leu Gln His Thr His Val Ala Leu Pro His Tyr Asp Ser Ser
        275                 280                 285

Glu Trp Asp Trp Leu Arg Gly Leu Ala Thr Val Asp Arg Asp Tyr
    290                 295                 300

Gly Val Phe Asn Lys Ile Phe His Asn Ala Thr Asp Thr His Val Ile
305                 310                 315                 320

His His Leu Phe Ser Ser Met Pro His Tyr His Gly Val Glu Ala Thr
                325                 330                 335

Arg Ala Ile Lys Pro Ile Leu Gly Asp Tyr Tyr Leu Phe Asp Asp Thr
            340                 345                 350

Pro Ile His Val Ala Leu Trp Arg Glu Ala Lys Glu Cys Leu Phe Val
        355                 360                 365

Glu Pro Asp Glu Gly Asp Asn Asn Asn Gly Val Phe Trp Tyr Ser Asn
    370                 375                 380

Lys Phe
385

<210> SEQ ID NO 12
<211> LENGTH: 31
<212> TYPE: DNA
<213> ORGANISM: Jatropha curcas

<400> SEQUENCE: 12
atcactcgag ccaccattca cacttggtca g                                  31

<210> SEQ ID NO 13
<211> LENGTH: 32
<212> TYPE: DNA
<213> ORGANISM: Jatropha curcas

<400> SEQUENCE: 13
gtataagctt catgagtgtc tgtaatgtta tg                                 32

<210> SEQ ID NO 14
<211> LENGTH: 34
<212> TYPE: DNA
<213> ORGANISM: Jatropha curcas

<400> SEQUENCE: 14
caatatctag accatgggtg ccggtggcag aatg                               34

<210> SEQ ID NO 15
<211> LENGTH: 36
<212> TYPE: DNA
<213> ORGANISM: Jatropha curcas

<400> SEQUENCE: 15
tattggatcc ggaaacttgt ttttgtacca gaacac                             36

<210> SEQ ID NO 16
<211> LENGTH: 15063
<212> TYPE: DNA
<213> ORGANISM: Artificial Sequence
<220> FEATURE:
<223> OTHER INFORMATION: vector
```

```
<400> SEQUENCE: 16
tcgagcgggg taccatgggt aagggagaag aacttttcac tggagttgtc ccaattcttg     60
ttgaattaga tggtgatgtt aatgggcaca aattttctgt cagtggagag ggtgaaggtg    120
atgcaacata cggaaaactt acccttaaat ttatttgcac tactgaaaag cttcctgttc    180
cttggccaac acttgtcact actcttactt atggtgttca atgcttttca agatacccag    240
atcatatgaa gcggcacgac ttcttcaaga gcgccatgcc tgagggatac gtgcaggaaa    300
ggaccatctt cttcaaggac gacgggaact acaagacacg tgctgaagtc aagtttgagg    360
gagacaccct tgtcaacagg atcgagctta agggaatcga tttcaaggag gacggaaaca    420
tcctcggcca caagttggaa tacaactaca actcccacaa cgtatacatc atggcagaca    480
aacaaaagaa tggaatcaaa gttaacttca aaattagaca caacattgaa gatggaagcg    540
ttcaactagc agaccattat caacaaaata ctccaattgg cgatggccct gtccttttac    600
cagacaacca ttacctgtcc acacaatctg ccctttcgaa agatcccaac gaaaagagag    660
accacatggt ccttcttgag tttgtaacag ctgctgggat tacacatggc atggatgaac    720
tatacaaata aatgggtaag ggagaagaac ttttcactgg agttgtccca attcttgttg    780
aattagatgg tgatgttaat gggcacaaat tttctgtcag tggagagggt gaaggtgatg    840
caacatacgg aaaacttacc cttaaatttt tttgcactac tggaaagctt cctgttcctt    900
ggccaacact tgtcactact cttacttatg gtgttcaatg cttttcaaga tacccagatc    960
atatgaagcg gcacgacttc ttcaagagcg ccatgcctga gggatacgtg caggaaagga   1020
ccatcttctt caaggacgac gggaactaca agacacgtgc tgaagtcaag tttgagggag   1080
acacccttgt caacaggatc gagcttaagg gaatcgattt caaggaggac ggaaacatcc   1140
tcggccacaa gttggaatac aactacaact cccacaacgt atacatcatg gcagacaaac   1200
aaaagaatgg aatcaaagtt aacttcaaaa ttagacacaa cattgaagat ggaagcgttc   1260
aactagcaga ccattatcaa caaaatactc caattggcga tggccctgtc cttttaccag   1320
acaaccatta cctgtccaca atctgccctt tcgaaagat cccaacgaa aagagagacc   1380
acatggtcct tcttgagttt gtaacagctg ctgggattac acatggcatg gatgaactat   1440
acaaataaac tagtcgatcc aggcctccca gctttcgtcc gtatcatcgg tttcgacaac   1500
gttcgtcaag ttcaatgcat cagtttcatt gcccacacac cagaatccta ctaagtttga   1560
gtattatggc attggaaaag ctgttttctt ctatcatttg ttctgcttgt aatttactgt   1620
gttctttcag ttttttgttt tcggacatca aaatgcaaatg gatggataag agttaataaa   1680
tgatatggtc cttttgttca ttctcaaatt attattatct gttgttttta ctttaatggg   1740
ttgaatttaa gtaagaaagg aactaacagt gtgatattaa ggtgcaatgt tagacatata   1800
aaacagtctt tcacctctct ttggttatgt cttgaattgg tttgtttctt cacttatctg   1860
tgtaatcaag tttactatga gtctatgatc aagtaattat gcaatcaagt taagtacagt   1920
ataggctttt tgtgtcgagg gggtaccgag tcgaggaatt cactggccgt cgttttacaa   1980
cgtcgtgact gggaaaaccc tggcgttacc caacttaatc gccttgcagc acatccccct   2040
ttcgccagct ggcgtaatag cgaagaggcc cgcaccgatc gcccttccca acagttgcgc   2100
agcctgaatg gcgggtaccg agctcgaatt caattcggcg ttaattcagt acattaaaaa   2160
cgtccgcaat gtgttattaa gttgtctaag cgtcaatttg tttacaccac aatatatcct   2220
gccaccagcc agccaacagc tccccgaccg gcagctcggc acaaaatcac cactcgatac   2280
aggcagccca tcagtccggg acggcgtcag cgggagagcc gttgtaaggc ggcagacttt   2340
```

```
gctcatgtta ccgatgctat tcggaagaac ggcaactaag ctgccgggtt tgaaacacgg      2400
atgatctcgc ggagggtagc atgttgattg taacgatgac agagcgttgc tgcctgtgat      2460
caattcgggc acgaacccag tggacataag cctcgttcgg ttcgtaagct gtaatgcaag      2520
tagcgtaact gccgtcacgc aactggtcca gaaccttgac cgaacgcagc ggtggtaacg      2580
gcgcagtggc ggttttcatg gcttcttgtt atgacatgtt tttttggggt acagtctatg      2640
cctcgggcat ccaagcagca agcgcgttac gccgtgggtc gatgtttgat gttatggagc      2700
agcaacgatg ttacgcagca gggcagtcgc cctaaaacaa agttaaacat catggggaa       2760 gcggtgatcg ccgaagtatc gactcaacta tcagaggtag ttggcgtcat cgagcgccat      2820
ctcgaaccga cgttgctggc cgtacatttg tacggctccg cagtggatgg cggcctgaag      2880
ccacacagtg atattgattt gctggttacg gtgaccgtaa ggcttgatga acaacgcgg       2940 cgagctttga tcaacgacct tttggaaact tcggcttccc ctggagagag cgagattctc      3000
cgcgctgtag aagtcaccat tgttgtgcac gacgacatca ttccgtggcg ttatccagct      3060
aagcgcgaac tgcaatttgg agaatggcag cgcaatgaca ttcttgcagg tatcttcgag      3120
ccagccacga tcgacattga tctggctatc ttgctgacaa aagcaagaga acatagcgtt      3180
gccttggtag gtccagcggc ggaggaactc tttgatccgg ttcctgaaca ggatctattt      3240
gaggcgctaa atgaaacctt aacgctatgg aactcgccgc ccgactgggc tggcgatgag      3300
cgaaatgtag tgcttacgtt gtcccgcatt tggtacagcg cagtaaccgg caaaatcgcg      3360
ccgaaggatg tcgctgccga ctgggcaatg gagcgcctgc cggcccagta tcagcccgtc      3420
atacttgaag ctagacaggc ttatcttgga caagaagaag atcgcttggc ctcgcgcgca      3480
gatcagttgg aagaatttgt ccactacgtg aaaggcgaga tcaccaaggt agtcggcaaa      3540
taatgtctag ctagaaattc gttcaagccg acgccgcttc gccggcgtta actcaagcga      3600
ttagatgcac taagcacata attgctcaca gccaaactat caggtcaagt ctgcttttat      3660 tattttttaag cgtgcataat aagccctaca caaattggga gatatatcat gcatgaccaa      3720
aatcccttaa cgtgagtttt cgttccactg agcgtcagac cccgtagaaa agatcaaagg      3780
atcttcttga gatccttttt ttctgcgcgt aatctgctgc ttgcaaacaa aaaaaccacc      3840
gctaccagcg gtggtttgtt tgccggatca agagctacca actcttttc cgaaggtaac       3900 tggcttcagc agagcgcaga taccaaatac tgtccttcta gtgtagccgt agttaggcca      3960
ccacttcaag aactctgtag caccgcctac atacctcgct ctgctaatcc tgttaccagt      4020
ggctgctgcc agtggcgata gtcgtgtct  taccgggttg gactcaagac gatagttacc      4080
ggataaggcg cagcggtcgg gctgaacggg gggttcgtgc acacagccca gcttggagcg      4140
aacgacctac accgaactga gatacctaca gcgtgagcta tgagaaagcg ccacgcttcc      4200
cgaagggaga aaggcggaca ggtatccggt aagcggcagg gtcggaacag gagagcgcac      4260
gagggagctt ccaggggaa acgcctggta tctttatagt cctgtcgggt ttcgccacct       4320
ctgacttgag cgtcgatttt tgtgatgctc gtcaggggg  cggagcctat ggaaaaacgc      4380
cagcaacgcg gcctttttac ggttcctggc cttttgctgg ccttttgctc acatgttctt      4440
tcctgcgtta tcccctgatt ctgtggataa ccgtattacc gcctttgagt gagctgatac      4500
cgctcgccgc agccgaacga ccgagcgcag cgagtcagtg agcgaggaag cggaagagcg      4560
cctgatgcgg tattttctcc ttacgcatct gtgcggtatt tcacaccgca tatggtgcac      4620
tctcagtaca atctgctctg atgccgcata gttaagccag tatacactcc gctatcgcta      4680
```

```
cgtgactggg tcatggctgc gccccgacac ccgccaacac ccgctgacgc gccctgacgg      4740
gcttgtctgc tcccggcatc cgcttacaga caagctgtga ccgtctccgg gagctgcatg      4800
tgtcagaggt tttcaccgtc atcaccgaaa cgcgcgaggc agggtgcctt gatgtgggcg      4860
ccggcggtcg agtggcgacg gcgcggcttg tccgcgccct ggtagattgc ctggccgtag      4920
gccagccatt tttgagcggc cagcggccgc gataggccga cgcgaagcgg cggggcgtag      4980
ggagcgcagc gaccgaaggg taggcgcttt ttgcagctct tcggctgtgc gctggccaga      5040
cagttatgca caggccaggc gggttttaag agttttaata agttttaaag agtttttaggc      5100
ggaaaaatcg cctttttttct cttttatatc agtcacttac atgtgtgacc ggttcccaat      5160
gtacggcttt gggttcccaa tgtacgggtt ccggttccca atgtacggct ttgggttccc      5220
aatgtacgtg ctatccacag gaaagagacc ttttcgacct ttttcccctg ctagggcaat      5280
ttgccctagc atctgctccg tacattagga accggcggat gcttcgccct cgatcaggtt      5340
gcggtagcgc atgactagga tcgggccagc ctgccccgcc tcctccttca aatcgtactc      5400
cggcaggtca tttgacccga tcagcttgcg cacggtgaaa cagaacttct tgaactctcc      5460
ggcgctgcca ctgcgttcgt agatcgtctt gaacaaccat ctggcttctg ccttgcctgc      5520
ggcgcggcgt gccaggcggt agagaaaacg gccgatgccg ggatcgatca aaaagtaatc      5580
ggggtgaacc gtcagcacgt ccgggttctt gccttctgtg atctcgcggt acatccaatc      5640
agctagctcg atctcgatgt actccggccg cccggtttcg ctctttacga tcttgtagcg      5700
gctaatcaag gcttcaccct cggataccgt caccaggcgg ccgttcttgg ccttcttcgt      5760
acgctgcatg gcaacgtgcg tggtgtttaa ccgaatgcag gtttctacca ggtcgtcttt      5820
ctgctttccg ccatcggctc gccggcagaa cttgagtacg tccgcaacgt gtggacggaa      5880
cacgcggccg gcttgtctc ccttcccttc ccggtatcgg ttcatggatt cggttagatg      5940
ggaaaccgcc atcagtacca ggtcgtaatc ccacacactg gccatgccgg ccggccctgc      6000
ggaaacctct acgtgcccgt ctggaagctc gtagcggatc acctcgccag ctcgtcggtc      6060
acgcttcgac agacggaaaa cggccacgtc catgatgctg cgactatcgc gggtgcccac      6120
gtcatagagc atcggaacga aaaaatctgg ttgctcgtcg cccttgggcg gcttcctaat      6180
cgacggcgca ccggctgccg gcggttgccg ggattctttg cggattcgat cagcggccgc      6240
ttgccacgat tcaccgggc gtgcttctgc ctcgatgcgt tgccgctggg cggcctgcgc      6300
ggccttcaac ttctccacca ggtcatcacc cagcgccgcg ccgatttgta ccgggccgga      6360
tggtttgcga ccgtcacgcc gattcctcgg gcttgggggt tccagtgcca ttgcagggcc      6420
ggcagacaac ccagccgctt acgcctggcc aaccgcccgt tcctccacac atggggcatt      6480
ccacggcgtc ggtgcctggt tgttcttgat tttccatgcc gcctccttta gccgctaaaa      6540
ttcatctact catttattca tttgctcatt tactctggta gctgcgcgat gtattcagat      6600
agcagctcgg taatggtctt gccttggcgt accgcgtaca tcttcagctt ggtgtgatcc      6660
tccgccggca actgaaagtt gacccgcttc atggctggcg tgtctgccag gctggccaac      6720
gttgcagcct tgctgctgcg tgcgctcgga cggccggcac ttagcgtgtt tgtgcttttg      6780
ctcatttttct ctttacctca ttaactcaaa tgagttttga tttaatttca gcggccagcg      6840
cctggacctc gcgggcagcg tcgccctcgg gttctgattc aagaacggtt gtgccggcgg      6900
cggcagtgcc tgggtagctc acgcgctgcg tgatacggga ctcaagaatg ggcagctcgt      6960
acccggccag cgcctcggca acctcaccgc cgatgcgcgt gcctttgatc gcccgcgaca      7020
cgacaaaggc cgcttgtagc cttccatccg tgaccctcaat gcgctgctta accagctcca      7080
```

```
ccaggtcggc ggtggcccat atgtcgtaag ggcttggctg caccggaatc agcacgaagt    7140
cggctgcctt gatcgcggac acagccaagt ccgccgcctg gggcgctccg tcgatcacta    7200
cgaagtcgcg ccggccgatg gccttcacgt cgcggtcaat cgtcgggcgg tcgatgccga    7260
caacggttag cggttgatct tcccgcacgg ccgcccaatc gcgggcactg ccctggggat    7320
cggaatcgac taacagaaca tcggccccgg cgagttgcag ggcgcgggct agatgggttg    7380
cgatggtcgt cttgcctgac ccgcctttct ggttaagtac agcgataacc ttcatgcgtt    7440
cccettgcgt atttgtttat ttactcatcg catcatatac gcagcgaccg catgacgcaa    7500
gctgttttac tcaaatacac atcacctttt tagacggcgg cgctcggttt cttcagcggc    7560
caagctggcc ggccaggccg ccagcttggc atcagacaaa ccggccagga tttcatgcag    7620
ccgcacggtt gagacgtgcg cgggcggctc gaacacgtac ccggccgcga tcatctccgc    7680
ctcgatctct tcggtaatga aaaacggttc gtcctggccg tcctggtgcg gtttcatgct    7740
tgttcctctt ggcgttcatt tcggcgccgccaggcgt cggcctcggt caatgcgtcc    7800
tcacggaagg caccgcgccg cctggcctcg gtgggcgtca cttcctcgct gcgctcaagt    7860
gcgcggtaca gggtcgagcg atgcacgcca agcagtgcag ccgcctcttt cacggtgcgg    7920
ccttcctggt cgatcagctc gcgggcgtgc gcgatctgtg ccggggtgag ggtagggcgg    7980
gggccaaact tcacgcctcg ggccttggcg gcctcgcgcc cgctccgggt gcggtcgatg    8040
attagggaac gctcgaactc ggcaatgccg gcgaacacgg tcaacaccat gcggccggcc    8100
ggcgtggtgg tgtcggccca cggctctgcc aggctacgca ggcccgcgcc ggcctcctgg    8160
atgcgctcgg caatgtccag taggtcgcgg gtgctgcggg ccaggcggtc tagcctggtc    8220
actgtcacaa cgtcgccagg gcgtaggtgg tcaagcatcc tggccagctc cgggcggtcg    8280
cgcctggtgc cggtgatctt ctcggaaaac agcttggtgc agccggccgc gtgcagttcg    8340
gcccgttggt tggtcaagtc ctggtcgtcg gtgctgacgc gggcatagcc cagcaggcca    8400
gcggcggcgc tcttgttcat ggcgtaatgt ctccggttct agtcgcaagt attctacttt    8460
atgcgactaa acacgcgac aagaaaacgc caggaaaagg gcagggcggc agcctgtcgc    8520
gtaacttagg acttgtgcga catgtcgttt tcagaagacg gctgcactga acgtcagaag    8580
ccgactgcac tatagcagcg gaggggttgg atcaaagtac tttgatcccg aggggaaccc    8640
tgtggttggc atgcacatac aaatggacga acggataaac ctttcacgc cctttaaat    8700
atccgttatt ctaataaacg ctcttttctc ttaggtttac ccgccaatat atcctgtcaa    8760
acactgcaaa aacgcaatca cacacagtgg acccaaaagc catgcacaac aacacgtact    8820
caccaaggtg caatcgtgct gcccaaaaac attcaccaac tcaatccatg atgagcccac    8880
acatttgttg tttgtaacca aatctcaaac gcggtgttct ctttggaaag caaccatatc    8940
agcatatcac actatctagt ctcttggatc atgcatgcgc aaccaaaaga caacacataa    9000
agtatccttt cgaaagcaat gtccaagtcc atcaaataaa attgagacaa aatgcaacct    9060
caccccactt cactatccat ggctgatcaa gatcgccgcg tccatgtagg tctaaatgcc    9120
atgcacatca acacgtactc aacatgcagc ccaaattgct caccatcgct caacacattt    9180
cttgttaatt tctaagtaca ctgcctatgc gactctaact cgatcacaac catcttccgt    9240
cacatcaatt ttgttcaatt caacacccgt caacttgcat gccacccat gcatgcaagt    9300
taacaagagc tatatctctt ctatgactat aaatacccgc aatctcggtc caggttttca    9360
tcatcgagaa ctagttcaat atcctagtat accttaataa ataatttaat atactcctaa    9420
```

```
taacttcgta tagcatacat tatacgaagt tatgaattaa atccgggcgg aatgaaagcg    9480
ttaacggcca ggcaacaaga ggtgtttgat ctcatccgtg atcacatcag ccagacaggt    9540
atgccgccga cgcgtgcgga aatcgcgcag cgtttggggt tccgttcccc aaacgcggct    9600
gaagaacatc tgaaggcgct ggcacgcaaa ggcgttattg aaattgtttc cggcgcatca    9660
cgcgggattc gtctgttgca ggaagaggaa gaagggttgc cgctggtagg tcgtgtggct    9720
gccggtgaac cgtcgagcgc cccccgacc gatgtcagcc tggggacga gctccactta     9780 gacggcgagg acgtggcgat ggcgcatgcc gacgcgctag acgatttcga tctggacatg    9840
ttgggggacg gggattcccc gggtccggga tttacccccc acgactccgc ccctacggc    9900 gctctggata tggccgactt cgagtttgag cagatgttta ccgatgccct tggaattgac    9960
gagtacggtg gggatccgtc tgctggagac atgagagctg ccaacctttg gccaagcccg   10020
ctcatgatca aacgctctaa gaagaacagc ctggccttgt ccctgacggc cgaccagatg   10080
gtcagtgcct tgttggatgc tgagcccccc atactctatt ccgagtatga tcctaccaga   10140
cccttcagtg aagcttcgat gatgggctta ctgaccaacc tggcagacag ggagctggtt   10200
cacatgatca actgggcgaa gagggtgcca ggctttgtgg atttgacccc ccatgatcag   10260
gtccaccttc tagaatgtgc ctggctagag atcctgatga ttggtctcgt ctggcgctcc   10320
atggagcacc cagtgaagct actgtttgct cctaacttgc tcttggacag gaaccaggga   10380
aaatgtgtag agggcatggt ggagatcttc gacatgctgc tggctacatc atctcggttc   10440
cgcatgatga atctgcaggg agaggagttt gtgtgcctca aatctattat tttgcttaat   10500
tctggagtgt acacatttct gtccagcacc ctgaagtctc tggaagagaa ggaccatatc   10560
caccgagtcc tggacaagat cacagacact tgatccacc tgatggccaa ggcaggcctg   10620
accctgcagc agcagcacca gcggctggcc cagctcctcc tcatcctctc ccacatcagg   10680
cacatgagta acaaaggcat ggagcatctg tacagcatga agtgcaagaa cgtggtgccc   10740
ctctatgacc tgctgctgga gatgctggac gcccaccgcc tacatgcgcc cactagccgt   10800 ggagggcat ccgtggagga gacggaccaa agccacttgg ccactgcggg ctctacttca    10860
tcgcattcct tgcaaaagta ttacatcacg gggaggcag agggtttccc tgccacagtc    10920
tgagagctcc ctggcgaatt cccagagatg ttagctgaaa tcatcactaa tcagatacca   10980
aaatattcaa atgaaatat caaaaagctt ctgtttcatc aaaatgact cgacctaact     11040 gagtaagcta gcttgttcga gtattatggc attgggaaaa ctgttttct tgtaccattt    11100 gttgtgcttg taatttactg tgttttttat tcggttttcg ctatcgaact gtgaaatgga   11160
aatggatgga gaagagttaa tgaatgatat ggtcccttttg ttcattctca aattaatatt   11220
atttgttttt tctcttattt gttgtgtgtt gaatttgaaa ttataagaga tatgcaaaca   11280
ttttgttttg agtaaaaatg tgtcaaatcg tggcctctaa tgaccgaagt taatatgagg   11340
agtaaaacat cccaaacaag cttggaaact gaaggcggga aacgacaatc tgatcatgag   11400
cggagaatta agggagtcac gttatgaccc ccgccgatga cgcgggacaa gccgttttac   11460
gtttggaact gacagaaccg caacgattga aggagccact cagccgcggg tttctggagt   11520
ttaatgagct aagcacatac gtcagaaacc attattcgc gttcaaaagt cgcctaaggt    11580
cactatcagc tagcaaatat ttcttgtcaa aaatgctcca ctgacgttcc ataaattccc   11640
ctcggtatcc aattagagtc tcatattcac tctcaatcca ataatctgc accggatccc    11700 ctagaatgaa aaagcctgaa ctcaccgcga cgtctgtcga gaagtttctg atcgaaagt    11760 tcgacagcgt ctccgacctg atgcagctct cggagggcga agaatctcgt gctttcagct   11820
```

```
tcgatgtagg agggcgtgga tatgtcctgc gggtaaatag ctgcgccgat ggtttctaca   11880
aagatcgtta tgtttatcgg cactttgcat cggccgcgct cccgattccg gaagtgcttg   11940
acattgggga attcagcgag agcctgacct attgcatctc ccgccgtgca cagggtgtca   12000
cgttgcaaga cctgcctgaa accgaactgc ccgctgttct gcagccggtc gcggaggcca   12060
tggatgcgat cgctgcggcc gatcttagcc agacgagcgg gttcggccca ttcggaccgc   12120
aaggaatcgg tcaatacact acatggcgtg atttcatatg cgcgattgct gatccccatg   12180
tgtatcactg gcaaactgtg atggacgaca ccgtcagtgc gtccgtcgcg caggctctcg   12240
atgagctgat gctttgggcc gaggactgcc ccgaagtccg gcacctcgtg cacgcggatt   12300
tcggctccaa caatgtcctg acggacaatg ccgcataac agcggtcatt gactggagcg     12360
aggcgatgtt cggggattcc caatacgagg tcgccaacat cttcttctgg aggccgtggt   12420
tggcttgtat ggagcagcag acgcgctact tcgagcggag gcatccggag cttgcaggat   12480
cgccgcggct ccgggcgtat atgctccgca ttggtcttga ccaactctat cagagcttgg   12540
ttgacggcaa tttcgatgat gcagcttggg cgcagggtcg atgcgacgca atcgtccgat   12600
ccggagccgg gactgtcggg cgtacacaaa tcgcccgcag aagcgcggcc gtctggaccg   12660
atggctgtgt agaagtactc gccgatagtg aaaccgacg ccccagcact cgtccgaggg    12720
caaaggaata gcgatcgttc aaacatttgg caataaagtt tcttaagatt gaatcctgtt   12780
gccggtcttg cgatgattat catataattt ctgttgaatt acgttaagca tgtaataatt   12840
aacatgtaat gcatgacgtt atttatgaga tgggtttta tgattagagt cccgcaatta    12900
tacatttaat acgcgataga aaacaaaata tagcgcgcaa actaggataa attatcgcgc   12960
gcggtgtcat ctatgttact agatcgggga attgatcccc cctcgacagc ttgcatgcca   13020
gcttgggctg caggtcgagg ctaaaaaact aatcgcatta tcatcccctc gacgtactgt   13080
acatataacc actggtttta tatacagcag tactgtacat ataaccactg gttttatata   13140
cagcagtcga cgtactgtac atataaccac tggttttata tacagcagta ctgtacatat   13200
aaccactggt tttatataca gcagtcgagg taagattaga tatggatatg tatatggata   13260
tgtatatggt ggtaatgcca tgtaatatgc tcgactctag gatcttcgca agacccttcc   13320
tctatataag gaagttcatt tcatttggag aggacacgct gaagctagtc gactctagcc   13380
tcgacatgtc caatttactg accgtacacc aaaatttgcc tgcattaccg gtcgatgcaa   13440
cgagtgatga ggttcgcaag aacctgatgg acatgttcag ggatcgccag gcgttttctg   13500
agcatacctg gaaaatgctt ctgtccgttt gccggtcgtg ggcggcatgg tgcaagttga   13560 ataccggaa atggtttccc gcagaacctg aagatgttcg cgattatctt ctatatcttc     13620 aggcgcgcg tctggcagta aaactatcc agcaacattt gggccagcta acatgcttc      13680 atcgtcggtc cgggctgcca cgaccaagtg acagcaatgc tgtttcactg gttatgcggc   13740
ggatccgaaa agaaaacgtt gatgccggtg aacgtgcaaa acaggctcta gcgttcgaac   13800
gcactgattt cgaccaggta agtcttcttt tcctttactc tttacagaaa tggtaatctc   13860
agatatagta atggataaga tccaaaaatg acacttttaa ccaagattgt acgaagatct   13920 tttaaactc catttttat tttgacatct aaattggatt taactcggcc ttgctgtatt     13980
ttggcaggtt cgttcactca tggaaaatag cgatcgctgc caggatatac gtaatctggc   14040
atttctgggg attgcttata acaccctgtt acgtatagcc gaaattgcca ggatcagggt   14100
taaagatatc tcacgtactg acggtgggag aatgttaatc catattggca gaacgaaaac   14160
```

```
gctggttagc accgcaggtg tagagaaggc acttagcctg ggggtaacta aactggtcga    14220
gcgatggatt tccgtctctg gtgtagctga tgatccgaat aactacctgt tttgccgggt    14280
cagaaaaaat ggtgttgccg cgccatctgc caccagccag ctatcaactc gcgccctgga    14340
agggattttt gaagcaactc atcgattgat ttacggcgct aaggatgact ctggtcagag    14400
atacctggcc tggtctggac acagtgcccg tgtcggagcc gcgcgagata tggcccgcgc    14460
tggagtttca ataccggaga tcatgcaagc tggtggctgg accaatgtaa atattgtcat    14520
gaactatatc cgtaacctgg atagtgaaac aggggcaatg gtgcgcctgc tggaagatgg    14580
cgattagtaa gaattcgcat gcattcatca atattattca tgcggggaaa ggcaagatta    14640
atccaactgg caaatcatcc agcgtgattg gtaacttcag ttccagcgac ttgattcgtt    14700
ttggtgctac ccacgttttc aataaggacg agatggtgga gtaaagaagg agtgcgtcga    14760
agcagatcgt tcaaacattt ggcaataaag tttcttaaga ttgaatcctg ttgccggtct    14820
tgcgatgatt atcatataat ttctgttgaa ttacgttaag catgtaataa ttaacatgta    14880
atgcatgacg ttatttatga gatgggtttt tatgattaga gtcccgcaat tatacattta    14940
atacgcgata gaaaacaaaa tatagcgcgc aaactaggat aaattatcgc gcgcggtgtc    15000
atctatgtta ctagatcata acttcgtata gcatacatta tacgaagtta tagatcttcg    15060
acc                                                                   15063

<210> SEQ ID NO 17
<211> LENGTH: 21
<212> TYPE: DNA
<213> ORGANISM: Jatropha curcas

<400> SEQUENCE: 17
ggttgaggaa ggaggtggaa g                                              21

<210> SEQ ID NO 18
<211> LENGTH: 21
<212> TYPE: DNA
<213> ORGANISM: Jatropha curcas

<400> SEQUENCE: 18
ccaccattca cacttggtca g                                              21

<210> SEQ ID NO 19
<211> LENGTH: 22
<212> TYPE: DNA
<213> ORGANISM: Jatropha curcas

<400> SEQUENCE: 19
agcaatcaag cctatattgg gc                                             22

<210> SEQ ID NO 20
<211> LENGTH: 20
<212> TYPE: DNA
<213> ORGANISM: Jatropha curcas

<400> SEQUENCE: 20
ccagagaact cctcggttgg                                                20

<210> SEQ ID NO 21
<211> LENGTH: 18
<212> TYPE: DNA
<213> ORGANISM: Jatropha curcas

<400> SEQUENCE: 21
```

```
tggtgcatca tacggctc                                                18
```

<210> SEQ ID NO 22
<211> LENGTH: 20
<212> TYPE: DNA
<213> ORGANISM: Jatropha curcas

<400> SEQUENCE: 22

```
atgtgaacat tgatatcatg                                              20
```

<210> SEQ ID NO 23
<211> LENGTH: 19
<212> TYPE: DNA
<213> ORGANISM: Jatropha curcas

<400> SEQUENCE: 23

```
cttctccagc aacgggctc                                               19
```

<210> SEQ ID NO 24
<211> LENGTH: 19
<212> TYPE: DNA
<213> ORGANISM: Jatropha curcas

<400> SEQUENCE: 24

```
ggagttccgc ctgaggaag                                               19
```

<210> SEQ ID NO 25
<211> LENGTH: 24
<212> TYPE: DNA
<213> ORGANISM: Jatropha curcas

<400> SEQUENCE: 25

```
gaggctggat ctggcaaaca cgtt                                         24
```

<210> SEQ ID NO 26
<211> LENGTH: 25
<212> TYPE: DNA
<213> ORGANISM: Jatropha curcas

<400> SEQUENCE: 26

```
tgtgtaatga cctctagcaa aatta                                        25
```

<210> SEQ ID NO 27
<211> LENGTH: 21
<212> TYPE: DNA
<213> ORGANISM: Artificial Sequence
<220> FEATURE:
<223> OTHER INFORMATION: real-time PCR primer

<400> SEQUENCE: 27

```
tcaatccatg atgagcccac a                                            21
```

<210> SEQ ID NO 28
<211> LENGTH: 32
<212> TYPE: DNA
<213> ORGANISM: Artificial Sequence
<220> FEATURE:
<223> OTHER INFORMATION: real-time PCR primer

<400> SEQUENCE: 28

```
gtataagctt catgagtgtc tgtaatgtta tg                                32
```

<210> SEQ ID NO 29

```
<211> LENGTH: 26
<212> TYPE: DNA
<213> ORGANISM: Artificial Sequence
<220> FEATURE:
<223> OTHER INFORMATION: real-time PCR primer

<400> SEQUENCE: 29
gccgccacgt gccgccacgt gccgcc                                          26

<210> SEQ ID NO 30
<211> LENGTH: 24
<212> TYPE: DNA
<213> ORGANISM: Artificial Sequence
<220> FEATURE:
<223> OTHER INFORMATION: real-time PCR primer

<400> SEQUENCE: 30
tacttctaca cagccatcgg tcca                                            24

<210> SEQ ID NO 31
<211> LENGTH: 27
<212> TYPE: DNA
<213> ORGANISM: Artificial Sequence
<220> FEATURE:
<223> OTHER INFORMATION: real-time PCR primer

<400> SEQUENCE: 31
aaaaagcctg aactcaccgc gacgtct                                         27

<210> SEQ ID NO 32
<211> LENGTH: 15639
<212> TYPE: DNA
<213> ORGANISM: Artificial Sequence
<220> FEATURE:
<223> OTHER INFORMATION: pX8-JcFAD2-1 RNAi vector

<400> SEQUENCE: 32
ctagtcgatc caggcctccc agctttcgtc cgtatcatcg gtttcgacaa cgttcgtcaa      60
gttcaatgca tcagttttcat tgcccacaca ccagaatcct actaagtttg agtattatgg    120
cattggaaaa gctgttttct tctatcattt gttctgcttg taatttactg tgttctttca    180 gttttttgttt tcggacatca aaatgcaaat ggatggataa gagttaataa atgatatggt    240
ccttttgttc attctcaaat tattattatc tgttgtttttt actttaatgg ttgaattta    300 agtaagaaag gaactaacag tgtgatatta aggtgcaatg ttagacatat aaaacagtct    360
ttcacctctc tttggttatg tcttgaattg gtttgtttct tcacttatct gtgtaatcaa    420
gtttactatg agtctatgat caagtaatta tgcaatcaag ttaagtacag tataggcttt    480
ttgtgtcgag ggggtaccga gtcgaggaat tcactggccg tcgttttaca acgtcgtgac    540
tgggaaaacc ctggcgttac ccaacttaat cgccttgcag cacatccccc tttcgccagc    600
tggcgtaata gcgaagaggc ccgcaccgat cgcccttccc aacagttgcg cagcctgaat    660
ggcgggtacc gagctcgaat tcaattcggc gttaattcag tacattaaaa acgtccgcaa    720
tgtgttatta agttgtctaa gcgtcaattt gtttacacca caatatatcc tgccaccagc    780
cagccaacag ctccccgacc ggcagctcgg cacaaaatca ccactcgata caggcagccc    840
atcagtccgg gacggcgtca gcgggagagc cgttgtaagg cggcagactt tgctcatgtt    900
accgatgcta ttcggaagaa cggcaactaa gctgccgggt ttgaaacacg gatgatctcg    960
cggagggtag catgttgatt gtaacgatga cagagcgttg ctgcctgtga tcaattcggg   1020
cacgaaccca gtggacataa gcctcgttcg gttcgtaagc tgtaatgcaa gtagcgtaac   1080
```

-continued

```
tgccgtcacg caactggtcc agaaccttga ccgaacgcag cggtggtaac ggcgcagtgg    1140
cggttttcat ggcttcttgt tatgacatgt ttttttgggg tacagtctat gcctcgggca    1200
tccaagcagc aagcgcgtta cgccgtgggt cgatgtttga tgttatggag cagcaacgat    1260
gttacgcagc agggcagtcg ccctaaaaca aagttaaaca tcatggggga agcggtgatc    1320
gccgaagtat cgactcaact atcagaggta gttggcgtca tcgagcgcca tctcgaaccg    1380
acgttgctgg ccgtacattt gtacggctcc gcagtggatg gcggcctgaa gccacacagt    1440
gatattgatt tgctggttac ggtgaccgta aggcttgatg aaacaacgcg gcgagctttg    1500
atcaacgacc ttttggaaac ttcggcttcc cctggagaga gcgagattct ccgcgctgta    1560
gaagtcacca ttgttgtgca cgacgacatc attccgtggc gttatccagc taagcgcgaa    1620
ctgcaatttg gagaatggca gcgcaatgac attcttgcag gtatcttcga gccagccacg    1680
atcgacattg atctggctat cttgctgaca aaagcaagag aacatagcgt tgccttggta    1740
ggtccagcgg cggaggaact cttttgatccg gttcctgaac aggatctatt tgaggcgcta    1800
aatgaaacct taacgctatg gaactcgccg cccgactggg ctggcgatga gcgaaatgta    1860
gtgcttacgt tgtcccgcat ttggtacagc gcagtaaccg gcaaaatcgc gccgaaggat    1920
gtcgctgccg actgggcaat ggagcgcctg ccggcccagt atcagcccgt catacttgaa    1980
gctagacagg cttatcttgg acaagaagaa gatcgcttgg cctcgcgcgc agatcagttg    2040
gaagaatttg tccactacgt gaaaggcgag atcaccaagg tagtcggcaa ataatgtcta    2100
gctagaaatt cgttcaagcc gacgccgctt cgcggcgcgg cttaactcaa gcgttagatg    2160
cactaagcac ataattgctc acagccaaac tatcaggtca agtctgcttt tattattttt    2220
aagcgtgcat aataagccct acacaaattg gagagatatat catgcatgac caaaatccct    2280
taacgtgagt tttcgttcca ctgagcgtca gaccccgtag aaaagatcaa aggatcttct    2340
tgagatcctt ttttttctgcg cgtaatctgc tgcttgcaaa caaaaaaacc accgctacca    2400
gcggtggttt gtttgccgga tcaagagcta ccaactcttt ttccgaaggt aactggcttc    2460
agcagagcgc agataccaaa tactgtcctt ctagtgtagc cgtagttagg ccaccacttc    2520
aagaactctg tagcaccgcc tacataccte gctctgctaa tcctgttacc agtggctgct    2580
gccagtggcg ataagtcgtg tcttaccggg ttggactcaa gacgatagtt accggataag    2640
gcgcagcggt cgggctgaac ggggggttcg tgcacacagc ccagcttgga gcgaacgacc    2700
tacaccgaac tgagatacct acagcgtgag ctatgagaaa gcgccacgct tcccgaaggg    2760
agaaaggcgg acaggtatcc ggtaagcggc agggtcggaa caggagagcg cacgagggag    2820
cttccagggg gaaacgcctg gtatctttat agtcctgtcg ggtttcgcca cctctgactt    2880
gagcgtcgat ttttgtgatg ctcgtcaggg gggcggagcc tatggaaaaa cgccagcaac    2940
gcggcctttt tacggttcct ggccttttgc tggccttttg ctcacatgtt ctttcctgcg    3000
ttatcccctg attctgtgga taaccgtatt accgcctttg agtgagctga taccgctcgc    3060
cgcagccgaa cgaccgagcg cagcgagtca gtgagcgagg aagcggaaga gcgcctgatg    3120
cggtattttc tccttacgca tctgtgcggt atttcacacc gcatatggtg cactctcagt    3180
acaatctgct ctgatgccgc atagttaagc cagtatacac tccgctatcg ctacgtgact    3240
gggtcatggc tgcgcccga cacccgccaa cacccgctga cgcgccctga cgggcttgtc    3300
tgctcccggc atccgcttac agacaagctg tgaccgtctc cgggagctgc atgtgtcaga    3360
ggttttcacc gtcatcaccg aaacgcgcga ggcagggtgc cttgatgtgg gcgccggcgg    3420
```

-continued

```
tcgagtggcg acggcgcggc ttgtccgcgc cctggtagat tgcctggccg taggccagcc   3480
attttgagc  ggccagcggc cgcgataggc cgacgcgaag cggcggggcg tagggagcgc   3540
agcgaccgaa gggtaggcgc ttttgcagc  tcttcggctg tgcgctggcc agacagttat   3600
gcacaggcca ggcgggtttt aagagtttta ataagtttta aagagtttta ggcggaaaaa   3660
tcgcctttt  tctcttttat atcagtcact tacatgtgtg accggttccc aatgtacggc   3720
tttgggttcc caatgtacgg gttccggttc ccaatgtacg gctttgggtt cccaatgtac   3780
gtgctatcca caggaaagag accttttcga cctttttccc ctgctagggc aatttgccct   3840
agcatctgct ccgtacatta ggaaccggcg gatgcttcgc cctcgatcag gttgcggtag   3900
cgcatgacta ggatcgggcc agcctgcccc gcctcctcct tcaaatcgta ctccggcagg   3960
tcatttgacc cgatcagctt gcgcacggtg aaacagaact tcttgaactc tccggcgctg   4020
ccactgcgtt cgtagatcgt cttgaacaac catctggctt ctgccttgcc tgcggcgcgg   4080
cgtgccaggc ggtagagaaa acggccgatg ccgggatcga tcaaaaagta atcggggtga   4140
accgtcagca cgtccgggtt cttgccttct gtgatctcgc ggtacatcca atcagctagc   4200
tcgatctcga tgtactccgg ccgcccggtt tcgctcttta cgatcttgta gcggctaatc   4260
aaggcttcac cctcggatac cgtcaccagg cggccgttct tggccttctt cgtacgctgc   4320
atggcaacgt gcgtggtgtt taaccgaatg caggtttcta ccaggtcgtc tttctgcttt   4380
ccgccatcgg ctcgccggca gaacttgagt acgtccgcaa cgtgtggacg gaacacgcgg   4440
ccgggcttgt ctcccttccc ttccggtat  cggttcatgg attcggttag atgggaaacc   4500
gccatcagta ccaggtcgta atcccacaca ctggccatgc cggccggccc tgcgaaaacc   4560
tctacgtgcc cgtctggaag ctcgtagcgg atcacctcgc cagctcgtcg gtcacgcttc   4620
gacagacgga aaacggccac gtccatgatg ctgcgactat cgcgggtgcc cacgtcatag   4680
agcatcggaa cgaaaaaatc tggttgctcg tcgcccttgg gcggcttcct aatcgacggc   4740
gcaccggctg ccggcggttg ccgggattct ttgcggattc gatcagcggc cgcttgccac   4800
gattcaccgg ggcgtgcttc tgcctcgatg cgttgccgct gggcggcctg cgcggccttc   4860
aacttctcca ccaggtcatc acccagcgcc gcgccgattt gtaccgggcc ggatggtttg   4920
cgaccgtcac gccgattcct cgggcttggg ggttccagtg ccattgcagg gccggcagac   4980
aacccagccg cttacgcctg gccaaccgcc cgttcctcca cacatggggc attccacggc   5040
gtcggtgcct ggttgttctt gattttccat gccgcctcct ttagccgcta aaattcatct   5100
actcatttat tcatttgctc atttactctg gtagctgcgc gatgtattca gatagcagct   5160
cggtaatggt cttgccttgg cgtaccgcgt acatcttcag cttggtgtga tcctccgccg   5220
gcaactgaaa gttgacccgc ttcatggctg gcgtgtctgc caggctggcc aacgttgcag   5280
ccttgctgct gcgtgcgctc ggacggccgg cacttagcgt gtttgtgctt ttgctcattt   5340
tctctttacc tcattaactc aaatgagttt tgatttaatt tcagcggcca gcgcctggac   5400
ctcgcgggca gcgtcgccct cgggttctga ttcaagaacg gttgtgccgg cggcggcagt   5460
gcctgggtag ctcacgcgct gcgtgatacg ggactcaaga atgggcagct cgtacccggc   5520
cagcgcctcg gcaacctcac cgccgatgcg cgtgcctttg atcgcccgcg acacgacaaa   5580
ggccgcttgt agccttccat ccgtgacctc aatgcgctgc ttaaccagct ccaccaggtc   5640
ggcggtggcc catatgtcgt aagggcttgg ctgcaccgga atcagcacga agtcggctgc   5700
cttgatcgcg gacacagcca agtccgccgc ctggggcgct ccgtcgatca ctacgaagtc   5760
gcgccggccg atggccttca cgtcgcggtc aatcgtcggg cggtcgatgc cgacaacggt   5820
```

```
tagcggttga tcttcccgca cggccgccca atcgcgggca ctgccctggg gatcggaatc   5880
gactaacaga acatcggccc cggcgagttg cagggcgcgg gctagatggg ttgcgatggt   5940
cgtcttgcct gacccgcctt tctggttaag tacagcgata accttcatgc gttcccttg    6000 cgtatttgtt tatttactca tcgcatcata tacgcagcga ccgcatgacg caagctgttt   6060
tactcaaata cacatcacct ttttagacgg cggcgctcgg tttcttcagc ggccaagctg   6120
gccggccagg ccgccagctt ggcatcagac aaaccggcca ggatttcatg cagccgcacg   6180
gttgagacgt gcgcgggcgg ctcgaacacg tacccggccg cgatcatctc cgcctcgatc   6240
tcttcggtaa tgaaaaacgg ttcgtcctgg ccgtcctggt gcggtttcat gcttgttcct   6300
cttggcgttc attctcggcg gccgccaggg cgtcggcctc ggtcaatgcg tcctcacgga   6360
aggcaccgcg ccgcctggcc tcggtgggcg tcacttcctc gctgcgctca agtgcgcggt   6420
acagggtcga gcgatgcacg ccaagcagtg cagccgcctc tttcacggtg cggccttcct   6480
ggtcgatcag ctcgcgggcg tgcgcgatct gtgccgggt gagggtaggg cggggggccaa    6540 acttcacgcc tcgggccttg gcggcctcgc gcccgctccg ggtgcggtcg atgattaggg   6600
aacgctcgaa ctcggcaatg ccggcgaaca cggtcaacac catgcggccg ccggcgtgg    6660 tggtgtcggc ccacggctct gccaggctac gcaggcccgc gccggcctcc tggatgcgct   6720
cggcaatgtc cagtaggtcg cgggtgctgc gggccaggcg gtctagcctg gtcactgtca   6780
caacgtcgcc agggcgtagg tggtcaagca tcctggccag ctccgggcgg tcgcgcctgg   6840
tgccggtgat cttctcggaa aacagcttgg tgcagccggc cgcgtgcagt tcggcccgtt   6900
ggttggtcaa gtcctggtcg tcggtgctga cgcgggcata gcccagcagg ccagcggcgg   6960
cgctcttgtt catggcgtaa tgtctccggt tctagtcgca agtattctac tttatgcgac   7020
taaaacacgc gacaagaaaa cgccaggaaa agggcagggc ggcagcctgt cgcgtaactt   7080
aggacttgtg cgacatgtcg ttttcagaag acggctgcac tgaacgtcag aagccgactg   7140
cactatagca gcggaggggt tggatcaaag tactttaaag tactttaaag tactttaaag   7200
tactttgatc ccgagggaa ccctgtggtt ggcatgcaca tacaaatgga cgaacggata    7260 aacctttca cgcccttta aatatccgtt attctaataa acgctctttt ctcttaggtt    7320
tacccgccaa tatatcctgt caaacactga tagtttaaac caaaaacgca atcacacaca   7380
gtggacccaa aagccatgca caacaacacg tactcaccaa ggtgcaatcg tgctgcccaa   7440
aaacattcac caactcaatc catgatgagc ccacacattt gttgtttgta accaaatctc   7500
aaacgcggtg ttctctttgg aaagcaacca tatcagcata tcacactatc tagtctcttg   7560
gatcatgcat gcgcaaccaa aagacaacac ataaagtatc ctttcgaaag caatgtccaa   7620
gtccatcaaa taaaattgag acaaaatgca acctcacccc acttcactat ccatggctga   7680
tcaagatcgc cgcgtccatg taggtctaaa tgccatgcac atcaacacgt actcaacatg   7740
cagcccaaat tgctcaccat cgctcaacac atttcttgtt aatttctaag tacactgcct   7800
atgcgactct aactcgatca caaccatctt ccgtcacatc aattttgttc aattcaacac   7860
ccgtcaactt gcatgccacc ccatgcatgc aagttaacaa gagctatatc tcttctatga   7920
ctataaatac ccgcaatctc ggtccaggtt ttcatcatcg agaactagtt caatatccta   7980 gtataccctta ataaataatt taatatactc ctaataactt cgtatagcat acattatacg   8040
aagttatgaa ttaaatccgg gcggaatgaa agcgttaacg gccaggcaac aagaggtgtt   8100
tgatctcatc cgtgatcaca tcagccagac aggtatgccg ccgacgcgtg cggaaatcgc   8160
```

```
gcagcgtttg gggttccgtt ccccaaacgc ggctgaagaa catctgaagg cgctggcacg       8220
caaaggcgtt attgaaattg tttccggcgc atcacgcggg attcgtctgt tgcaggaaga       8280
ggaagaaggg ttgccgctgg taggtcgtgt ggctgccggt gaaccgtcga gcgcccccc        8340 gaccgatgtc agcctggggg acgagctcca cttagacggc gaggacgtgg cgatggcgca       8400
tgccgacgcg ctagacgatt tcgatctgga catgttgggg gacggggatt ccccgggtcc       8460
gggatttacc ccccacgact ccgccccta cggcgctctg gatatggccg acttcgagtt        8520
tgagcagatg tttaccgatg cccttggaat tgacgagtac ggtggggatc cgtctgctgg       8580
agacatgaga gctgccaacc tttggccaag cccgctcatg atcaaacgct taagaagaa        8640 cagcctggcc ttgtccctga cggccgacca gatggtcagt gccttgttgg atgctgagcc       8700
ccccatactc tattccgagt atgatcctac cagaccttc agtgaagctt cgatgatggg        8760
cttactgacc aacctggcag acagggagct ggttcacatg atcaactggg cgaagagggt       8820
gccaggcttt gtggatttga ccctccatga tcaggtccac cttctagaat gtgcctggct       8880
agagatcctg atgattggtc tcgtctggcg ctccatggag cacccagtga agctactgtt       8940
tgctcctaac ttgctcttgg acaggaacca gggaaaatgt gtagagggca tggtggagat       9000
cttcgacatg ctgctggcta catcatctcg gttccgcatg atgaatctgc agggagagga       9060
gtttgtgtgc ctcaaatcta ttattttgct taattctgga gtgtacacat ttctgtccag       9120
caccctgaag tctctggaag agaaggacca tatccaccga gtcctggaca agatcacaga       9180
cactttgatc cacctgatgg ccaaggcagg cctgaccctg cagcagcagc accagcggct       9240
ggcccagctc ctcctcatcc tctcccacat caggcacatg agtaacaaag gcatggagca       9300
tctgtacagc atgaagtgca agaacgtggt gcccctctat gacctgctgc tggagatgct       9360
ggacgcccac cgcctacatg cgcccactag ccgtggaggg gcatccgtgg aggagacgga       9420
ccaaagccac ttggccactg cgggctctac ttcatcgcat tccttgcaaa agtattacat       9480 cacggggag gcagagggtt tccctgccac agtctgagag ctccctggcg aattcccaga       9540
gatgttagct gaaatcatca ctaatcagat accaaaatat tcaaatggaa atatcaaaaa       9600
gcttctgttt catcaaaaat gactcgacct aactgagtaa gctagcttgt tcgagtatta       9660
tggcattggg aaaactgttt ttcttgtacc atttgttgtg cttgtaattt actgtgtttt       9720
ttattcggtt ttcgctatcg aactgtgaaa tggaatgga tggagaagag ttaatgaatg        9780
atatggtcct tttgttcatt ctcaaattaa tattatttgt tttttctctt atttgttgtg       9840
tgttgaattt gaaattataa gagatatgca aacattttgt tttgagtaaa aatgtgtcaa       9900
atcgtggcct ctaatgaccg aagttaatat gaggagtaaa acatcccaaa caagcttgga       9960
aactgaaggc gggaaacgac aatctgatca tgagcggaga attaagggag tcacgttatg      10020 accccgccg atgacgcggg acaagccgtt ttacgtttgg aactgacaga accgcaacga       10080
ttgaaggagc cactcagccg cgggtttctg gagtttaatg agctaagcac atacgtcaga      10140
aaccattatt gcgcgttcaa aagtcgccta aggtcactat cagctagcaa atatttcttg      10200
tcaaaaatgc tccactgacg ttccataaat tcccctcggt atccaattag agtctcatat      10260
tcactctcaa tccaaataat ctgcaccgga tccgctagag gatctcgacc tgcaagatcc      10320
cggggggcaa tgagatatga aaaagcctga actcaccgcg acgtctgtcg agaagtttct      10380
gatcgaaaag ttcgacagcg tctccgacct gatgcagctc tcggagggcg aagaatctcg      10440
tgctttcagc ttcgatgtag gagggcgtgg atatgtcctg cgggtaaata gctgcgccga      10500
tggtttctac aaagatcgtt atgtttatcg gcactttgca tcggccgcgc tcccgattcc      10560
```

```
ggaagtgctt gacattgggg aattcagcga gagcctgacc tattgcatct cccgccgtgc    10620
acagggtgtc acgttgcaag acctgcctga aaccgaactg cccgctgttc tgcagccggt    10680
cgcggaggcc atgatgcga tcgctgcggc cgatcttagc cagacgagcg ggttcggccc     10740
attcggaccg caaggaatcg gtcaatacac tacatggcgt gatttcatat gcgcgattgc    10800
tgatccccat gtgtatcact ggcaaactgt gatggacgac accgtcagtg cgtccgtcgc    10860
gcaggctctc gatgagctga tgctttgggc cgaggactgc cccgaagtcc ggcacctcgt    10920
gcacgcggat ttcggctcca acaatgtcct gacggacaat ggccgcataa cagcggtcat    10980
tgactggagc gaggcgatgt tcggggattc ccaatacgag gtcgccaaca tcttcttctg    11040
gaggccgtgg ttggcttgta tggagcagca gacgcgctac ttcgagcgga ggcatccgga    11100
gcttgcagga tcgccgcggc tccgggcgta tatgctccgc attggtcttg accaactcta    11160
tcagagcttg gttgacggca atttcgatga tgcagcttgg gcgcagggtc gatgcgacgc    11220
aatcgtccga tccggagccg ggactgtcgg gcgtacacaa atcgcccgca gaagcgcggc    11280
cgtctggacc gatggctgtg tagaagtact cgccgatagt ggaaaccgac gccccagcac    11340
tcgtccggga tcttggaggt gatgtaacat gatcacaagc tgatccccg aatttccccg     11400 atcgttcaaa catttggcaa taaagtttct taagattgaa tcctgttgcc ggtcttgcga    11460
tgattatcat ataatttctg ttgaattacg ttaagcatgt aataattaac atgtaatgca    11520
tgacgttatt tatgagatgg gttttatga ttagagtccc gcaattatac atttaatacg     11580
cgatagaaaa caaatatag cgcgcaaact aggataaatt atcgcgcgcg gtgtcatcta     11640
tgttactaga tcggggaatt gatccccct cgacagcttg catgccagct tgggctgcag     11700
gtcgaggcta aaaactaat cgcattatca tcccctcgac gtactgtaca tataaccact     11760
ggttttatat acagcagtac tgtacatata accactggtt ttatatacag cagtcgacgt    11820
actgtacata taaccactgg ttttatatac agcagtactg tacatataac cactggtttt    11880
atatacagca gtcgaggtaa gattagatat ggatatgtat atggatatgt atatggtggt    11940
aatgccatgt aatatgctcg actctaggat cttcgcaaga cccttcctct atataaggaa    12000
gttcatttca tttggagagg acacgctgaa gctagtcgac tctagcctcg acatgtccaa    12060
tttactgacc gtacaccaaa atttgcctgc attaccggtc gatgcaacga gtgatgaggt    12120
tcgcaagaac ctgatggaca tgttcaggga tcgccaggcg ttttctgagc atacctggaa    12180
aatgcttctg tccgtttgcc ggtcgtgggc ggcatggtgc aagttgaata accggaaatg    12240
gtttcccgca gaacctgaag atgttcgcga ttatcttcta tatcttcagg cgcgcggtct    12300
ggcagtaaaa actatccagc aacatttggg ccagctaaac atgcttcatc gtcggtccgg    12360
gctgccacga ccaagtgaca gcaatgctgt ttcactggtt atgcggcgga tccgaaaaga    12420
aaacgttgat gccggtgaac gtgcaaaaca ggctctagcg ttcgaacgca ctgatttcga    12480
ccaggtaagt cttctttcc tttactcttt acagaaatgg taatctcaga tatagtaatg      12540
gataagatcc aaaaatgaca cttttaacca agattgtacg aagatctttt taaactccat    12600
tttttatttt gacatctaaa ttggatttaa ctcggccttg ctgtattttg gcaggttcgt    12660
tcactcatgg aaaatagcga tcgctgccag gatatacgta atctggcatt tctggggatt    12720
gcttataaca ccctgttacg tatagccgaa attgccagga tcagggttaa agatatctca    12780
cgtactgacg gtgggagaat gttaatccat attggcagaa cgaaaacgct ggttagcacc    12840
gcaggtgtag agaaggcact tagcctgggg gtaactaaac tggtcgagcg atggatttcc    12900
```

```
gtctctggtg tagctgatga tccgaataac tacctgtttt gccgggtcag aaaaaatggt    12960
gttgccgcgc catctgccac cagccagcta tcaactcgcg ccctggaagg gattttttgaa    13020 gcaactcatc gattgattta cggcgctaag gatgactctg gtcagagata cctggcctgg    13080
tctggacaca gtgcccgtgt cggagccgcg cgagatatgg cccgcgctgg agtttcaata    13140
ccggagatca tgcaagctgg tggctggacc aatgtaaata ttgtcatgaa ctatatccgt    13200
aacctggata gtgaaacagg ggcaatggtg cgcctgctgg aagatggcga ttagtaagaa    13260
ttcgcatgca ttcatcaata ttattcatgc ggggaaaggc aagattaatc caactggcaa    13320
atcatccagc gtgattggta acttcagttc cagcgacttg attcgttttg gtgctaccca    13380
cgttttcaat aaggacgaga tggtggagta agaaggagt gcgtcgaagc agatcgttca    13440
aacatttggc aataaagttt cttaagattg aatcctgttg ccggtcttgc gatgattatc    13500
atataatttc tgttgaatta cgttaagcat gtaataatta acatgtaatg catgacgtta    13560
tttatgagat gggttttttat gattagagtc ccgcaattat acatttaata cgcgatagaa    13620
aacaaaatat agcgcgcaaa ctaggataaa ttatcgcgcg cggtgtcatc tatgttacta    13680
gatcataact tcgtatagca tacattatac gaagttatag atcttcgacc tcgagcacca    13740
ttcacacttg gtcaggtcaa gaaagctatc ccacctcatt gtttccagcg ttctgttctc    13800
cgctcattct cgtatgttgt ttatgacctg acccttgcct ttatctttta ttatgttgcc    13860
accaattact tccacctcct tcctcaaccc ctctcttatg tggcctggcc aatttactgg    13920
tccctccaag gctgtgtcct cactggcatt tgggttatag cacatgagtg tgggcatcat    13980
gcctttagtg actatcaatg gcttgatgac atagttggcc ttctcctcca ttcctgtctc    14040
cttgtccctt actttttcatg gaaacatagc catcgccgtc atcactctaa caccggttcc    14100
cttgagcgag atgaagtatt tgtccctaaa aagaaatcca acatccgctg gttctccaaa    14160
taccttaaca acctaccagg ccgcctattc actcttacca taacacttgc ccttggctgg    14220
ccgctatacc tagcatttaa tgtttcaggc aggcattatg accgatttgc ctgtcacttt    14280
gacccatatg gccctatcta caatgatcgc gagcgaactg agatattcat ttctgatgct    14340
ggtgttcttg ctgtcactta tggtctctac cgtcttgctc tagcaaaggg cttgcttgg    14400 gttatttgcg tttatggagt acctttgtta gtggtgagtg catttcttgt tatgatcaca    14460
tatctgcaac atactcatcc ttcattgccg cattatgatt cttctgagtg ggattggctg    14520
agaggcgcgc tcgcaactgt tgatagagat tacggaatct tgaacaaggt attccataac    14580
attacagaca ctcatggtaa taagatcttc aacacctaca ccattttttt aatcactact    14640
acccattgca ttgaacaaac ttccaagttc ttcttagctt cagattaaga aagtaccctt    14700
tcttggcttt gttgatgtgg taccattgtc cattgtcttg tgtgtttcca gggcacgact    14760
tcttcaagag cgcatgagtg tctgtaatgt tatggaatac cttgttcaag attccgtaat    14820
ctctatcaac agttgcgagc gcgcctctca gccaatccca ctcagaagaa tcataatgcg    14880
gcaatgaagg atgagtatgt tgcagatatg tgatcataac aagaaatgca ttcaccacta    14940
acaaaggtac tccataaacg caaataaccc aagcaaagcc ctttgctaga gcaagacggt    15000
agagaccata agtgacagca agaacaccag catcagaaat gaatatctca gttcgctcgc    15060
gatcattgta gatagggcca tatgggtcaa agtgacaggc aaatcggtca taatgcctgc    15120
ctgaaacatt aaatgctagg tatagcggcc agccaagggc aagtgttatg gtaagagtga    15180
ataggcggcc tggtaggttg ttaaggtatt tggagaacca gcggatgttg gatttcttt    15240 tagggacaaa tacttcatct cgctcaaggg aaccggtgtt agagtgatga cggcgatggc    15300
```

```
tatgtttcca tgaaaagtaa gggacaagga gacaggaatg gaggagaagg ccaactatgt    15360
catcaagcca ttgatagtca ctaaaggcat gatgcccaca ctcatgtgct ataacccaaa    15420
tgccagtgag gacacagcct tggagggacc agtaaattgg ccaggccaca taagagaggg    15480
gttgaggaag gaggtggaag taattggtgg caacataata aaagataaag gcaagggtca    15540
ggtcataaac aacatacgag aatgagcgga gaacagaacg ctggaaacaa tgaggtggga    15600
tagctttctt gacctgacca agtgtgaatg gtggatcca                          15639

<210> SEQ ID NO 33
<211> LENGTH: 15222
<212> TYPE: DNA
<213> ORGANISM: Artificial Sequence
<220> FEATURE:
<223> OTHER INFORMATION: pX7-JcFAD2-1 RNAi vector

<400> SEQUENCE: 33
ctagtcgatc caggcctccc agctttcgtc cgtatcatcg gtttcgacaa cgttcgtcaa      60
gttcaatgca tcagtttcat tgcccacaca ccagaatcct actaagtttg agtattatgg     120
cattggaaaa gctgttttct tctatcattt gttctgcttg taatttactg tgttctttca     180 gttttttgttt tcggacatca aaatgcaaat ggatggataa gagttaataa atgatatggt    240
ccttttgttc attctcaaat tattattatc tgttgttttt actttaatgg ttgaattta      300 agtaagaaag gaactaacag tgtgatatta aggtgcaatg ttagacatat aaaacagtct     360
ttcacctctc tttggttatg tcttgaattg gtttgtttct tcacttatct gtgtaatcaa     420
gtttactatg agtctatgat caagtaatta tgcaatcaag ttaagtacag tataggcttt     480
ttgtgtcgag ggggtaccga gtcgaggaat tcactggccg tcgttttaca acgtcgtgac     540
tgggaaaacc ctggcgttac ccaacttaat cgccttgcag cacatccccc tttcgccagc    600
tggcgtaata gcgaagaggc ccgcaccgat cgcccttccc aacagttgcg cagcctgaat    660
ggcgggtacc gagctcgaat tcaattcggc gttaattcag tacattaaaa acgtccgcaa    720
tgtgttatta agttgtctaa gcgtcaattt gtttacacca caatatatcc tgccaccagc    780
cagccaacag ctccccgacc ggcagctcgg cacaaaatca ccactcgata caggcagccc    840
atcagtccgg gacggcgtca gcgggagagc cgttgtaagg cggcagactt tgctcatgtt    900
accgatgcta ttcggaagaa cggcaactaa gctgccgggt ttgaaacacg gatgatctcg    960
cggagggtag catgttgatt gtaacgatga cagagcgttg ctgcctgtga tcaattcggg   1020
cacgaaccca gtggacataa gcctcgttcg gttcgtaagc tgtaatgcaa gtagcgtaac   1080
tgccgtcacg caactggtcc agaaccttga ccgaacgcag cggtggtaac ggcgcagtgg   1140
cggttttcat ggcttcttgt tatgacatgt tttttgggg tacagtctat gcctcgggca    1200
tccaagcagc aagcgcgtta cgccgtgggt cgatgtttga tgttatggag cagcaacgat   1260
gttacgcagc agggcagtcg ccctaaaaca aagttaaaca tcatggggga agcggtgatc   1320
gccgaagtat cgactcaact atcagaggta gttggcgtca tcgagcgcca tctcgaaccg   1380
acgttgctgg ccgtacattt gtacggctcc gcagtggatg gcggcctgaa gccacacagt   1440
gatattgatt tgctggttac ggtgaccgta aggcttgatg aaacaacgcg gcgagctttg   1500
atcaacgacc ttttggaaac ttcggcttcc cctggagaga gcgagattct ccgcgctgta   1560
gaagtcacca ttgttgtgca cgacgacatc attccgtggc gttatccagc taagcgcgaa   1620
ctgcaatttg gagaatggca gcgcaatgac attcttgcag gtatcttcga gccagccacg   1680
```

```
atcgacattg atctggctat cttgctgaca aaagcaagag aacatagcgt tgccttggta    1740
ggtccagcgg cggaggaact ctttgatccg gttcctgaac aggatctatt tgaggcgcta    1800
aatgaaacct taacgctatg gaactcgccg cccgactggg ctggcgatga gcgaaatgta    1860
gtgcttacgt tgtcccgcat ttggtacagc gcagtaaccg gcaaaatcgc gccgaaggat    1920
gtcgctgccg actgggcaat ggagcgcctg ccggcccagt atcagcccgt catacttgaa    1980
gctagacagg cttatcttgg acaagaagaa gatcgcttgg cctcgcgcgc agatcagttg    2040
gaagaatttg tccactacgt gaaaggcgag atcaccaagg tagtcggcaa ataatgtcta    2100
gctagaaatt cgttcaagcc gacgccgctt cgcggcgcgg cttaactcaa gcgttagatg    2160
cactaagcac ataattgctc acagccaaac tatcaggtca agtctgcttt tattattttt    2220
aagcgtgcat aataagccct acacaaattg gagagatatat catgcatgac caaaatccct    2280
taacgtgagt tttcgttcca ctgagcgtca gaccccgtag aaaagatcaa aggatcttct    2340
tgagatcctt ttttctgcg cgtaatctgc tgcttgcaaa caaaaaaacc accgctacca    2400
gcggtggttt gtttgccgga tcaagagcta ccaactcttt ttccgaaggt aactggcttc    2460
agcagagcgc agataccaaa tactgtcctt ctagtgtagc cgtagttagg ccaccacttc    2520
aagaactctg tagcaccgcc tacatacctc gctctgctaa tcctgttacc agtggctgct    2580
gccagtggcg ataagtcgtg tcttaccggg ttggactcaa gacgatagtt accggataag    2640
gcgcagcggt cgggctgaac ggggggttcg tgcacacagc ccagcttgga gcgaacgacc    2700
tacaccgaac tgagatacct acagcgtgag ctatgagaaa gcgccacgct cccgaaggg    2760
agaaaggcgg acaggtatcc ggtaagcggc agggtcggaa caggagagcg cacgagggag    2820
cttccagggg gaaacgcctg gtatctttat agtcctgtcg ggtttcgcca cctctgactt    2880
gagcgtcgat ttttgtgatg ctcgtcaggg gggcggagcc tatggaaaaa cgccagcaac    2940
gcggcctttt tacggttcct ggccttttgc tggccttttg ctcacatgtt ctttcctgcg    3000
ttatcccctg attctgtgga taaccgtatt accgcctttg agtgagctga taccgctcgc    3060
cgcagccgaa cgaccgagcg cagcgagtca gtgagcgagg aagcggaaga gcgcctgatg    3120
cggtattttc tccttacgca tctgtgcggt atttcacacc gcatatggtg cactctcagt    3180
acaatctgct ctgatgccgc atagttaagc cagtatacac tccgctatcg ctacgtgact    3240
gggtcatggc tgcgccccga cacccgccaa cacccgctga cgcgccctga cgggcttgtc    3300
tgctcccggc atccgcttac agacaagctg tgaccgtctc cgggagctgc atgtgtcaga    3360
ggttttcacc gtcatcaccg aaacgcgcga ggcagggtgc cttgatgtgg gcgccggcgg    3420
tcgagtggcg acggcgcggc ttgtccgcgc cctggtagat tgcctggccg taggccagcc    3480
atttttgagc ggccagcggc cgcgataggc cgacgcgaag cggcggggcg tagggagcgc    3540
agcgaccgaa gggtaggcgc ttttgcagc tcttcggctg tgcgctggcc agacagttat    3600
gcacaggcca ggcgggtttt aagagttta ataagtttta aagagttta ggcggaaaaa    3660
tcgccttttt tctcttttat atcagtcact tacatgtgtg accggttccc aatgtacggc    3720
tttgggttcc caatgtacgg gttccggttc ccaatgtacg gctttgggtt cccaatgtac    3780
gtgctatcca caggaaagag accttttcga ccttttcccc tgctagggc aatttgccct    3840
agcatctgct ccgtacatta ggaaccggcg gatgcttcgc cctcgatcag gttgcggtag    3900
cgcatgacta ggatcgggcc agcctgcccc gcctcctcct tcaaatcgta ctccggcagg    3960
tcatttgacc cgatcagctt gcgcacggtg aaacagaact tcttgaactc tccggcgctg    4020
ccactgcgtt cgtagatcgt cttgaacaac catctggctt ctgccttgcc tgcggcgcgg    4080
```

```
cgtgccaggc ggtagagaaa acggccgatg ccgggatcga tcaaaaagta atcggggtga   4140
accgtcagca cgtccgggtt cttgccttct gtgatctcgc ggtacatcca atcagctagc   4200
tcgatctcga tgtactccgg ccgcccggtt tcgctcttta cgatcttgta gcggctaatc   4260
aaggcttcac cctcggatac cgtcaccagg cggccgttct tggccttctt cgtacgctgc   4320
atggcaacgt gcgtggtgtt taaccgaatg caggtttcta ccaggtcgtc tttctgcttt   4380
ccgccatcgg ctcgccggca gaacttgagt acgtccgcaa cgtgtggacg gaacacgcgg   4440
ccgggcttgt ctcccttccc ttccggtat cggttcatgg attcggttag atgggaaacc   4500
gccatcagta ccaggtcgta atcccacaca ctggccatgc cggccggccc tgcggaaacc   4560
tctacgtgcc cgtctggaag ctcgtagcgg atcacctcgc cagctcgtcg gtcacgcttc   4620
gacagacgga aaacgccac gtccatgatg ctgcgactat cgcgggtgcc cacgtcatag   4680
agcatcggaa cgaaaaaatc tggttgctcg tcgcccttgg gcggcttcct aatcgacggc   4740
gcaccggctg ccggcggttg ccgggattct ttgcggattc gatcagcggc cgcttgccac   4800
gattcaccgg ggcgtgcttc tgcctcgatg cgttgccgct gggcggcctg cgcggccttc   4860
aacttctcca ccaggtcatc acccagcgcc gcgccgattt gtaccgggcc ggatggtttg   4920
cgaccgtcac gccgattcct cgggcttggg ggttccagtg ccattgcagg gccggcagac   4980
aacccagccg cttacgcctg gccaaccgcc cgttcctcca cacatggggc attccacggc   5040
gtcggtgcct ggttgttctt gattttccat gccgcctcct ttagccgcta aaattcatct   5100
actcatttat tcatttgctc atttactctg gtagctgcgc gatgtattca gatagcagct   5160
cggtaatggt cttgccttgg cgtaccgcgt acatcttcag cttggtgtga tcctccgccg   5220
gcaactgaaa gttgacccgc ttcatggctg gcgtgtctgc caggctggcc aacgttgcag   5280
ccttgctgct gcgtgcgctc ggacggccgg cacttagcgt gtttgtgctt ttgctcattt   5340
tctctttacc tcattaactc aaatgagttt tgatttaatt tcagcggcca gcgcctggac   5400
ctcgcgggca gcgtcgccct cgggttctga ttcaagaacg gttgtgccgg cggcggcagt   5460
gcctgggtag ctcacgcgct gcgtgatacg ggactcaaga atgggcagct cgtacccggc   5520
cagcgcctcg gcaacctcac cgccgatgcg cgtgcctttg atcgcccgcg acacgacaaa   5580
ggccgcttgt agccttccat ccgtgacctc aatgcgctgc ttaaccagct ccaccaggtc   5640
ggcggtggcc catatgtcgt aagggcttgg ctgcaccgga atcagcacga agtcggctgc   5700
cttgatcgcg gacacagcca agtccgccgc ctggggcgct ccgtcgatca ctacgaagtc   5760
gcgccggccg atggccttca cgtcgcggtc aatcgtcggg cggtcgatgc cgacaacggt   5820
tagcggttga tcttcccgca cggccgccca atcgcgggca ctgccctggg gatcggaatc   5880
gactaacaga acatcggccc cggcgagttg cagggcgcgg gctagatggg ttgcgatggt   5940
cgtcttgcct gacccgcctt tctggttaag tacagcgata accttcatgc gttcccttg   6000 cgtatttgtt tatttactca tcgcatcata tacgcagcga ccgcatgacg caagctgttt   6060
tactcaaata cacatcacct ttttagacgg cggcgctcgg tttcttcagc ggccaagctg   6120
gccggccagg ccgccagctt ggcatcagac aaaccggcca ggatttcatg cagccgcacg   6180
gttgagacgt gcgcgggcgg ctcgaacacg tacccggccg cgatcatctc cgcctcgatc   6240
tcttcggtaa tgaaaaacgg ttcgtcctgg ccgtcctggt gcggtttcat gcttgttcct   6300
cttggcgttc attctcggcg gccgccaggg cgtcggcctc ggtcaatgcg tcctcacgga   6360
aggcaccgcg ccgcctggcc tcggtgggcg tcacttcctc gctgcgctca agtgcgcggt   6420
```

| | |
|---|---|
| acagggtcga gcgatgcacg ccaagcagtg cagccgcctc tttcacggtg cggccttcct | 6480 |
| ggtcgatcag ctcgcgggcg tgcgcgatct gtgccgggt gagggtaggg cgggggccaa | 6540 |
| acttcacgcc tcgggccttg gcggcctcgc gcccgctccg ggtgcggtcg atgattaggg | 6600 |
| aacgctcgaa ctcggcaatg ccggcgaaca cggtcaacac catgcggccg gccggcgtgg | 6660 |
| tggtgtcggc ccacggctct gccaggctac gcaggcccgc gccggcctcc tggatgcgct | 6720 |
| cggcaatgtc cagtaggtcg cgggtgctgc gggccaggcg gtctagcctg gtcactgtca | 6780 |
| caacgtcgcc agggcgtagg tggtcaagca tcctggccag ctccgggcgg tcgcgcctgg | 6840 |
| tgccggtgat cttctcggaa aacagcttgg tgcagccggc cgcgtgcagt tcggcccgtt | 6900 |
| ggttggtcaa gtcctggtcg tcggtgctga cgcgggcata gcccagcagg ccagcggcgg | 6960 |
| cgctcttgtt catggcgtaa tgtctccggt tctagtcgca agtattctac tttatgcgac | 7020 |
| taaaacacgc gacaagaaaa cgccaggaaa agggcagggc ggcagcctgt cgcgtaactt | 7080 |
| aggacttgtg cgacatgtcg ttttcagaag acggctgcac tgaacgtcag aagccgactg | 7140 |
| cactatagca gcggagggt tggatcaaag tactttaaag tactttaaag tactttaaag | 7200 |
| tactttgatc ccgaggggaa ccctgtggtt ggcatgcaca tacaaatgga cgaacggata | 7260 |
| aacctttca cgcccttta aatatccgtt attctaataa cgctctttt ctcttaggtt | 7320 |
| tacccgccaa tatatcctgt caaacactga tagtttaaac tgaaggcggg aaacgacaat | 7380 |
| ctgatccaag ctcaagctaa gcttgcatgc ctgcaggata tcgtggatcc aagcttgcca | 7440 |
| cgtgccgcca cgtgccgcca cgtgccgcca cgtgcctcta gaggatccat ctccactgac | 7500 |
| gtaagggatg acgcacaatc ccactatcct tcgcaagacc cttcctctat ataaggaagt | 7560 |
| tcatttcatt tggagaggac acgctgggat cccctaataa cttcgtatag catacattat | 7620 |
| acgaagttat gaattaaatc cgggcggaat gaaagcgtta acggccaggc aacaagaggt | 7680 |
| gtttgatctc atccgtgatc acatcagcca gacaggtatg ccgccgacgc gtgcggaaat | 7740 |
| cgcgcagcgt ttggggttcc gttccccaaa cgcggctgaa gaacatctga aggcgctggc | 7800 |
| acgcaaaggc gttattgaaa ttgtttccgg cgcatcacgc gggattcgtc tgttgcagga | 7860 |
| agaggaagaa gggttgccgc tggtaggtcg tgtggctgcc ggtgaaccgt cgagcgcccc | 7920 |
| cccgaccgat gtcagcctgg gggacgagct ccacttagac ggcgaggacg tggcgatggc | 7980 |
| gcatgccgac gcgctagacg atttcgatct ggacatgttg ggggacgggg attccccggg | 8040 |
| tccgggattt accccccacg actccgcccc ctacggcgct ctggatatgg ccgacttcga | 8100 |
| gtttgagcag atgtttaccg atgcccttgg aattgacgag tacggtgggg atccgtctgc | 8160 |
| tggagacatg agagctgcca acctttggcc aagcccgctc atgatcaaac gctctaagaa | 8220 |
| gaacagcctg gccttgtccc tgacggccga ccagatggtc agtgccttgt tggatgctga | 8280 |
| gccccccata ctctattccg agtatgatcc taccagaccc ttcagtgaag cttcgatgat | 8340 |
| gggcttactg accaacctgg cagacaggga gctggttcac atgatcaact gggcgaagag | 8400 |
| ggtgccaggc tttgtggatt tgaccctcca tgatcaggtc caccttctag aatgtgcctg | 8460 |
| gctagagatc ctgatgattg gtctcgtctg gcgctccatg gagcacccag tgaagctact | 8520 |
| gtttgctcct aacttgctct tggacaggaa ccagggaaaa tgtgtagagg gcatggtgga | 8580 |
| gatcttcgac atgctgctgg ctacatcatc tcggttccgc atgatgaatc tgcagggaga | 8640 |
| ggagtttgtg tgcctcaaat ctattatttt gcttaattct ggagtgtaca catttctgtc | 8700 |
| cagcaccctg aagtctctgg aagagaagga ccatatccac cgagtcctgg acaagatcac | 8760 |
| agacactttg atccacctga tggccaaggc aggcctgacc ctgcagcagc agcaccagcg | 8820 |

```
gctggcccag ctcctcctca tcctctccca catcaggcac atgagtaaca aaggcatgga    8880
gcatctgtac agcatgaagt gcaagaacgt ggtgccctc  tatgacctgc tgctggagat    8940
gctggacgcc caccgcctac atgcgcccac tagccgtgga ggggcatccg tggaggagac    9000
ggaccaaagc cacttggcca ctgcgggctc tacttcatcg cattccttgc aaaagtatta    9060
catcacgggg gaggcagagg gtttccctgc cacagtctga gagctccctg gcgaattccc    9120
agagatgtta gctgaaatca tcactaatca gataccaaaa tattcaaatg gaaatatcaa    9180
aaagcttctg tttcatcaaa aatgactcga cctaactgag taagctagct tgttcgagta    9240
ttatggcatt gggaaaactg ttttttcttgt accatttgtt gtgcttgtaa tttactgtgt    9300
tttttattcg gttttcgcta tcgaactgtg aaatggaaat ggatggagaa gagttaatga    9360
atgatatggt cctttttgttc attctcaaat taatattatt tgttttttct cttatttgtt    9420
gtgtgttgaa tttgaaatta taagagatat gcaaacattt tgttttgagt aaaaatgtgt    9480
caaatcgtgg cctctaatga ccgaagttaa tatgaggagt aaaacatccc aaacaagctt    9540
ggaaactgaa ggcgggaaac gacaatctga tcatgagcgg agaattaagg gagtcacgtt    9600
atgaccccg  ccgatgacgc gggacaagcc gttttacgtt tggaactgac agaaccgcaa    9660
cgattgaagg agccactcag ccgcgggttt ctggagttta atgagctaag cacatacgtc    9720
agaaaccatt attgcgcgtt caaaagtcgc ctaaggtcac tatcagctag caaatatttc    9780
ttgtcaaaaa tgctccactg acgttccata aattcccctc ggtatccaat tagagtctca    9840
tattcactct caatccaaat aatctgcacc ggatccgcta gaggatctcg acctgcaaga    9900
tcccgggggg caatgagata tgaaaaagcc tgaactcacc gcgacgtctg tcgagaagtt    9960
tctgatcgaa aagttcgaca gcgtctccga cctgatgcag ctctcggagg gcgaagaatc   10020
tcgtgctttc agcttcgatg taggagggcg tggatatgtc ctgcgggtaa atagctgcgc   10080
cgatggtttc tacaaagatc gttatgttta tcggcacttt gcatcggccg cgctcccgat   10140
tccggaagtg cttgacattg gggaattcag cgagagcctg acctattgca tctcccgccg   10200
tgcacagggt gtcacgttgc aagacctgcc tgaaaccgaa ctgcccgctg ttctgcagcc   10260
ggtcgcggag gccatggatg cgatcgctgc ggccgatctt agccagacga gcgggttcgg   10320
cccattcgga ccgcaaggaa tcggtcaata cactacatgg cgtgatttca tatgcgcgat   10380
tgctgatccc catgtgtatc actggcaaac tgtgatggac gacaccgtca gtgcgtccgt   10440
cgcgcaggct ctcgatgagc tgatgctttg gccgaggac  tgccccgaag tccggcacct   10500
cgtgcacgcg gatttcggct ccaacaatgt cctgacggac aatggccgca taacagcggt   10560
cattgactgg agcgaggcga tgttcgggga ttcccaatac gaggtcgcca acatcttctt   10620
ctggaggccg tggttggctt gtatggagca gcagacgcgc tacttcgagc ggaggcatcc   10680
ggagcttgca ggatcgccgc ggctccgggc gtatatgctc cgcattggtc ttgaccaact   10740
ctatcagagc ttggttgacg gcaatttcga tgatgcagct tgggcgcagg tcgatgcga    10800
cgcaatcgtc cgatccggag ccgggactgt cgggcgtaca caaatcgccc gcagaagcgc   10860
ggccgtctgg accgatggct gtgtagaagt actcgccgat agtggaaacc gacgccccag   10920
cactcgtccg gatcttgga  ggtgatgtaa catgatcaca agctgatccc ccgaatttcc   10980
ccgatcgttc aaacatttgg caataaagtt tcttaagatt gaatcctgtt gccggtcttg   11040
cgatgattat catataattt ctgttgaatt acgttaagca tgtaataatt aacatgtaat   11100
gcatgacgtt atttatgaga tgggttttta tgattagagt cccgcaatta tacatttaat   11160
```

```
acgcgataga aaacaaaata tagcgcgcaa actaggataa attatcgcgc gcggtgtcat    11220
ctatgttact agatcgggga attgatcccc cctcgacagc ttgcatgcca gcttgggctg    11280
caggtcgagg ctaaaaaact aatcgcatta tcatcccctc gacgtactgt acatataacc    11340
actggtttta tatacagcag tactgtacat ataaccactg gttttatata cagcagtcga    11400
cgtactgtac atataaccac tggttttata tacagcagta ctgtacatat aaccactggt    11460
tttatataca gcagtcgagg taagattaga tatggatatg tatatggata tgtatatggt    11520
ggtaatgcca tgtaatatgc tcgactctag gatcttcgca agacccttcc tctatataag    11580
gaagttcatt tcatttggag aggacacgct gaagctagtc gactctagcc tcgacatgtc    11640
caatttactg accgtacacc aaaatttgcc tgcattaccg gtcgatgcaa cgagtgatga    11700
ggttcgcaag aacctgatgg acatgttcag ggatcgccag gcgttttctg agcatacctg    11760
gaaaatgctt ctgtccgttt gccggtcgtg ggcggcatgg tgcaagttga ataaccggaa    11820
atggtttccc gcagaacctg aagatgttcg cgattatctt ctatatcttc aggcgcgcgg    11880
tctggcagta aaaactatcc agcaacattt gggccagcaa acatgcttc atcgtcggtc    11940 cgggctgcca cgaccaagtg acagcaatgc tgtttcactg gttatgcggc ggatccgaaa    12000
agaaaacgtt gatgccggtg aacgtgcaaa acaggctcta gcgttcgaac gcactgattt    12060
cgaccaggta agtcttcttt tcctttactc tttacagaaa tggtaatctc agatatagta    12120
atggataaga tccaaaaatg acactttttaa ccaagattgt acgaagatct ttttaaactc    12180
cattttttat tttgacatct aaattggatt taactcggcc ttgctgtatt ttggcaggtt    12240
cgttcactca tggaaaatag cgatcgctgc caggatatac gtaatctggc atttctgggg    12300
attgcttata cacccctgtt acgtatagcc gaaattgcca ggatcagggt taaagatatc    12360
tcacgtactg acggtgggag aatgttaatc catattggca gaacgaaaac gctggttagc    12420
accgcaggtg tagagaaggc acttagcctg ggggtaacta aactggtcga gcgatggatt    12480
tccgtctctg gtgtagctga tgatccgaat aactacctgt tttgccgggt cagaaaaaat    12540
ggtgttgccg cgccatctgc caccagccag ctatcaactc gcgccctgga agggattttt    12600
gaagcaactc atcgattgat ttacggcgct aaggatgact ctggtcagag atacctggcc    12660
tggtctggac acagtgcccg tgtcggagcc gcgcgagata tggcccgcgc tggagtttca    12720
ataccggaga tcatgcaagc tggtggctgg accaatgtaa atattgtcat gaactatatc    12780
cgtaacctgg atagtgaaac aggggcaatg gtgcgcctgc tggaagatgg cgattagtaa    12840
gaattcgcat gcattcatca atattattca tgcggggaaa ggcaagatta atccaactgg    12900
caaatcatcc agcgtgattg gtaacttcag ttccagcgac ttgattcgtt ttggtgctac    12960
ccacgttttc aataaggacg agatggtgga gtaaagaagg agtgcgtcga agcagatcgt    13020
tcaaacattt ggcaataaag tttcttaaga ttgaatcctg ttgccggtct tgcgatgatt    13080
atcatataat ttctgttgaa ttacgttaag catgtaataa ttaacatgta atgcatgacg    13140
ttatttatga gatgggtttt tatgattaga gtcccgcaat tatacattta atacgcgata    13200
gaaaacaaaa tatagcgcgc aaactaggat aaattatcgc gcgcggtgtc atctatgtta    13260
ctagatcata acttcgtata gcatacatta tacgaagtta tagatcttcg acctcgagca    13320
ccattcacac ttggtcaggt caagaaagct atcccacctc attgtttcca gcgttctgtt    13380
ctccgctcat tctcgtatgt tgtttatgac ctgaccttg cctttatctt ttattatgtt    13440
gccaccaatt acttccacct ccttcctcaa ccctctctt atgtgcctg ccaatttac    13500 tggtccctcc aaggctgtgt cctcactggc atttgggtta tagcacatga gtgtgggcat    13560
```

```
catgccttta gtgactatca atggcttgat gacatagttg gccttctcct ccattcctgt    13620
ctccttgtcc cttactttc atggaaacat agccatcgcc gtcatcactc taacaccggt     13680
tcccttgagc gagatgaagt atttgtccct aaaaagaaat ccaacatccg ctggttctcc    13740 aaataccta caacctacc aggccgccta ttcactctta ccataacact tgcccttggc      13800
tggccgctat acctagcatt taatgtttca ggcaggcatt atgaccgatt tgcctgtcac    13860
tttgacccat atggccctat ctacaatgat cgcgagcgaa ctgagatatt catttctgat    13920
gctggtgttc ttgctgtcac ttatggtctc taccgtcttg ctctagcaaa gggctttgct    13980
tgggttattt gcgtttatgg agtacctttg ttagtggtga gtgcatttct tgttatgatc    14040
acatatctgc aacatactca tccttcattg ccgcattatg attcttctga gtgggattgg    14100
ctgagaggcg cgctcgcaac tgttgataga gattacggaa tcttgaacaa ggtattccat    14160
aacattacag acactcatgg taataagatc ttcaacacct acaccatttt tttaatcact    14220
actacccatt gcattgaaca aacttccaag ttcttcttag cttcagatta agaaagtacc    14280 cttcttggc tttgttgatg tggtaccatt gtccattgtc ttgtgtgttt ccagggcacg     14340
acttcttcaa gagcgcatga gtgtctgtaa tgttatggaa taccttgttc aagattccgt    14400
aatctctatc aacagttgcg agcgcgcctc tcagccaatc ccactcagaa gaatcataat    14460
gcggcaatga aggatgagta tgttgcagat atgtgatcat aacaagaaat gcattcacca    14520
ctaacaaagg tactccataa acgcaaataa cccaagcaaa gcccttgct agagcaagac     14580 ggtagagacc ataagtgaca gcaagaacac cagcatcaga aatgaatatc tcagttcgct    14640
cgcgatcatt gtagataggg ccatatgggt caaagtgaca ggcaaatcgg tcataatgcc    14700
tgcctgaaac attaaatgct aggtatagcg gccagccaag ggcaagtgtt atggtaagag    14760
tgaataggcg gcctggtagg ttgttaaggt atttggagaa ccagcggatg ttggatttct    14820
ttttagggac aaatacttca tctcgctcaa gggaaccggt gttagagtga tgacggcgat    14880
ggctatgttt ccatgaaaag taagggacaa ggagacagga atggaggaga aggccaacta    14940
tgtcatcaag ccattgatag tcactaaagg catgatgccc acactcatgt gctataaccc    15000
aaatgccagt gaggacacag ccttggaggg accagtaaat tggccaggcc acataagaga    15060
ggggttgagg aaggaggtgg aagtaattgg tggcaacata ataaaagata aaggcaaggg    15120
tcaggtcata aacaacatac gagaatgagc ggagaacaga acgctggaaa caatgaggtg    15180
ggatagcttt cttgacctga ccaagtgtga atggtggatc ca                      15222
```